United States Patent
Chou et al.

(10) Patent No.: US 11,326,989 B2
(45) Date of Patent: *May 10, 2022

(54) DEVICES AND METHODS FOR TISSUE AND CELL STAINING

(71) Applicant: Essenlix Corporation, Monmouth Junction, NJ (US)

(72) Inventors: Stephen Chou, Princeton, NJ (US); Wei Ding, East Windsor, NJ (US); Ji Li, Princeton, NJ (US)

(73) Assignee: Essenlix Corporation, Monmouth Junction, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/758,938

(22) PCT Filed: Oct. 26, 2018

(86) PCT No.: PCT/US2018/057875
§ 371 (c)(1),
(2) Date: Apr. 24, 2020

(87) PCT Pub. No.: WO2019/084515
PCT Pub. Date: May 2, 2019

(65) Prior Publication Data
US 2020/0378875 A1    Dec. 3, 2020

Related U.S. Application Data

(60) Provisional application No. 62/577,347, filed on Oct. 26, 2017.

(51) Int. Cl.
*G01N 33/50* (2006.01)
*G01N 1/31* (2006.01)
(Continued)

(52) U.S. Cl.
CPC ............ *G01N 1/312* (2013.01); *G01N 1/36* (2013.01); *G06K 9/00134* (2013.01);
(Continued)

(58) Field of Classification Search
CPC .... G01N 1/312; G01N 1/36; G01N 2001/302; G01N 2001/305; G01N 21/76; G01N 21/51; G01N 2021/6482; G01N 21/69; G01N 2021/0389; G01N 2021/036; G01N 2021/651; G01N 21/0303; G01N 33/49;
(Continued)

(56) References Cited

U.S. PATENT DOCUMENTS 6,391,568 B1    3/2002   Schneider et al.
6,586,259 B1    7/2003   Mahan et al.
(Continued)

FOREIGN PATENT DOCUMENTS

WO    2017048871 A1    3/2017
WO    2018152005 A1    8/2018

OTHER PUBLICATIONS

International Report on Patentability for PCT/US18/57875 established by IPEA/US dated Apr. 6, 2020.

*Primary Examiner* — Christopher L Chin

(57) ABSTRACT

Devices and systems are provided herein relating to a novel and rapid assay for tissue staining. Methods for using the devices and systems for analyzing tissue samples are also disclosed.

100 Claims, 5 Drawing Sheets

(51) Int. Cl.
*G01N 1/36* (2006.01)
*G06K 9/00* (2022.01)
*H04M 1/72409* (2021.01)
*G01N 1/30* (2006.01)
*G01N 21/76* (2006.01)

(52) U.S. Cl.
CPC ........ *H04M 1/72409* (2021.01); *G01N 21/76* (2013.01); *G01N 2001/302* (2013.01); *G01N 2001/305* (2013.01)

(58) Field of Classification Search
CPC ........... H04M 1/72409; G06K 9/00134; A61B 5/0071; A61B 5/097; A61B 5/14532; A61B 5/1468
USPC ........ 356/244, 246; 422/401, 408, 425, 436, 422/551, 561, 563; 435/288.3, 288.7, 435/40.5, 40.52; 436/165, 805, 807
See application file for complete search history.

(56) References Cited

U.S. PATENT DOCUMENTS

| | | | |
|---|---|---|---|
| 10,132,794 B2 | 11/2018 | Chou et al. | |
| 10,605,805 B2 * | 3/2020 | Chou | ........................ G01N 1/30 |
| 10,955,334 B2 * | 3/2021 | Chou | ...................... G01N 33/49 |
| 2014/0284504 A1 | 9/2014 | Maurer et al. | |
| 2016/0349234 A1 | 12/2016 | Hillman et al. | |

* cited by examiner

DEVICES AND METHODS FOR TISSUE AND CELL STAINING

CROSS-REFERENCING

This application is a National Stage entry (§ 371) application of International Application No. PCT/US18/57875, filed on Oct. 26, 2018, which claims the benefit of U.S. Provisional Patent Application No. 62/577,347, filed on Oct. 26, 2017, the contents of which are relied upon and incorporated herein by reference in their entirety.

The entire disclosure of any publication or patent document mentioned herein is entirely incorporated by reference.

FIELD

Among other things, the present invention is related to devices and methods of performing tissue staining and imaging.

BACKGROUND

In biological and chemical assays (e.g. diagnostic testing), often it needs to stain and visualize analyte in biological samples quickly and simply. The current invention provides devices and methods for achieving these goals.

SUMMARY

In one aspect, the present invention provides a device for analyzing a tissue sample, comprising a first plate; a second plate; a plurality of spacers; and a staining liquid, wherein the plates are movable relative to each other into different configurations; one or both plates are flexible; each of the plates has, on its respective inner surface, a sample contact area for contacting a staining liquid and/or a tissue sample contains or suspected of containing a target analyte; one or both of the plates comprise the spacers that are fixed with a respective plate; the spacers have a predetermined substantially uniform height and a predetermined inter-spacer distance; and at least one of the spacers is inside the sample contact area; wherein one of the configurations is an open configuration, in which: the two plates are partially or entirely separated apart, the spacing between the plates is not regulated by the spacers, and the staining liquid and the sample are deposited on one or both of the plates; and wherein another of the configurations is a closed configuration, which is configured after the deposition of the staining liquid and the sample in the open configuration, and in the closed configuration: at least part of the sample is between the two plates and a layer of at least part of staining liquid is between the at least part of the sample and the second plate, wherein the thickness of the at least part of staining liquid layer is regulated by the plates, the sample, and the spacers, and has an average distance between the sample surface and the second plate surface is equal to or less than 250 µm with a small variation.

In one aspect, the present invention provides a device for analyzing a tissue sample, comprising a first plate; a second plate; a plurality of spacers; a transfer solution; and a staining liquid, wherein the plates are movable relative to each other into different configurations; one or both plates are flexible; each of the plates has, on its respective inner surface, a sample contact area for contacting a transfer solution and/or a tissue sample contains or suspected of containing a target analyte; one or both of the plates comprise a stain agent that is coated on the respective sample contact area and configured to, upon contacting the transfer solution, be dissolved in the transfer solution and stain the tissue sample; one or both of the plates comprise the spacers that are fixed with a respective plate; the spacers have a predetermined substantially uniform height and a predetermined inter-spacer distance; and at least one of the spacers is inside the sample contact area; wherein one of the configurations is an open configuration, in which: the two plates are partially or entirely separated apart, the spacing between the plates is not regulated by the spacers, and the staining liquid and the sample are deposited on one or both of the plates; and wherein another of the configurations is a closed configuration, which is configured after the deposition of the staining liquid and the sample in the open configuration, and in the closed configuration: at least part of the sample is between the two plates and a layer of at least part of transfer solution is between the at least part of the sample and the second plate, wherein the thickness of the at least part of transfer solution layer is regulated by the plates, the sample, and the spacers, and has an average distance between the sample surface and the second plate surface is equal to or less than 250 µm with a small variation.

In one aspect, the present invention provides a method for analyzing a tissue sample, comprising the steps of providing a tissue sample contains or suspected of containing a target analyte; providing a staining liquid; providing a first plate, a second plate, and spacers, wherein the plates are movable relative to each other into different configurations, one or both plates are flexible; each of the plates has, on its respective inner surface, a sample contact area for contacting the staining liquid and/or the tissue sample; one or both of the plates comprise the spacers that are fixed with a respective plate; the spacers have a predetermined substantially uniform height and a predetermined inter-spacer distance; and at least one of the spacers is inside the sample contact area; depositing the staining liquid and the tissue sample on one or both of the plates when the plates are in an open configuration, wherein the open configuration is a configuration in which the two plates are partially or entirely separated apart, the spacing between the two plates is not regulated by the spacers, and the sample and the staining liquid are deposited on one or both of the plates; bringing the two plates together and pressing the plates into a closed configuration, wherein the pressing comprises conformable pressing, either in parallel or sequentially, an area of at least one of the plates to press the plates together to the closed configuration, wherein the conformable pressing generates a substantially uniform pressure on the plates over the at least part of the sample, and the pressing spreads the at least part of the sample laterally between the inner surfaces of the plates; and wherein another of the configurations is the closed configuration, which is configured after the deposition of the staining liquid and the sample in the open configuration, and in the closed configuration: at least part of the sample is between the two plates and a layer of at least part of staining liquid is between the at least part of the sample and the second plate, wherein the thickness of the at least part of staining liquid layer is regulated by the plates, the sample, and the spacers, and has an average distance between the sample surface and the second plate surface is equal to or less than 250 µm with a small variation; and analyzing the target analyte when the plates are in the closed configuration.

In one aspect, the present invention provides a method for analyzing a tissue sample, comprising the steps of obtaining a tissue sample contains or suspected of containing a target analyte and a transfer solution; obtaining a first plate, a second plate, and spacers, wherein the plates are movable relative to each other into different configurations; one or both plates are flexible; each of the plates has, on its respective inner surface, a sample contact area for contacting a staining liquid and/or a tissue sample suspected of containing a target analyte; one or both of the plates comprise stain agents that are coated on the respective sample contact area and configured to, upon contacting a transfer solution, be dissolved in the transfer solution and stain the tissue sample; one or both of the plates comprise the spacers that are fixed with a respective plate; the spacers have a predetermined substantially uniform height and a predetermined inter-spacer distance; and at least one of the spacers is inside the sample contact area; depositing the staining liquid and the tissue sample on one or both of the plates when the plates are in an open configuration, wherein the open configuration is a configuration in which the two plates are partially or entirely separated apart, the spacing between the two plates is not regulated by the spacers, and the sample and the staining liquid are deposited on one or both of the plates; bringing the two plates together and pressing the plates into a closed configuration, wherein the pressing comprises conformable pressing, either in parallel or sequentially, an area of at least one of the plates to press the plates together to the closed configuration, wherein the conformable pressing generates a substantially uniform pressure on the plates over the at least part of the sample, and the pressing spreads the at least part of the sample laterally between the inner surfaces of the plates; and wherein another of the configurations is the closed configuration, which is configured after the deposition of the staining liquid and the sample in the open configuration, and in the closed configuration: at least part of the sample is between the two plates and a layer of at least part of staining liquid is between the at least part of the sample and the second plate, wherein the thickness of the at least part of staining liquid layer is regulated by the plates, the sample, and the spacers, and has an average distance between the sample surface and the second plate surface is equal to or less than 250 μm with a small variation; and analyzing the target analyte when the plates are in the closed configuration.

In one aspect, the present invention provides a method for analyzing a tissue sample, comprising the steps of providing a tissue sample contains or suspected of containing a target analyte; providing a transfer solution and a stain agent; providing a first plate, a second plate, and spacers, wherein the plates are movable relative to each other into different configurations; one or both plates are flexible; each of the plates has, on its respective inner surface, a sample contact area for contacting the tissue sample; one or both of the plates comprise a stain agent that are coated on the respective sample contact area and configured to, upon contacting a transfer solution, be dissolved in the transfer solution to form a staining liquid and stain the tissue sample; one or both of the plates comprise the spacers that are fixed with a respective plate; the spacers have a predetermined substantially uniform height and a predetermined inter-spacer distance; and at least one of the spacers is inside the sample contact area; depositing the tissue sample on one or both of the plates when the plates are in an open configuration, wherein the open configuration is a configuration in which the two plates are partially or entirely separated apart, the spacing between the two plates is not regulated by the spacers, and the sample and the staining liquid are deposited on one or both of the plates; bringing the two plates together and pressing the plates into a closed configuration, wherein the pressing comprises conformable pressing, either in parallel or sequentially, an area of at least one of the plates to press the plates together to the closed configuration, wherein the conformable pressing generates a substantially uniform pressure on the plates over the at least part of the sample, and the pressing spreads the at least part of the sample laterally between the inner surfaces of the plates; and wherein another of the configurations is the closed configuration, which is configured after the deposition of the staining liquid and the sample in the open configuration, and in the closed configuration at least part of the sample is between the two plates and a layer of at least part of staining liquid is between the at least part of the sample and the second plate, wherein the thickness of the at least part of staining liquid is regulated by the plates, the sample, and the spacers, and has an average distance between the sample surface and the second plate surface is equal to or less than 250 μm with a small variation; and without washing, analyzing the target analyte when the plates are in the closed configuration.

In one aspect, the present invention provides, a system for analyzing a tissue sample, comprising the device of any embodiment of the present disclosure; and a detector configured to detecting signals of the target analyte in the layer of uniform thickness.

In one aspect, the present invention provides a smartphone system for tissue analysis assay, comprising the device of any embodiment of the present disclosure; and a mobile communication device that comprises one or a plurality of cameras for detecting and/or imaging the sample, electronics, signal processors, hardware and software for receiving and/or processing the detected signal and/or the image of the sample and for remote communication; and an adaptor that is configured to accommodate the device that is in the closed configuration and be engageable to the mobile communication device, wherein when engaged with the mobile communication device, the adaptor is configured to facilitate the detection and/or imaging of the target analyte in the sample at the closed configuration.

The device, system, smartphone system or method of any embodiment of the present disclosure, wherein one or both of the plates is configured such that the sample can be dried thereon at the open configuration, and wherein the sample comprises bodily fluid selected from the group consisting of amniotic fluid, aqueous humour, vitreous humour, blood, breast milk, cerebrospinal fluid (CSF), cerumen (earwax), chyle, chime, endolymph, perilymph, feces, breath, gastric acid, gastric juice, lymph, mucus, pericardial fluid, peritoneal fluid, pleural fluid, pus, rheum, saliva, exhaled breath condensates, sebum, semen, sputum, sweat, synovial fluid, tears, vomit, urine, and any combination thereof.

The device, system, smartphone system or method of embodiment of the present disclosure, wherein the blood is whole blood, fractionated blood, plasma or serum.

The device, system, smartphone system or method of embodiment of the present disclosure, wherein the mucus is nasal drainage or phlegm.

The device, system, smartphone system or method of any embodiment of the present disclosure, wherein the staining liquid has a viscosity in the range of 0.1 to 3.5 mPa S.

The device, system, smartphone system or method of any embodiment of the present disclosure, wherein the sample contact area of one or both of the plates is configured such that the sample is dried thereon on one or both plates at the open configuration, and wherein the sample comprises blood smear.

The device, system, smartphone system or method of any embodiment of the present disclosure, wherein the sample contact area of one or both of the plates is adhesive to the sample, and wherein the sample is a tissue section having a thickness in the range of 1-200 µm.

The device, system, smartphone system or method of any embodiment of the present disclosure, wherein the sample is paraffin-embedded.

The device, system, smartphone system or method of any embodiment of the present disclosure, wherein the sample is fixed.

The device, system, smartphone system or method of any embodiment of the present disclosure, wherein the staining liquid comprises a fixative capable of fixing the sample.

The device, system, smartphone system or method of any embodiment of the present disclosure, wherein the staining liquid comprises a blocking agent, wherein the blocking agent is configured to disable non-specific endogenous species in the sample to react with detection agents that are used to specifically label the target analyte.

The device, system, smartphone system or method of any embodiment of the present disclosure, wherein the staining liquid comprises a deparaffinizing agent capable of removing paraffin in the sample.

The device, system, smartphone system or method of any embodiment of the present disclosure, wherein the staining liquid comprises a permeabilizing agent capable of permeabilizing cells in the tissue sample that contain the target analyte.

The device, system, smartphone system or method of any embodiment of the present disclosure, wherein the staining liquid comprises an antigen retrieval agent capable of facilitating retrieval of antigen.

The device, system, smartphone system or method of any embodiment of the present disclosure, wherein the staining liquid comprises a detection agent that specifically label the target analyte in the sample.

The device, system, smartphone system or method of any embodiment of the present disclosure, wherein the sample contact area of one or both plates comprise a storage site that contains a blocking agent, wherein the blocking agent is configured to disable non-specific endogenous species in the sample to react with the detection agent that is used to specifically label the target analyte.

The device, system, smartphone system or method of any embodiment of the present disclosure, wherein the sample contact area of one or both plates comprise a storage site that contains a deparaffinizing agent capable of removing paraffin in the sample.

The device, system, smartphone system or method of any embodiment of the present disclosure, wherein the sample contact area of one or both plates comprise a storage site that contains a permeabilizing agent capable of permeabilizing cells in the tissue sample that contain the target analyte.

The device, system, smartphone system or method of any embodiment of the present disclosure, wherein the sample contact area of one or both plates comprise a storage site that contains an antigen retrieval agent capable of facilitating retrieval of antigen.

The device, system, smartphone system or method of any embodiment of the present disclosure, wherein the sample contact area of one or both plates comprise a storage site that contains a detection agent that specifically label the target analyte in the sample.

The device, system, smartphone system or method of any embodiment of the present disclosure, wherein the detection agent comprises a compound selected from the group consisting of: Acid fuchsin, Alcian blue 8 GX, Alizarin red S, Aniline blue WS, Auramine O, Azocarmine B, Azocarmine G, Azure A, Azure B, Azure C, Basic fuchsine, Bismarck brown Y, Brilliant cresyl blue, Brilliant green, Carmine, Chlorazol black E, Congo red, C.I. Cresyl violet, Crystal violet, Darrow red, Eosin B, Eosin Y, Erythrosin, Ethyl eosin, Ethyl green, Fast green F C F, Fluorescein Isothiocyanate, Giemsa Stain, Hematoxylin, Hematoxylin & Eosin, Indigo carmine, Janus green B, Jenner stain 1899, Light green SF, Malachite green, Martius yellow, Methyl orange, Methyl violet 2B, Methylene blue, Methylene blue, Methylene violet, (Bernthsen), Neutral red, Nigrosin, Nile blue A, Nuclear fast red, Oil Red, Orange G, Orange II, Orcein, Pararosaniline, Phloxin B, Protargol S, Pyronine B, Pyronine, Resazurin, Rose Bengal, Safranine O, Sudan black B, Sudan III, Sudan IV, Tetrachrome stain (MacNeal), Thionine, Toluidine blue, Weigert, Wright stain, and any combination thereof.

The device, system, smartphone system or method of any embodiment of the present disclosure, wherein one or both of the plates further comprise, on the respective sample contact area, a cell viability dye selected from the group consisting of: Propidium Iodide, 7-AAD, Trypan blue, Calcein Violet AM, Calcein AM, Fixable Viability Dyes, SYTO9 and other nucleic acid dyes, Resazurin and Formazan (MTT/XTT) and other mitochondrial dyes, and any combination thereof.

The device, system, smartphone system or method of any embodiment of the present disclosure, wherein the detection agent comprises an antibody configured to specifically bind to the target analyte in the sample.

The device, system, smartphone system or method of any prior claim, wherein the detection agent comprises an oligonucleotide probe configured to specifically bind to DNA and/or RNA in the sample.

The device, system, smartphone system or method of any embodiment of the present disclosure, wherein the detection agent is labeled with a reporter molecule, wherein the reporter molecule is configured to provide a detectable signal to be read and analyzed.

The device, system, smartphone system or method of embodiment of the present disclosure, wherein the signal is selected from the group consisting of luminescence selected from photoluminescence, electroluminescence, and electrochemiluminescence, light absorption, reflection, transmission, diffraction, scattering, or diffusion, surface Raman scattering, electrical impedance selected from resistance, capacitance, and inductance, magnetic relaxivity and a combination thereof.

The device, system, smartphone system or method of any embodiment of the present disclosure, wherein the sample contact area of one or both of the plates comprise a binding site that contains a capture agent, wherein the capture agent is configured to bind to the target analyte on the surface of cells in the sample and immobilize the cells.

The method of any embodiment of the present disclosure, wherein the depositing step further comprises the steps of depositing and drying the sample on one or both of the plates before depositing the remaining of the staining liquid on top of the dried sample, and wherein the sample comprises a blood smear that is dried on one or both plates.

The method of any embodiment of the present disclosure, wherein the depositing step further comprises the steps of depositing and attaching the sample to one or both of the plates before depositing the staining liquid on top of the sample, wherein the sample contact area of one or both of the plates is adhesive to the sample, and wherein the sample is a tissue section having a thickness in the range of 1-200 µm.

The method of any embodiment of the present disclosure, before the analyzing step (e), further comprising: incubating the sample at the closed configuration for a period of time that is longer than the time it takes for the detection agent to diffuse across the layer of uniform thickness and the sample.

The method of any embodiment of the present disclosure, before the analyzing step (e), further comprising the step of incubating the sample at the closed configuration at a predetermined temperature in the range of 30-75° C.

The method of any embodiment of the present disclosure, wherein the staining liquid comprises the transfer solution.

The smartphone system of any embodiment of the present disclosure, wherein the mobile communication device is configured to communicate test results to a medical professional, a medical facility or an insurance company.

The smartphone system of any embodiment of the present disclosure, wherein the mobile communication device is further configured to communicate information on the subject with the medical professional, medical facility or insurance company.

The smartphone system of any embodiment of the present disclosure, wherein the mobile communication device is configured to receive a prescription, diagnosis or a recommendation from a medical professional.

The smartphone system of any embodiment of the present disclosure, wherein the mobile communication device communicates with the remote location via a WIFI or cellular network.

The smartphone system of any embodiment of the present disclosure, wherein the mobile communication device is a mobile phone.

The device, system, smartphone system or method of any embodiment of the present disclosure, wherein the pressing is performed by a human hand.

The device, system, smartphone system or method of any embodiment of the present disclosure, wherein at least a portion of the inner surface of one plate or both plates is hydrophilic.

The device, system, smartphone system or method of any embodiment of the present disclosure, wherein the inter spacer distance is periodic.

The device, system, smartphone system or method of any embodiment of the present disclosure, wherein the sample is a deposition directly from a subject to the plate without using any transferring devices.

The device, system, smartphone system or method of any embodiment of the present disclosure, wherein after the sample deformation at a closed configuration, the sample maintains the same final sample thickness, when some or all of the compressing forces are removed.

The device, system, smartphone system or method of any embodiment of the present disclosure, wherein the spacers have pillar shape and nearly uniform cross-section.

The device, system, smartphone system or method of any embodiment of the present disclosure, wherein the inter spacer distance (SD) is equal or less than about 120 μm (micrometer).

The device, system, smartphone system or method of any embodiment of the present disclosure, wherein the inter spacer distance (SD) is equal or less than about 100 μm (micrometer).

The device, system, smartphone system or method of any embodiment of the present disclosure, wherein the fourth power of the inter-spacer-distance (ISD) divided by the thickness (h) and the Young's modulus (E) of the flexible plate (ISD$^4$/(hE)) is $5 \times 10^6$ μm$^3$/GPa or less.

The device, system, smartphone system or method of any embodiment of the present disclosure, wherein the fourth power of the inter-spacer-distance (ISD) divided by the thickness (h) and the Young's modulus (E) of the flexible plate (ISD$^4$/(hE)) is $5 \times 10^5$ μm$^3$/GPa or less.

The device, system, smartphone system or method of any embodiment of the present disclosure, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one).

The device, system, smartphone system or method of any embodiment of the present disclosure, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one), wherein the fourth power of the inter-spacer-distance (ISD) divided by the thickness (h) and the Young's modulus (E) of the flexible plate (ISD$^4$/(hE)) is $5 \times 10^6$ μm$^3$/GPa or less.

The device, system, smartphone system or method of any embodiment of the present disclosure, wherein the ratio of the inter-spacing distance of the spacers to the average width of the spacer is 2 or larger, and the filling factor of the spacers multiplied by the Young's modulus of the spacers is 2 MPa or larger.

The device, kit, system, smartphone system, and method of any embodiment of the present disclosure, wherein the target analytes is a protein, peptide, nucleic acid, synthetic compound, or an inorganic compound.

The device, system, smartphone system, and method of any embodiment of the present disclosure, wherein the sample is a biological sample selected from amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, and urine.

The device, system, smartphone system, and method of any embodiment of the present disclosure, wherein the spacers have a shape of pillars and a ratio of the width to the height of the pillar is equal or larger than one.

The device, system, smartphone system or method of any embodiment of the present disclosure, wherein the sample that is deposited on one or both of the plates has an unknown volume.

The device, system, smartphone system, and method of any embodiment of the present disclosure, wherein the spacers have a shape of pillar, and the pillar has substantially uniform cross-section.

The device, system, smartphone system, and method of any embodiment of the present disclosure, wherein the samples are for the detection, purification and quantification of chemical compounds or biomolecules that correlates with the stage of certain diseases.

The device, system, smartphone system, and method of any embodiment of the present disclosure, wherein the sample is related to infectious and parasitic disease, injuries, cardiovascular disease, cancer, mental disorders, neuropsychiatric disorders, pulmonary diseases, renal diseases, and other and organic diseases.

The device, system, smartphone system, and method of any embodiment of the present disclosure, wherein the samples are related to the detection, purification and quantification of microorganism.

The device, system, smartphone system, and method of any embodiment of the present disclosure, wherein the samples is related to a virus, fungus and bacterium from environment, e.g., water, soil, or biological samples.

The device, system, smartphone system, and method of any embodiment of the present disclosure, wherein the samples is related to the detection, quantification of chemical compounds or biological samples that pose hazard to food safety or national security, e.g. toxic waste, anthrax.

The device, system, smartphone system, and method of any embodiment of the present disclosure, wherein the samples are related to quantification of vital parameters in medical or physiological monitor.

The device, system, smartphone system, and method of any embodiment of the present disclosure, wherein the samples are related to glucose, blood, oxygen level, total blood count.

The device, system, smartphone system, and method of any embodiment of the present disclosure, wherein the samples are related to the detection and quantification of specific DNA or RNA from bio-samples.

The device, system, smartphone system, and method of any embodiment of the present disclosure, wherein the samples are related to the sequencing and comparing of genetic sequences in DNA in the chromosomes and mitochondria for genome analysis.

The device, system, smartphone system, and method of any embodiment of the present disclosure, wherein the samples are related to detect reaction products, e.g., during synthesis or purification of pharmaceuticals.

The device, system, smartphone system, and method of any embodiment of the present disclosure, wherein the samples are cells, tissues, bodily fluids, and stool.

The device, system, smartphone system, and method of any embodiment of the present disclosure, wherein the sample is the sample in the detection of proteins, peptides, nucleic acids, synthetic compounds, inorganic compounds.

The device, system, smartphone system, and method of any embodiment of the present disclosure, wherein the sample is the sample in the fields of human, veterinary, agriculture, foods, environments, and drug testing.

The device, system, smartphone system or method of any embodiment of the present disclosure, wherein the sample is a biological sample is selected from blood, serum, plasma, a nasal swab, a nasopharyngeal wash, saliva, urine, gastric fluid, spinal fluid, tears, stool, mucus, sweat, earwax, oil, a glandular secretion, cerebral spinal fluid, tissue, semen, vaginal fluid, interstitial fluids derived from tumorous tissue, ocular fluids, spinal fluid, a throat swab, breath, hair, finger nails, skin, biopsy, placental fluid, amniotic fluid, cord blood, lymphatic fluids, cavity fluids, sputum, pus, microbiota, meconium, breast milk, exhaled condensate nasopharyngeal wash, nasal swab, throat swab, stool samples, hair, finger nail, ear wax, breath, connective tissue, muscle tissue, nervous tissue, epithelial tissue, cartilage, cancerous sample, and bone.

BRIEF DESCRIPTION OF THE DRAWINGS

A skilled artisan will understand that the drawings, described below, are for illustration purposes only. The drawings are not intended to limit the scope of the present teachings in any way. The drawings are not entirely in scale. In the figures that present experimental data points, the lines that connect the data points are for guiding a viewing of the data only and have no other means.

DETAILED DESCRIPTION OF EXEMPLARY EMBODIMENTS

Figure 1:
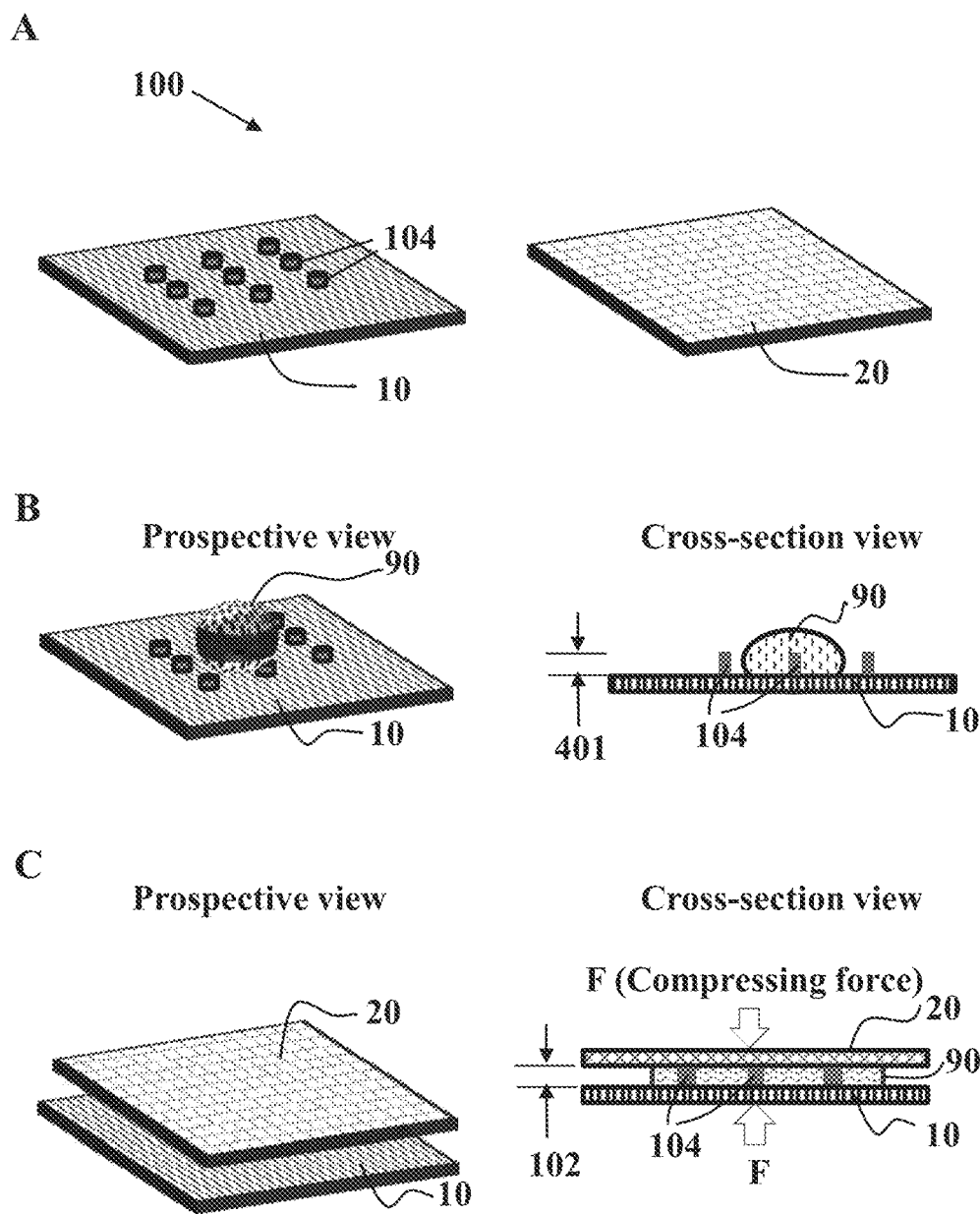
FIG. 1 shows an embodiment of a generic QMAX device.

The following detailed description illustrates some embodiments of the invention by way of example and not by way of limitation. The section headings and any subtitles used herein are for organizational purposes only and are not to be construed as limiting the subject matter described in any way. The contents under a section heading and/or subtitle are not limited to the section heading and/or subtitle, but apply to the entire description of the present invention.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

One aspect of the present invention is to provide devices and methods for easy and rapid tissue staining by utilizing a pair of plates that are movable to each other to manipulate a tissue sample and/or a small volume of staining liquid, reducing sample/staining liquid thickness, making a contact between the sample and staining reagent, etc.—all of them have beneficial effects on the tissue staining.

Another aspect of the present invention is to provide for easy and rapid tissue staining by coating staining reagents on one or both of the plate(s), which upon contacting the liquid sample and/or the staining liquid, are dissolved and diffuse in the sample and/or the staining liquid, easing the handling of staining reagents with no need of professional training.

Another aspect of the present invention is to ensure uniform access of the sample to the staining reagent by utilizing the plates and a plurality of spacers of a uniform height to force the sample and/or staining liquid to form a thin film of uniform thickness, leading to same diffusion distance for the staining reagents across a large lateral area over the sample.

Another aspect of the present invention is to provide systems for easy and rapid tissue staining and imaging by combining the pair of plates for staining with a mobile communication device adapted for acquiring and analyzing images of the tissue sample stained by the plates. Optionally, the mobile communication is configured to send the imaging data and/or analysis results to a remote location for storage and/or further analysis and interpretation by professional staff or software.

Another aspect of the present invention is to provide devices, systems and methods for immunohistochemistry.

Another aspect of the present invention is to provide devices, systems and methods for H&E stains, special stains, and/or cell viability stains.

Another aspect of the present invention is to provide devices, systems and methods for in situ hybridization.

Another aspect of the present invention is to provide devices, systems and methods for staining biological materials (e.g. for staining of cells or tissues, nucleic acid stains, H&E stains, special stains, and/or cell viability stains. etc.) without washing, and in some embodiments, in a single step.

QMAX Device for Tissue Staining and Cell Imaging

FIG. 1 shows an embodiment of a generic QMAX device, wherein Q: quantification; M: magnifying; A: adding reagents; X: acceleration; also known as compressed regulated open flow (CROF)) device. The generic QMAX device comprises a first plate 10 and a second plate 20. In particular, panel (A) shows the perspective view of a first plate 10 and a second plate 20 wherein the first plate has spacers. It should be noted, however, that the spacers also are fixed on the second plate 20 (not shown) or on both first plate 10 and second plate 20 (not shown). Panel (B) shows the perspective view and a sectional view of depositing a sample 90 on the first plate 10 at an open configuration. It should be noted, however, that the sample 90 also is deposited on the second plate 20 (not shown), or on both the first plate 10 and the second plate 20 (not shown). Panel (C) illustrates (i) using the first plate 10 and second plate 20 to spread the sample 90 (the sample flow between the inner surfaces of the plates) and reduce the sample thickness, and (ii) using the spacers and the plate to regulate the sample thickness at the closed configuration of the QMAX device. The inner surfaces of each plate have one or a plurality of binding sites and or storage sites (not shown).

In some embodiments, the spacers 40 have a predetermined uniform height and a predetermined uniform inter-spacer distance. In the closed configuration, as shown in panel (C) of FIG. 1, the spacing between the plates and the thus the thickness of the sample 90 is regulated by the spacers 40. In some embodiments, the uniform thickness of the sample 90 is substantially similar to the uniform height of the spacers 40. It should be noted that although FIG. 1 shows the spacers 40 to be fixed on one of the plates, in some embodiments the spacers are not fixed. For example, in certain embodiments the spacers is mixed with the sample so that when the sample is compressed into a thin layer, the spacers, which is rigid beads or particles that have a uniform size, regulate the thickness of the sample layer.

Figure 2:
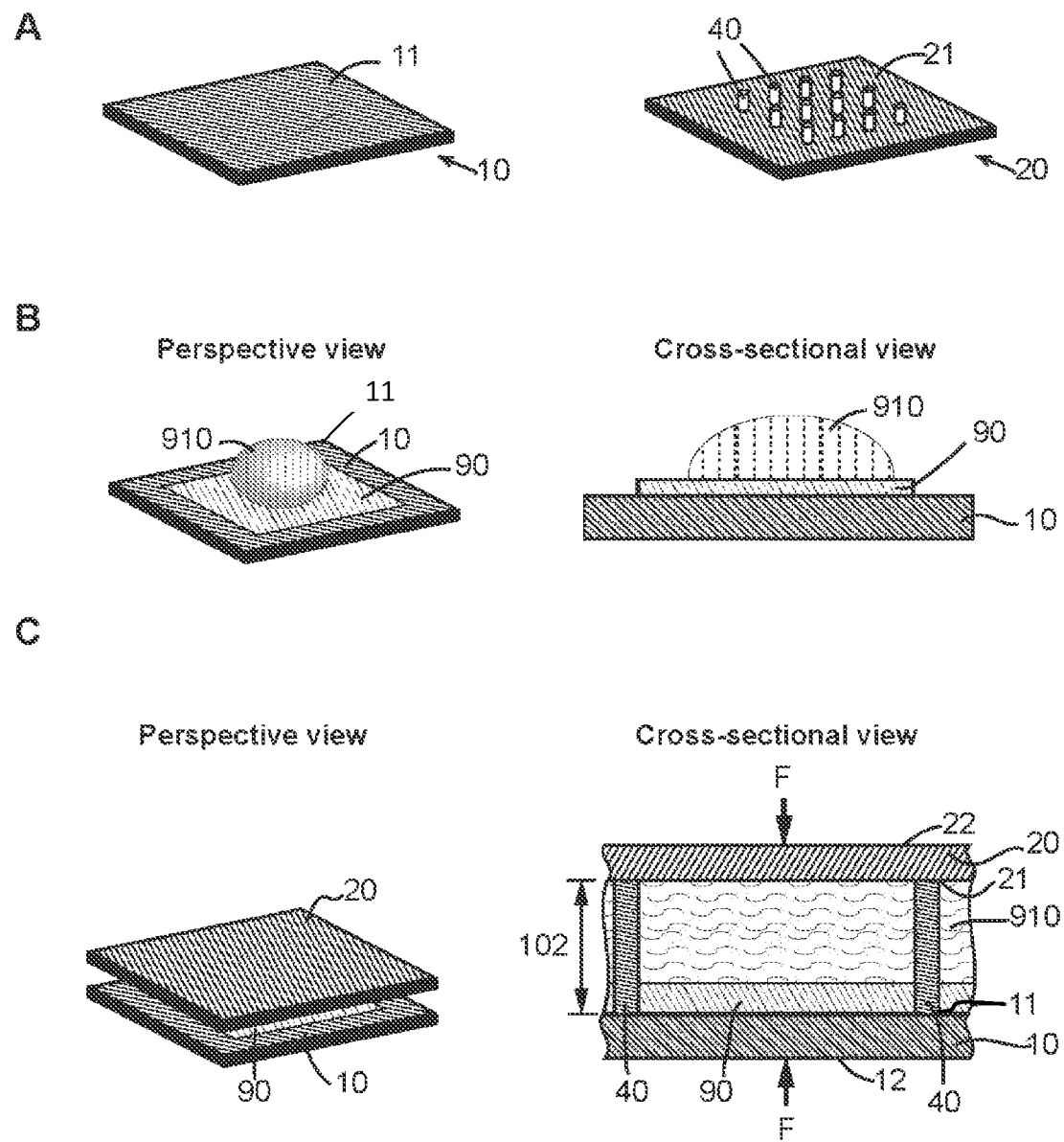
FIG. 2 shows an embodiment of a QMAX device used for tissue staining and imaging.

FIG. 2 schematically shows an embodiment of a QMAX device used for staining. As shown in the figure, the device comprises a first plate 10, a second plate 20, and spacers 40. The first plate 10 comprises an inner surface 11. The second plate 20 comprises an inner surface 21. The plates are movable relative to each other into different configurations, one or both plates are flexible. Each of the plates has, on its respective inner surface, a sample contact area (not indicated) for contacting a staining liquid 910 and/or a tissue sample 90 suspected of containing a target analyte. The second plate 20 comprises the spacers 40 that are fixed to its inner surface 21. The spacers 40 have a predetermined substantially uniform height and a predetermined inter-spacer distance, and at least one of the spacers is inside the sample contact area.

FIG. 2 panels (A) and (B) schematically illustrate one of the different configurations, i.e., an open configuration, in accordance with an embodiment. As shown in Fig. 2 panels (A) and (B), in the open configuration, the first plate 10 and the second plate 20 are partially or entirely separated apart, the spacing 102 between the two plates is not regulated by the spacers 40, and the staining liquid 910 and the sample 90 are deposited on the inner surface 11 of the first plate 10. It should be noted, the staining liquid 910 and the sample 90 can also be deposited on the second plate 20 or both plates.

FIG. 2 panel (C) schematically illustrates a closed configuration of the first and second plates, in accordance with an embodiment. The closed configuration is configured after the staining liquid 910 and the sample 90 are deposited on the QMAX device in the open configuration, as shown in panel (B). And in the closed configuration, at least part of the sample 90 is between the two plates and a layer of at least part of staining liquid 910 is between the at least part of the sample 90 and the second plate 20, wherein the thickness of the at least part of staining liquid layer is regulated by the two plates, the sample 90, and the spacers 40, and an average distance between the sample surface and the second plate surface is equal or less than 250 μm with a small variation. The first plate 10 also comprises an outer surface 12 opposing the inner surface 11. The second plate 20 also comprises an outer surface 22 opposing the inner surface 21.

It is one aspect of the present invention to provide easy and rapid devices and methods for tissue staining. In some embodiments, the reduction of the thickness of the staining liquid significantly reduces the time of staining agent(s) to diffuse across the thickness of the staining liquid, hence decreasing the saturation time for whatever purposes the staining agent(s) is for. For instance, such a configuration decreases the saturation time for antigen-antibody binding, which is the speed-limiting step of immunostaining, by reducing the diffusion distance of the antibody used for the staining, greatly promoting the overall speed for immunostaining.

It is another aspect of the present invention to provide uniform access to staining agent for the sample using the devices and methods for tissue staining disclosed therein. In some embodiments, the uniform thickness of the staining liquid engendered by the particular configuration of the plates and spacers ensures the uniform access of the sample to the staining agent that is dissolved and diffuses in the staining liquid.

Sample

It should be noted that, the term "sample" as used herein, unless otherwise specified, refers to a liquid bio/chemical sample or a non-liquid sample.

In some embodiments, the liquid sample is originally obtained in a liquid form, such as, blood and saliva. In some embodiments, the originally obtained sample specimen is not in a liquid state, for instance, in a solid state or a gaseous state. In such cases, the non-liquid sample is converted to a liquid form when being collected and preserved using the device and method provided by the present invention. The method for such conversion includes, but not limited to, mixture with a liquid medium without dissolution (the end product is a suspension), dissolution in a liquid medium, melting into a liquid form from a solid form, condensation into a liquid form from a gaseous form (e.g. exhaled breath condensate).

In some embodiments, the sample can be dried thereon at the open configuration, and wherein the sample comprises bodily fluid selected from the group consisting of: amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, urine, and any combination thereof.

In some embodiments, the sample contact area of one or both of the plates is configured such that the sample can be dried thereon at the open configuration, and the sample comprises blood smear and is dried on one or both plates.

In some embodiments, the sample is a solid sample, for instance, a tissue section. In some embodiments, the sample is a solid tissue section having a thickness in the range of 1-200 µm. In some embodiments, the sample contact area of one or both of the plates is adhesive to the sample. In some embodiments, the sample is paraffin-embedded. In some embodiments, the sample is fixed (e.g., formalin, paraformaldehyde and the like).

Staining Liquid

In some embodiments, the staining liquid has a viscosity in the range of 0.1 to 3.5 mPa S.

In some embodiments, one primary function of the staining liquid is to serve a transfer medium. The reagents stored (dried/coated) on the plate(s), upon contacting the staining liquid, are dissolved and diffuse in the staining liquid. As such, the staining liquid serves as a transfer medium to provide access for the reagents stored on the plate(s) to the sample.

In some embodiments, one primary function of the staining liquid is to serve as a holding solution. When the plates are pressed to enter the closed configuration, in some embodiments, the plates are configured to "self-hold" at closed configuration after the removal of the external compressing force, due to forces like capillary force provided by the liquid sample. In the cases where the sample specimen is not in a liquid form, the liquid medium therefore provides such forces like capillary force needed for the "self-holding" of the plates.

In some embodiments, the staining liquid comprises buffer pairs to balance the pH value of the final solution. In some embodiments, the staining liquid does not comprise particular component capable of altering the properties of the sample.

In some embodiments, the staining liquid comprises reagents needed for the processing, fixation, or staining of the sample, as further discussed in details in the following sections.

In some embodiments, the staining liquid comprises fixative capable of fixing the sample.

In some embodiments, the staining liquid comprises blocking agents, wherein the blocking agents are configured to disable non-specific endogenous species in the sample to react with detection agents that are used to specifically label the target analyte.

In some embodiments, the staining liquid comprises deparaffinizing agents capable of removing paraffin in the sample.

In some embodiments, the staining liquid comprises permeabilizing agents capable of permeabilizing cells in the tissue sample that contain the target analyte.

In some embodiments, the staining liquid comprises antigen retrieval agents capable of facilitating retrieval of antigen.

In some embodiments, the staining liquid comprises detection agents that specifically label the target analyte in the sample.

Plate Storage Site

In some embodiments, the sample contact area of one or both plates comprise a storage site that contains reagents needed for the processing, fixation, or staining of the sample. These reagents, upon contacting the liquid sample or the staining liquid, are dissolved and diffuse in the liquid sample/staining liquid.

In some embodiments, the sample contact area of one or both plates comprise a storage site that contains blocking agents, wherein the blocking agents are configured to disable non-specific endogenous species in the sample to react with detection agents that are used to specifically label the target analyte.

In some embodiments, the sample contact area of one or both plates comprise a storage site that contains deparaffinizing agents capable of removing paraffin in the sample.

In some embodiments. the sample contact area of one or both plates comprise a storage site that contains permeabilizing agents capable of permeabilizing cells in the tissue sample that contain the target analyte.

In some embodiments. the sample contact area of one or both plates comprise a storage site that contains antigen retrieval agents capable of facilitating retrieval of antigen. In some embodiments, the sample contact area of one or both plates comprise a storage site that contains detection agents that specifically label the target analyte in the sample.

In some embodiments, the sample contact area of one or both of the plates comprise a binding site that contains capture agents, wherein the capture agents are configured to bind to the target analyte on the surface of cells in the sample and immobilize the cells.

Detection Agent

In some embodiments, the detection agent comprises dyes for a stain selected from the group consisting of: Acid fuchsin, Alcian blue 8 GX, Alizarin red S, Aniline blue WS, Auramine O, Azocarmine B, Azocarmine G, Azure A, Azure B, Azure C, Basic fuchsine, Bismarck brown Y, Brilliant cresyl blue, Brilliant green, Carmine, Chlorazol black E, Congo red, C.I. Cresyl violet, Crystal violet, Darrow red, Eosin B, Eosin Y, Erythrosin, Ethyl eosin, Ethyl green, Fast green F C F, Fluorescein Isothiocyanate, Giemsa Stain, Hematoxylin, Hematoxylin & Eosin, Indigo carmine, Janus green B, Jenner stain 1899, Light green SF, Malachite green, Martius yellow, Methyl orange, Methyl violet 2B, Methylene blue, Methylene blue, Methylene violet, (Bernthsen), Neutral red, Nigrosin, Nile blue A, Nuclear fast red, Oil Red, Orange G, Orange II, Orcein, Pararosaniline, Phloxin B, Protargol S, Pyronine B, Pyronine, Resazurin, Rose Bengal, Safranine O, Sudan black B, Sudan III, Sudan IV, Tetrachrome stain (MacNeal), Thionine, Toluidine blue, Weigert, Wright stain, and any combination thereof.

In some embodiments, the detection agent comprises antibodies configured to specifically bind to protein analyte in the sample.

In some embodiments, the detection agent comprises oligonucleotide probes configured to specifically bind to DNA and/or RNA in the sample.

In some embodiments, the detection agent is labeled with a reporter molecule, wherein the reporter molecule is configured to provide a detectable signal to be read and analyzed.

In some embodiments, the reporter molecule comprises fluorescent molecules (fluorophores), including, but not limited to, IRDye800CW, Alexa 790, Dylight 800, fluorescein, fluorescein isothiocyanate, succinimidyl esters of carboxyfluorescein, succinimidyl esters of fluorescein, 5-isomer of fluorescein dichlorotriazine, caged carboxyfluorescein-alanine-carboxamide, Oregon Green 488, Oregon Green 514; Lucifer Yellow, acridine Orange, rhodamine, tetramethylrhodamine, Texas Red, propidium iodide, JC-1 (5,5',6,6'-tetrachloro-1,1',3,3'-tetraethylbenzimidazoylcarbocyanine iodide), tetrabromorhodamine 123, rhodamine 6G, TMRM (tetramethyl rhodamine methyl ester), TMRE (tetramethyl rhodamine ethyl ester), tetramethylrosamine, rhodamine B and 4-dimethylaminotetramethylrosamine, green fluorescent protein, blue-shifted green fluorescent protein, cyan-shifted green fluorescent protein, redshifted green fluorescent protein, yellow-shifted green fluorescent protein, 4-acetamido-4'-isothiocyanatostilbene-2,2'disulfonic acid; acridine and derivatives, such as acridine, acridine isothiocyanate; 5-(2'-aminoethyl)aminonaphthalene-1-sulfonic acid (EDANS); 4-amino-N-[3-vinylsulfonyl)phenyl]naphth-alimide-3,5 disulfonate; N-(4-anilino-1-naphthyl)maleimide; anthranilamide; 4,4-difluoro-5-(2-thienyl)-4-bora-3a,4a diaza-5-indacene-3-propioni-c acid BODIPY; cascade blue; Brilliant Yellow; coumarin and derivatives: coumarin, 7-amino-4-methylcoumarin (AMC, Coumarin 120), 7-amino-4-trifluoromethylcoumarin (Coumarin 151); cyanine dyes; cyanosine; 4',6-diaminidino-2-phenylindole (DAPI); 5',5"-dibromopyrogallol sulfonaphthalein (Bromopyrogallol Red); 7-diethylamino-3-(4'-isothiocyanatophenyl)-4-methylcoumarin; diethylenetriaamine pentaacetate; 4,4'-diisothiocyanatodihydro-stilbene-2-,2'-disulfonic acid; 4,4'-diisothiocyanatostilbene-2,2'-disulfonic acid; 5-(dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM), 5-(4,6-dichlorotriazin-2-yl)amino- -fluorescein (DTAF), 2',7'dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; ophthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of 5 sulforhodamine (Texas Red); N,N, N',N'-tetramethyl-6-carboxyrhodamine (TAMRA); tetramethyl rhodamine; tetramethyl hodamine isothiocyanate (TRITC); riboflavin; 5-(2'-aminoethyl) aminonaphthalene-1-sulfonic acid (EDANS), 4-(4'-dimethylaminophenylazo) benzoic acid (DABCYL), rosolic acid; CAL Fluor Orange 560; terbium chelate derivatives; Cy 3; Cy 5; Cy 5.5; Cy 7; IRD 700; IRD 800; La Jolla Blue; phthalo cyanine; and naphthalo cyanine, coumarins and related dyes, xanthene dyes such as rhodols, resorufins, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, fluorescent europium and terbium complexes; combinations thereof, and the like. Suitable fluorescent proteins and chromogenic proteins include, but are not limited to, a green fluorescent protein (GFP), including, but not limited to, a GFP derived from *Aequoria victoria* or a derivative thereof, e.g., a "humanized" derivative such as Enhanced GFP; a GFP from another species such as *Renilla reniformis, Renilla mulleri*, or *Ptilosarcus guernyi*; "humanized" recombinant GFP (hrGFP); any of a variety of fluorescent and colored proteins from *Anthozoan* species; any combination thereof; and the like.

In some embodiments, the signal is selected from the group consisting of:
  i. luminescence selected from photo-luminescence, electroluminescence, and electrochemiluminescence;
  ii. light absorption, reflection, transmission, diffraction, scattering, or diffusion;
  iii. surface Raman scattering;
  iv. electrical impedance selected from resistance, capacitance, and inductance;
  v. magnetic relaxivity; and
  vi. any combination of i-v.

Immunohistochemistry

In some embodiments, the devices and methods of the present invention are useful for conducting immunohistochemistry on the sample.

In immunohistochemical (IHC) staining methods, a tissue sample is fixed (e.g., in paraformaldehyde), optionally embedding in wax, sliced into thin sections that are less then 100 μm thick (e.g., 2 μm to 6 μm thick), and then mounted onto a support such as a glass slide. Once mounted, the tissue sections may be dehydrated using alcohol washes of increasing concentrations and cleared using a detergent such as xylene. In certain cases, fixation is also an optional step, for instance, for blood smear staining.

In most IHC methods, a primary and a secondary antibody may be used. In such methods, the primary antibody binds to antigen of interest (e.g., a biomarker) and is unlabeled. The secondary antibody binds to the primary antibody and directly conjugated either to a reporter molecule or to a linker molecule (e.g., biotin) that can recruit reporter molecule that is in solution. Alternatively, the primary antibody itself may be directly conjugated either to a reporter molecule or to a linker molecule (e.g., biotin) that can recruit reporter molecule that is in solution. Reporter molecules include fluorophores (e.g., FITC, TRITC, AMCA, fluorescein and rhodamine) and enzymes such as alkaline phosphatase (AP) and horseradish peroxidase (HRP), for which there are a variety of fluorogenic, chromogenic and chemiluminescent substrates such as DAB or BCIP/NBT.

In direct methods, the tissue section is incubated with a labeled primary antibody (e.g. an FITC-conjugated antibody) in binding buffer. The primary antibody binds directly with the antigen in the tissue section and, after the tissue section has been washed to remove any unbound primary antibody, the section is to be analyzed by microscopy.

In indirect methods, the tissue section is incubated with an unlabeled primary antibody that binds to the target antigen in the tissue. After the tissue section is washed to remove unbound primary antibody, the tissue section is incubated with a labeled secondary antibody that binds to the primary antibody.

After immunohistochemical staining of the antigen, the tissue sample may be stained with another dye, e.g., hematoxylin, Hoechst stain and DAPI, to provide contrast and/or identify other features.

The present device may be used for immunohistochemical (IHC) staining a tissue sample. In these embodiments, the device may comprise a first plate and a second plate, wherein: the plates are movable relative to each other into different configurations; one or both plates are flexible; each of the plates has, on its respective surface, a sample contact area for contacting a tissue sample or a IHC staining liquid; the sample contact area in the first plate is smooth and planner; the sample contact area in the second plate comprise spacers that are fixed on the surface and have a predetermined substantially uniform height and a predetermined constant inter-spacer distance that is in the range of 7 µm to 200 µm;

wherein one of the configurations is an open configuration, in which: the two plates are completely or partially separated apart, the spacing between the plates is not regulated by the spacers; and wherein another of the configurations is a closed configuration which is configured after a deposition of the sample and the IHC staining liquid in the open configuration; and in the closed configuration: at least part of the sample is between the two plates and a layer of at least part of staining liquid is between the at least part of the sample and the second plate, wherein the thickness of the at least part of staining liquid layer is regulated by the plates, the sample, and the spacers, and has an average distance between the sample surface and the second plate surface is equal or less than 250 µm with a small variation.

As discussed above, in some embodiments, the device may comprise a dry IHC staining agent coated on the sample contact area of one or both plates. In some embodiments, the device may comprise a dry IHC staining agent coated on the sample contact area of the second plate, and the IHC staining liquid comprise a liquid that dissolve the dry IHC staining agent. In some embodiments, the thickness of the sample is 2 µm to 6 µm.

H&E, Special stains, and Cell Viability Stains

In some embodiments, the devices and methods of the present invention are useful for conducting H&E stain, special stains, and cell viability stains.

Hematoxylin and eosin stain or haematoxylin and eosin stain (H&E stain or HE stain) is one of the principal stains in histology. It is the most widely used stain in medical diagnosis and is often the gold standard; for example when a pathologist looks at a biopsy of a suspected cancer, the histological section is likely to be stained with H&E and termed "H&E section", "H+E section", or "HE section". A combination of hematoxylin and eosin, it produces blues, violets, and reds.

In diagnostic pathology, the "special stain" terminology is most commonly used in the clinical environment, and simply means any technique other than the H&E method that is used to impart colors to a specimen. This also includes immunohistochemical and in situ hybridization stains. On the other hand, the H&E stain is the most popular staining method in histology and medical diagnosis laboratories.

In any embodiments, the dry binding site may comprise a capture agent such as an antibody or nucleic acid. In some embodiments, the releasable dry reagent may be a labeled reagent such as a fluorescently-labeled reagent, e.g., a fluorescently-labeled antibody or a cell stain such Romanowsky's stain, Leishman stain, May-Grunwald stain, Giemsa stain, Jenner's stain, Wright's stain, or any combination of the same (e.g., Wright-Giemsa stain). Such a stain may comprise eosin Y or eosin B with methylene blue. In certain embodiments, the stain may be an alkaline stain such as haematoxylin.

In some embodiments, the special stains include, but not limited to, Acid fuchsin, Alcian blue 8 GX, Alizarin red S, Aniline blue WS, Auramine O, Azocarmine B, Azocarmine G, Azure A, Azure B, Azure C, Basic fuchsine, Bismarck brown Y, Brilliant cresyl blue, Brilliant green, Carmine, Chlorazol black E, Congo red, C.I. Cresyl violet, Crystal violet, Darrow red, Eosin B, Eosin Y, Erythrosin, Ethyl eosin, Ethyl green, Fast green F C F, Fluorescein Isothiocyanate, Giemsa Stain, Hematoxylin, Hematoxylin & Eosin, Indigo carmine, Janus green B, Jenner stain 1899, Light green SF, Malachite green, Martius yellow, Methyl orange, Methyl violet 2B, Methylene blue, Methylene blue, Methylene violet, (Bernthsen), Neutral red, Nigrosin, Nile blue A, Nuclear fast red, Oil Red, Orange G, Orange II, Orcein, Pararosaniline, Phloxin B, Protargol S, Pyronine B, Pyronine, Resazurin, Rose Bengal, Safranine O, Sudan black B, Sudan III, Sudan IV, Tetrachrome stain (MacNeal), Thionine, Toluidine blue, Weigert, Wright stain, and any combination thereof.

The term "cell viability stains" refers to staining technology used to differentially stain live cells and dead cells inside a tissue sample. Usually the difference in cell membrane and/or nucleus membrane permeability between live and dead cells are taken advantage for the differential staining. In other cases, markers for apoptosis or necrosis (indicating dying cells or cell corpses) are used for such staining.

In some embodiments, the device comprises, on one or both of the plates, a dye to stain the sample for cell viability. In some embodiments, the dye includes, but not limited to, Propidium Iodide (PI), 7-AAD (7-Aminoactinomycin D), Trypan blue, Calcein Violet AM, Calcein AM, Fixable Viability Dye (FVD) conjugated with different fluorophores, SYTO9 and other nucleic acid dyes, Resazurin and Formazan (MTT/XTT) and other mitochondrial dyes, and any combination thereof and the like. In some embodiments, the sample comprises bacteria, and it is desirable to determine the bacterial viability in the sample, the device further comprises, on one or both of the plates, a bacterial viability dye, for instance, PI, SYTO9, and the like, to differentially stain the live cells versus dead cells. Optionally, the device further comprises, on one or both of the plates, dyes for total bacterial staining, for instance, gram staining reagents and the like.

In Situ Hybridization

In some embodiments, the devices and methods of the present invention are useful for conducting in situ hybridization (ISH) on histological samples.

In situ hybridization (ISH) is a type of hybridization that uses a labeled complementary DNA, RNA or modified nucleic acids strand (i.e., probe) to localize a specific DNA or RNA sequence in a portion or section of tissue (in situ), or, if the tissue is small enough (e.g., plant seeds, *Drosophila* embryos), in the entire tissue (whole mount ISH), in cells, and in circulating tumor cells (CTCs).

In situ hybridization is used to reveal the location of specific nucleic acid sequences on chromosomes or in tissues, a crucial step for understanding the organization, regulation, and function of genes. The key techniques currently in use include: in situ hybridization to mRNA with oligonucleotide and RNA probes (both radio-labelled and hapten-labelled); analysis with light and electron microscopes; whole mount in situ hybridization; double detection of RNAs and RNA plus protein; and fluorescent in situ hybridization to detect chromosomal sequences. DNA ISH can be used to determine the structure of chromosomes. Fluorescent DNA ISH (FISH) can, for example, be used in medical diagnostics to assess chromosomal integrity. RNA ISH (RNA in situ hybridization) is used to measure and localize RNAs (mRNAs, lncRNAs, and miRNAs) within tissue sections, cells, whole mounts, and circulating tumor cells (CTCs).

In some embodiments, the detection agent comprises nucleic acid probes for in situ hybridization staining. The nucleic acid probes include, but not limited to, oligonucleotide probes configured to specifically bind to DNA and/or RNA in the sample.

Systems and Methods for Tissue Staining and Cell Imaging

Also provided is a system for rapidly staining and analyzing a tissue sample using a mobile phone, comprising:
(a) sample, staining liquid, and device as described above,
(b) a mobile communication device comprising:
i. one or more cameras for detecting and/or imaging the sample;
ii. electronics, signal processors, hardware and software for receiving and/or processing the detected signal and/or the image of the sample and for remote communication; and
(c) a light source from either the mobile communication device or an external source.

Also provided is a method for rapidly staining and analyzing a tissue sample using a mobile phone, comprising:
(a) depositing a tissue sample and a staining liquid on the device of the system described above, and placing the two plate into a closed configuration;
(b) obtaining a mobile phone that has hardware and software of imaging, data processing, and communication;
(c) assaying by the tissue sample deposited on the CROF device by the mobile phone to generate a result; and
(d) communicating the result from the mobile phone to a location remote from the mobile phone.

Also provided is a method for staining a tissue sample, comprising:
(a) obtaining a tissue sample;
(b) obtaining a stain liquid;
(c) obtaining a first plate and a second plate, wherein:
the plates are movable relative to each other into different configurations;
one or both plates are flexible;
each of the plates has, on its respective surface, a sample contact area for contacting a tissue sample or a IHC staining liquid;
the sample contact area in the first plate is smooth 5 and planner;
the sample contact area in the second plate comprise spacers that are fixed on the surface and have a predetermined substantially uniform height and a predetermined constant inter-spacer distance that is in the range of 7 μm to 200 μm;
(c) depositing the tissue sample and the stain liquid on the plates when the plates are configured in an open configuration, wherein the open configuration is a configuration in which the two plates are either partially or completely separated apart and the spacing between the plates is not regulated by the spacers; and
(d), after (c), using the two plates to compress at least part of the tissue sample and at least part of the staining liquid into a closed configuration;
wherein in the closed configuration: at least part of the sample is between the two plates and a layer of at least part of staining liquid is between the at least part of the sample and the second plate, wherein the thickness of the at least part of staining liquid layer is regulated by the plates, the sample, and the spacers, and has an average distance between the sample surface and the second plate surface is equal or less than 250 μm with a small variation.

All of the benefits and advantages (e.g., an accelerated reaction, faster results, etc.) of other embodiments of QMAX device may be applied to the devices, systems and methods provided for tissue staining.

For example, in some embodiments, the spacers regulating the layer of uniform thickness (i.e., the spacers that are spacing the plates away from each other in the layer) have a "filling factor" of at least 1%, e.g., at least 2% or at least 5%, wherein the filling factor is the ratio of the spacer area that is in contact with the layer of uniform thickness to the total plate area that is in contact with the layer of uniform thickness. In some embodiments, for spacers regulating the layer of uniform thickness, the Young's modulus of the spacers times the filling factor of the spacers is equal or larger than 10 MPa, e.g., at least 15 MPa or at least 20 MPa, where the filling factor is the ratio of the spacer area that is in contact with the layer of uniform thickness to the total plate area that is in contact with the layer of uniform thickness. In some embodiments, the thickness of the flexible plate times the Young's modulus of the flexible plate is in the range of 60 to 550 GPa-μm, e.g., 100 to 300 GPa-μm. In some embodiments, for a flexible plate, the fourth power of the inter-spacer-distance (ISD) divided by the thickness of the flexible plate (h) and the Young's modulus (E) of the flexible plate, $ISD^4/(hE)$, is equal to 5 or less than $10^6$ μm$^3$/GPa, e.g., less than $10^5$ μm$^3$/GPa, less than $10^4$ μm$^3$/GPa or less than $10^3$ μm$^3$/GPa.

In some embodiments, one or both plates comprise a location marker either on a surface of or inside the plate, that provide information of a location of the plate, e.g., a location that is going to be analyzed or a location onto which the section should be deposited. In some cases, one or both plates may comprise a scale marker, either on a surface of or inside the plate, that provides information of a lateral dimension of a structure of the section and/or the plate. In some embodiments, one or both plates comprise an imaging marker, either on surface of or inside the plate, that assists an imaging of the sample. For example, the imaging marker could help focus the imaging device or direct the imaging device to a location on the device. In some embodiments, the spacers can function as a location marker, a scale marker, an imaging marker, or any combination of thereof.

In some embodiments, the inter-spacer distance may substantially periodic. In some cases, the spacers may be in a regular pattern and the spacing between adjacent spacers may be approximately the same. In some embodiments, the spacers are pillars with a cross-sectional shape selected from round, polygonal, circular, square, rectangular, oval, elliptical, or any combination of the same and, in some embodiments, the spacers may have a substantially flat top surface, wherein, for each spacer, the ratio of the lateral dimension of the spacer to its height is at least 1. In some cases, the minimum lateral dimension of spacer is less than or substantially equal to the minimum dimension of an analyte in the sample. The minimum lateral dimension of spacer is in the range of 0.5 μm to 100 μm, e.g., in the range of 2 μm to 50 μm or 0.5 μm to 10 μm.

In some embodiments, the spacers have a pillar shape and the sidewall corners of the spacers have a round shape with a radius of curvature at least 1 µm, e.g., at least 1.2 µm, at least 1.5 µm or at least 2.0 µm. The spacers may have any convenient density, e.g., a density of at least 1,000/mm², e.g., a density of at least 1,000/mm², a density of at least 2,000/mm², a density of at least 5,000/mm² or a density of at least 10,000/mm².

In this device, at least one of the plates may be transparent, thereby allowing the assay to be read optically. Likewise, in this device, at least one of the plates may be made of a flexible polymer, thereby allowing the sample to be efficiently spread by compressing the plates together. In some embodiments, the pressure that compresses the plates, the spacers are not compressible and/or, independently, only one of the plates is flexible. The flexible plate may have a thickness in the range of 20 µm to 200 µm, e.g., 50 µm to 150 µm. As noted above, in the closed position, the thickness of the layer of uniform thickness may have a small variation.

In some embodiments, the variation may be less than 10%, less than 5% or less than 2%, meaning that the thickness of the area does not exceed +/−10%, +/−5% 5 or +/−2% of the average thickness.

In some embodiments, the first and second plates are connected and the device can be changed from the open configuration to the closed configuration by folding the plates. In some embodiments, the first and second plates can be connected by a hinge and the device can be changed from the open configuration to the closed configuration by folding the plates such that the device bends along the hinge. The hinge may be a separate material that is attached to the plates or, in some cases, the plates may be integral with the plates.

In some embodiments, the device may be capable of analyzing the section very rapidly. In some cases, the analysis may be done in 60 seconds or less, in 30 seconds, in 20 seconds or 15 less or in 10 seconds or less.

In some embodiments, the system may additionally comprise (d) a housing configured to hold the sample and to be mounted to the mobile communication device. The housing may comprise optics for facilitating the imaging and/or signal processing of the sample by the mobile communication device, and a mount configured to hold the optics on the mobile communication device. In some cases, an element of the optics of the device (e.g., a lens, filter, mirror, prism or a beamsplitter, may be movable) such that the sample may be imaged in at least two channels.

In some embodiments, the mobile communication device may be configured to communicate test results to a medical professional (e.g., an MD), a medical facility (e.g., a hospital or testing lab) or an insurance company. In addition, the mobile communication device may be configured to communicate information on the subject (e.g., the subject's age, gender, weight, address, name, prior test results, prior medical history, etc.) with the medical professional, medical facility or insurance company. In certain embodiments, the mobile communication device may be configured to receive a prescription, diagnosis or a recommendation from a medical professional. For example, in some embodiments the mobile communication device may send assay results to a remote location where a medical professional gives a diagnosis. The diagnosis may be communicated to the subject via the mobile communication device.

In some embodiments, the mobile communication device may contain hardware and software that allows it to (a) capture an image of the sample; (b) analyze a test location and a control location in in image; and (c) compare a value obtained from analysis of the test location to a threshold value that characterizes the rapid diagnostic test. In some cases, the mobile communication device communicates with the remote location via a wireless or cellular network.

In any embodiment, the mobile communication device may be a mobile phone.

The system may be used in a method that comprises (a) sample on the device of the system; (b) assaying the sample deposited on the device to generate a result; and (c) communicating the result from the mobile communication device to a location remote from the mobile communication device. The method may comprise analyzing the results at the remote location to provide an analyzed result; and communicating the analyzed result from the remote location to the mobile communication device. As noted above, the analysis may be done by a medical professional at a remote location. In some embodiments, the mobile communication device may receive a prescription, diagnosis or a recommendation from a medical professional at a remote location.

Also provided is a method for analyzing a tissue section. In some embodiments, this method may comprise obtaining a device as described above, depositing the section onto one or both plates of the device; placing the plates in a closed configuration and applying an external force over at least part of the plates; and analyzing the sample in the layer of uniform thickness while the plates are the closed configuration.

In some embodiments, this method may comprise:
(a) obtaining a tissue section;
(b) obtaining a first and second plates that are movable relative to each other into different configurations, wherein each plate has a sample contact surface that is substantially planar, one or both plates are flexible, and one or both of the plates comprise spacers that are fixed with a respective sample contacting surface, and wherein the spacers have:
 i. a predetermined substantially uniform height,
 ii. a shape of pillar with substantially uniform cross-section and a flat top surface;
 iii. a ratio of the width to the height equal or larger than one;
 iv. a predetermined constant inter-spacer distance that is in the range of 10 µm to 200 µm;
 v. a filling factor of equal to 1% or larger; and
(c) depositing the section on one or both of the plates when the plates are configured in an open configuration, wherein the open configuration is a configuration in which 5 the two plates are either partially or completely separated apart and the spacing between the plates is not regulated by the spacers;
(d), after (c), using the two plates to compress at least part of the section into a layer of substantially uniform thickness that is confined by the sample contact surfaces of the plates, wherein the uniform thickness of the layer is regulated by the spacers and the plates, and has an average value in the range of 1.8 µm to 3 µm with a variation of less than 10%, wherein the compressing comprises:
bringing the two plates together; and
conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and (e) analyzing the section in the layer of uniform thickness while the plates are the closed configuration;

wherein the filling factor is the ratio of the spacer contact area to the total plate area;

wherein a conformable pressing is a method that makes the pressure applied over an area is substantially constant regardless the shape variation of the outer surfaces of the plates; and wherein the parallel pressing applies the pressures on the intended area at the same time, and a sequential pressing applies the pressure on a part of the intended area and gradually move to other area.

In some embodiments, this method may comprise: removing the external force after the plates are in the closed configuration; imaging the section in the layer of uniform thickness while the plates are the closed configuration. As noted above, in these embodiments, the inter-spacer distance may in the range of 20 µm to 200 µm or 5 µm to 20 µm. In these embodiments, the product of the filling factor and the Young's modulus of the spacer is 2 MPa or larger. In some embodiments, the surface variation is less than 30 nm.

In any of these embodiments, the imaging and counting may be done by: i. illuminating the section in the layer of uniform thickness; ii. taking one or more images of the section using a CCD or CMOS sensor.

In some embodiments, the external force may be provided by human hand, e.g., by pressing down using a digit such as a thumb, or pinching between a thumb and another digit such as a forefinger on the same hand.

In some embodiments, one or more of the plates may comprise a dry reagent coated on one or both plates (e.g., a binding agent, a staining agent, a detection agent or an assay reactant).

In some embodiments, the layer of uniform thickness sample may a thickness uniformity of up to +/−5%, e.g., up to +/−2% or up to +/−1%.

In some embodiments, the spacers are pillars with a cross-sectional shape selected from round, polygonal, circular, square, rectangular, oval, elliptical, or any combination of the same.

Staining and Imaging without a Washing Step and/or in a Single Step

Another aspect of the present invention is to provide devices, systems and methods for staining biological materials (e.g. for staining of cells or tissues, nucleic acid stains, H/E stains, special stains, and/or cell viability stains. etc.) without using washing, and in some embodiments, in a single step.

In some embodiments, by incorporating and/or using a signal amplification surface, the disclosed devices, systems, and methods may facilitate performing assays without washing. The surface amplification surface may only amplify the light emitted in a small distance from the surface (e.g. 20 nm, or 50 nm, or 100 nm). One example of the surface amplification layer is D2PA.

The signal amplification layer amplifies a signal from the target analyte or a label of the target analyte when the target analyte or label is 1 nm, 10 nm, 20 nm, 30 nm, 40 nm, 50 nm, 60 nm, 70 nm, 80 nm, 90 nm, 100 nm, 200 nm, 300 nm, 400 nm, 500 nm, 1 µm, 2 µm, 5 µm, 10 µm from the amplification layer, or a range between any two of the values; and a preferred range of 1 nm to 50 nm, 50 nm to 100 nm, 100 nm to 200 nm, 200 nm to 500 nm.

The term "amplify" refers to an increase in the magnitude of a signal, e.g., at least a 10-fold increase, at least a 100-fold increase at least a 1,000-fold increase, at least a 10,000-fold increase, or at least a 100,000-fold increase in a signal.

In some embodiments, the signal amplification layer includes, but not limited to, the signal amplification layers described in PCT Application (designating U.S.) No. PCT/US2013/032347, which was filed on Mar. 15, 2013, PCT Application (designating U.S.) No. PCT/US2013/062923, which was filed on Oct. 1, 2013, PCT Application (designating U.S.) No. PCT/US2014/030108, which was filed on Mar. 16, 2014, PCT Application (designating U.S.) No. PCT/US2014/029675, which was filed on Mar. 14, 2014, PCT Application (designating U.S.) No. PCT/US2014/028417, which was filed on Mar. 14, 2014, PCT Application (designating U.S.) No. PCT/US2014/029979, which was filed on Mar. 15, 2014, PCT Application (designating U.S.) No. PCT/US2015/056518, which was filed on Oct. 20, 2015, PCT Application (designating U.S.) No. PCT/US2016/054025, which was filed on Sep. 27, 2016, the complete disclosures of which are hereby incorporated by reference for all purposes.

The signal amplification layer comprises a continuous metallic film that is made of a material selected from the group consisting of gold, silver, copper, aluminum, alloys thereof, and combinations thereof. The signal amplification layer comprises high-amplification regions and low-amplification regions, wherein the high-amplification regions amplify signals at said surface more than the low-amplification regions, wherein the low-amplification regions of the layer have been selectively masked, wherein the signal amplification layer comprises (i) two or more protrusions, (ii) two or more metal metallic structures, and (iii) two or more gaps between the metallic structures; thereby increasing the probability that a target analyte will bind to a high-amplification region and be detected.

The signal amplification layer comprising:
(i) a substantially continuous metallic backplane on the substrate;
(ii) one or a plurality of dielectric or semiconductor pillars extending from the metallic backplane or from the substrate through holes in the backplane; and
(iii) a metallic disk on top of the pillar, wherein at least one portion of the edge of the disk is separated from the metallic backplane by a gap;

In some embodiments, the gap(s) and portion of the metal edges are a part of the high signal amplification area, wherein the metallic disk has a shape selected from the group of shapes consisting of round, polygonal, pyramidal, elliptical, elongated bar shaped, or any combination thereof. The metallic disc is separated from the metallic film by a distance in the range of 0.5 to 30 nm, and the average lateral dimension of the discs is in the range of 20 nm to 250 nm; wherein the signal amplification layer comprises one or more metallic discs has a shape selected from the group of shapes consisting of round, polygonal, pyramidal, elliptical, elongated bar shaped, or any combination thereof, wherein the average lateral dimension of the discs is in the range 20 nm to 250 nm, and the gap between adjacent discs in the range of 0.5 to 30 nm.

In some embodiments, the metallic structures are made of a material that is selected from the group consisting of gold, silver, copper, aluminum, alloys thereof, and combinations thereof.

In some embodiments, the pillars are periodic or aperiodic, or the metallic structures have a random shape.

In some embodiments, the signal that is amplified is Raman scattering, chromaticity, luminescence, fluorescence, electro-luminescence, chemiluminescence, and/or electro-chemiluminescence.

Example of Detecting Live and Dead Mammalian Cells.

In this experiment, live and dead white blood cells were detected in QMAX (Q-Cards) within 1 min.

The QMAX device has two plates, first plate and second plate (or X-Plate). The first plate is 1 mm thick PMMA of 24 mm by 32 mm in area. The X-plates were PMMA films of 22 mm by 27 mm in area and 175 µm in thickness, and the spacer arrays on the X-plates had pillar spacers of 30×40 µm in lateral area and 10 µm in height with 80 µm inter-spacer distance.

Propidium iodide solution (Thermo Fisher P3566) and Acridine orange (Thermo Fisher A3568) are used in the experiment to detect viability of mammalian cells. Propidium iodide (PI) is a cell impermeable nucleic acid intercalating dye. However, PI can stain dead cells due to their compromised cell membrane and shows an orange-red color. Acridine orange (AO) can stain both live and dead cells and generate green fluorescent color. When PI and AO are used together, live cells are only stained by AO dye and show green color, while dead cells are stained by both PI and AO dyes, PI can quench AO and shows orange-red color.

Firstly, 100 µg/ml of PI and 20 µg/ml of AO in PBS were prepared. Then, we printed PI/AO dyes solution on an X-plate into an droplet array (16×16, 15 nl volume per droplet) with period of 0.6 mm. The X-plate was aired dried and stored in a vacuumed bag at room temperature. When testing samples, 2.5 ul blood sample was added on the substrate plate and the X-plate was closed and pressed firmly. Incubated the Q-cards (substrate plate and X-plate) for 1 minutes at room temperature. iPhone images were taken using and 6s iPhone with excitation wave length at 470-490 nm and emission 520 nm long pass filter.

Figure 3:
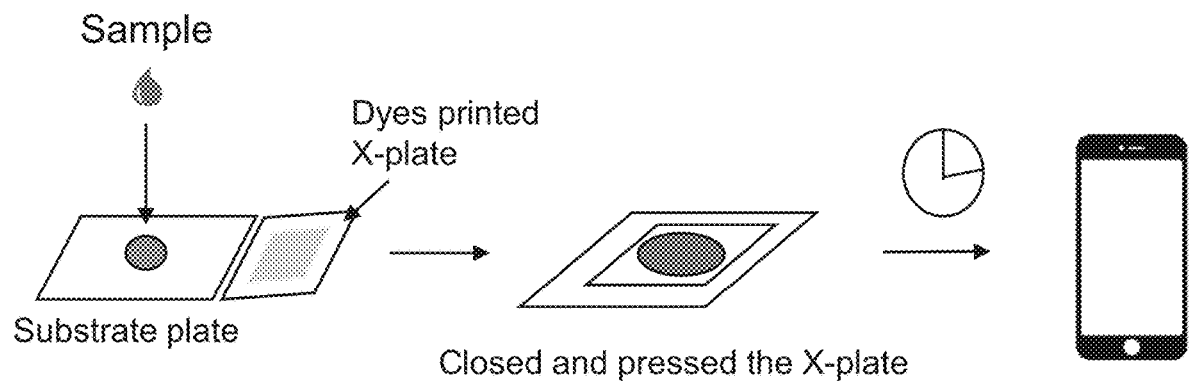
FIG. 3 shows the experiment process that 2.5 µl of fresh blood was added to substrate plate, and the X-plate has PI and AO dyes printed on it. Then, the two plates were pressed together and incubated at room temperature for 1 minute. We collected the data using both microscopy and Phone based microscopy system.

FIG. 3 shows the experiment process that 2.5 µl of fresh blood was added to substrate plate, and the X-plate has PI and AO dyes printed on it. Then, the two plates were pressed together and incubated at room temperature for 1 minute. We collected the data using both microscopy and Phone based microscopy system.

Figure 4:
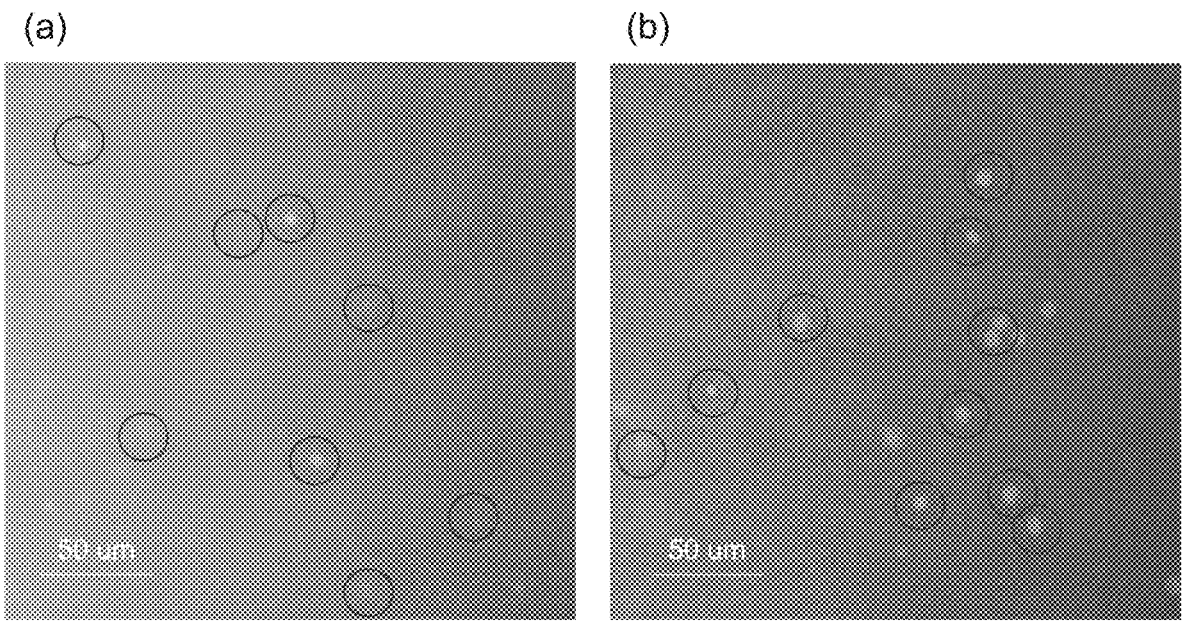
FIG. 4 shows microscope images of live and dead mammalian cells staining. Live cells were stained green marked by blue circles and dead cells were stained orange-red marked by red circles.

FIG. 4 shows microscope images of live and dead mammalian cells staining. Live cells were stained green marked by blue circles and dead cells were stained orange-red marked by red circles.

Figure 5:
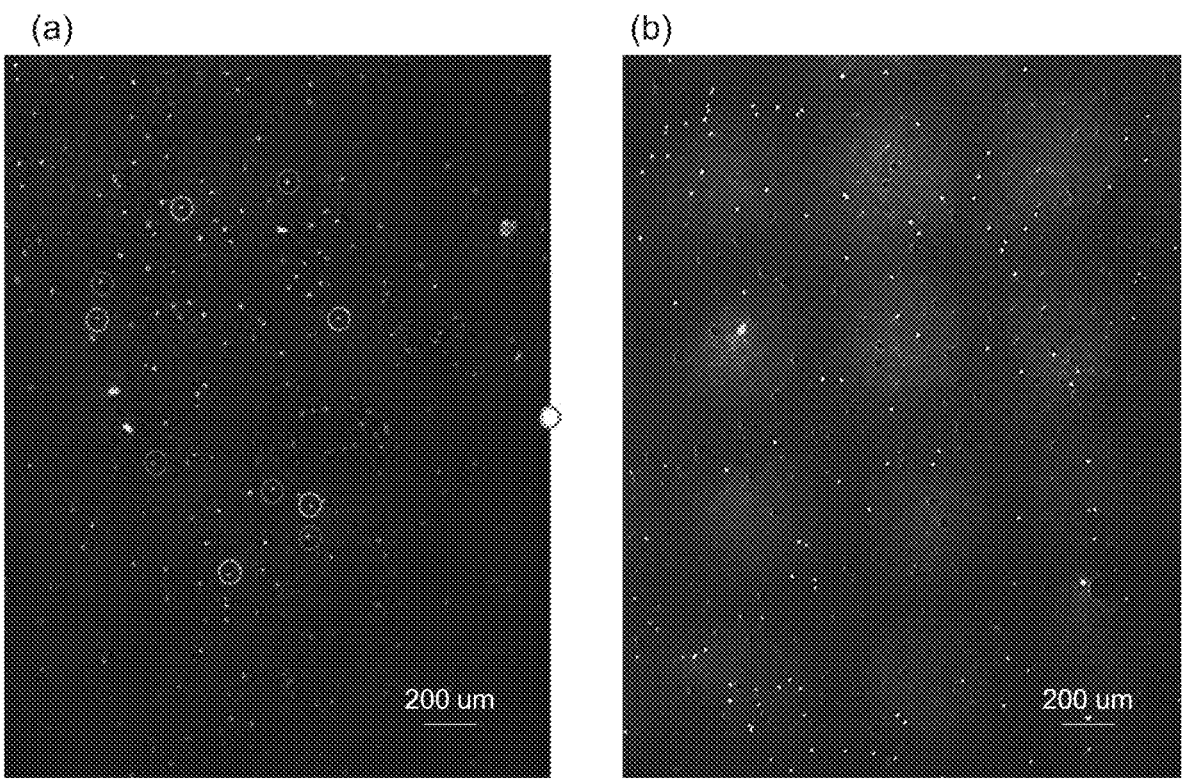
FIG. 5 shows iPhone images of fresh blood samples stained by PI and AO dyes with/without T cells (contained dead cells) spiked. Dead cells were stained orange-red and some were marked by red circles. Live cells were stained green and some were marked by blue circles.

FIG. 5 shows iPhone images of fresh blood samples stained by PI and AO dyes with/without T cells (contained dead cells) spiked. Dead cells were stained orange-red and some were marked by red circles. Live cells were stained green and some were marked by blue circles.

In some embodiments, a cell viability dye selected from the group consisting of: Propidium Iodide, 7-AAD, Trypan blue, Calcein Violet AM, Calcein AM, Fixable Viability Dyes, SYTO9 and other nucleic acid dyes, Resazurin and Formazan (MTT/XTT) and other mitochondrial dyes, sterase substrates, amine-reactive dyes, DAPI, DRAQ7, 7-AAD and TO-PRO-3 and any combination thereof.

In some embodiments, a cell viability dye selected from the group consisting of Protein-binding dyes In some embodiments, dye detecting live cells is selected from Acridine orange, SYTO green nucleic acid stains such as SYTO9, SYTO 11, SYTO 12, SYTO13, SYTO 14, SYTO 16, SYTO 221, SYTO 24, Fluorescein diacetate (FDA), and any combination thereof.

In some embodiments, dye detecting dead cells is selected from Propidium Iodide.

In some embodiments, dye detecting dead cells is selected from Methylene blue.

In some embodiments, dye detecting dead cells is selected from YOYO dye group.

In some embodiments, dye detecting live cells is selected from DiOC2(3), CFDA.

In some embodiments, the sample comprises bacteria, and it is desirable to determine the bacterial viability in the sample, the device further comprises, on one or both of the plates, a bacterial viability dye, for instance, PI, SYTO9, and the like, to differentially stain the live cells versus dead cells. Optionally, the device further comprises, on one or both of the plates, dyes for total bacterial staining, for instance, gram staining reagents and the like.

In some embodiments, dye detecting dead cells is selected from eBioscience™ Fixable Viability Dye eFluor™ 450, eBioscience™ Fixable Viability Dye eFluor™ 506, eBioscience™ Fixable Viability Dye eFluor™ 660, eBioscience™ Fixable Viability Dye eFluor™ 520, eBioscience™ Fixable Viability Dye eFluor™ 780, eBioscience™ Fixable Viability Dye eFluor™ 455UV.

In some embodiments, a cell viability dye selected from the group consisting of LIVE/DEAD™ Fixable Yellow Dead Cell Stain Kit.

In some embodiments, dye detecting live cells is selected from Acridine orange, SYTO green nucleic acid stains such as SYTO9, SYTO 11, SYTO 12, SYTO13, SYTO 14, SYTO 16, SYTO 221, SYTO 24, Fluorescein diacetate (FDA), alamarBlue™ Cell Viability Reagent, Calcein, AM, cell-permeant dye, eBioscience™ Calcein AM Viability Dye, eBioscience™ Calcein Violet 450 AM Viability Dye.

In some embodiments, a cell viability dye selected from the group consisting of LIVE/DEAD Fixable (blue, green, violet, red, near IR, far red) Dead Cell Stain, SYTO™ Orange Fluorescent Nucleic Acid Stain Sampler Kit, SYTO™ Green Fluorescent Nucleic Acid Stain Sampler Kit, SYTO™ Green Fluorescent Nucleic Acid Stain Sampler Kit, LIVE/DEAD™ Fixable Violet Dead Cell Stain Kit, LIVE/DEAD™ Fixable Yellow Dead Cell Stain Kit, Trypan Blue Solution, 0.4%.

Artificial Intelligence and/or Machine Learning for Analysis

In certain embodiments of the present invention, a machine learning framework for QMAX based devices are implemented into a device that is capable of running an algorithms such as deep learning to discriminatively locate, identify, segment and count analytes (e.g. blood cells) based on the pseudo-2D image captured by the QMAX imager.

In certain embodiments of the present invention, the machine learning improves the images captured by the imager on the QMAX device and reduces the effects of noise and artifacts—including and not limited to air bobbles, dusts, shadows, and pillars.

In certain embodiments of the present invention, the training of machine learning uses the spacers of the QMAX card to reduce the data size of training set.

Deep Learning. In certain embodiments, deep learning is used, wherein the analyte detection and localization workflow consists of two stages, training and prediction.

(i) Training Stage.

At the training stage of the present invention, training data with annotation is fed into a convolutional neural network. Convolutional neural network is a specialized neural network for processing data that has a grid-like, feed forward and layered network topology. Examples of the data include time-series data, which can be thought of as a 1D grid taking samples at regular time intervals, and image data, which can be thought of as a 2D grid of pixels. Convolutional networks have been successful in practical applications. The name "convolutional neural network" indicates that the network employs a mathematical operation called convolution. Convolution is a specialized kind of linear operation. Convolutional networks are simply neural networks that use convolution in place of general matrix multiplication in at least one of their layers.

In training the machine learning model in some embodiments of the present invention, it receives one or multiple images of samples that contain the analytes taken by the imager over the sample holding QMAX device as training data. Training data are annotated for analytes to be assayed, wherein the annotations indicate whether or not analytes are in the training data and where they locate in the image. Annotation can be done in the form of tight bounding boxes which fully contains the analyte, or center locations of analytes. In the latter case, center locations are further converted into circles covering analytes or a Gaussian kernel in a point map.

When the size of training data is large, training machine learning model presents two challenges: annotation (usually done by human) is time consuming, and the training is computationally expensive. To overcome these challenges, one can partition the training data into patches of small size, then annotate and train on these patches, or a portion of these patches. The term "machine learning" refers to algorithms, systems and apparatus in the field of artificial intelligence that often use statistical techniques and artificial neural network trained from data without being explicitly programmed.

In some embodiments of the present invention, the annotated images are fed to the machine learning (ML) training module, and the model trainer in the machine learning module will train a ML model from the training data (annotated sample images). The input data will be fed to the model trainer in multiple iterations until certain stopping criterion is satisfied. The output of the ML training module is a ML model—a computational model that is built from a training process in the machine learning from the data that gives computer the capability to perform certain tasks (e.g. detect and classify the objects) on its own.

The trained machine learning model is applied during the predication (or inference) stage by the computer. Examples of machine learning models include ResNet, DenseNet, etc. which are also named as "deep learning models" because of the depth of the connected layers in their network structure. In some embodiments, the Caffe library with fully convolutional network (FCN) was used for model training and predication, and other convolutional neural network architecture and library can also be used, such as TensorFlow.

The training stage generates a model that will be used in the prediction stage. The model can be repeatedly used in the prediction stage for assaying the input. Thus, the computing unit only needs access to the generated model. It does not need access to the training data, nor requiring the training stage to be run again on the computing unit.

(ii) Prediction Stage.

In the predication/inference stage, a detection component is applied to the input image, and an input image is fed into the predication (inference) module preloaded with a trained model generated from the training stage. The output of the prediction stage can be bounding boxes that contain the detected analytes with their center locations or a point map indicating the location of each analyte, or a heatmap that contains the information of the detected analytes.

When the output of the prediction stage is a list of bounding boxes, the number of analytes in the image of the sample for assaying is characterized by the number of detected bounding boxes. When the output of the prediction stage is a point map, the number of analytes in the image of the sample for assaying is characterized by the integration of the point map. When the output of the prediction is a heatmap, a localization component is used to identify the location and the number of detected analytes is characterized by the entries of the heatmap.

One embodiment of the localization algorithm is to sort the heatmap values into a one-dimensional ordered list, from the highest value to the lowest value. Then pick the pixel with the highest value, remove the pixel from the list, along with its neighbors. Iterate the process to pick the pixel with the highest value in the list, until all pixels are removed from the list.

In the detection component using heatmap, an input image, along with the model generated from the training stage, is fed into a convolutional neural network, and the output of the detection stage is a pixel-level prediction, in the form of a heatmap. The heatmap can have the same size as the input image, or it can be a scaled down version of the input image, and it is the input to the localization component. We disclose an algorithm to localize the analyte center. The main idea is to iteratively detect local peaks from the heatmap. After the peak is localized, we calculate the local area surrounding the peak but with smaller value. We remove this region from the heatmap and find the next peak from the remaining pixels. The process is repeated only all pixels are removed from the heatmap.

In certain embodiments, the present invention provides the localization algorithm to sort the heatmap values into a one-dimensional ordered list, from the highest value to the lowest value. Then pick the pixel with the highest value, remove the pixel from the list, along with its neighbors. Iterate the process to pick the pixel with the highest value in the list, until all pixels are removed from the list.

```
Algorithm GlobalSearch (heatmap)
Input:
    heatmap
Output:
    loci
loci ← { }
sort(heatmap)
while (heatmap is not empty) {
    s ← pop(heatmap)
    D ← {disk center as s with radius R}
    heatmap = heatmap \ D // remove D from the heatmap
    add s to loc}
```

After sorting, heatmap is a one-dimensional ordered list, where the heatmap value is ordered from the highest to the lowest. Each heatmap value is associated with its corresponding pixel coordinates. The first item in the heatmap is the one with the highest value, which is the output of the pop(heatmap) function. One disk is created, where the center is the pixel coordinate of the one with highest heatmap value. Then all heatmap values whose pixel coordinates resides inside the disk is removed from the heatmap. The algorithm repeatedly pops up the highest value in the current heatmap, removes the disk around it, till the items are removed from the heatmap.

In the ordered list heatmap, each item has the knowledge of the proceeding item, and the following item. When removing an item from the ordered list, we make the following changes:

Assume the removing item is xr, its proceeding item is xp, and its following item is xf.

For the proceeding item xp, re-define its following item to the following item of the removing item. Thus, the following item of xp is now xf.

For the removing item xr, un-define its proceeding item and following item, which removes it from the ordered list.

For the following item xf, re-define its proceeding item to the proceeding item of the removed item. Thus, the proceeding item of xf is now xp.

After all items are removed from the ordered list, the localization algorithm is complete. The number of elements in the set loci will be the count of analytes, and location information is the pixel coordinate for each s in the set loci.

Another embodiment searches local peak, which is not necessary the one with the highest heatmap value. To detect each local peak, we start from a random starting point, and search for the local maximal value. After we find the peak, we calculate the local area surrounding the peak but with smaller value. We remove this region from the heatmap and find the next peak from the remaining pixels. The process is repeated only all pixels are removed from the heatmap.

```
Algorithm LocalSearch (s, heatmap)
Input:
    s: starting location (x, y)
    heatmap
Output:
    s: location of local peak.
We only consider pixels of value > 0.
Algorithm Cover (s, heatmap)
Input:
    s: location of local peak.
    heatmap:
Output:
    cover: a set of pixels covered by peak:
```

This is a breadth-first-search algorithm starting from s, with one altered condition of visiting points: a neighbor p of the current location q is only added to cover if heatmap[p]>0 and heatmap[p]<=heatmap[q]. Therefore, each pixel in cover has a non-descending path leading to the local peak s.

```
Algorithm Localization (heatmap)
Input:
        heatmap
Output:
        loci
loci ←{ }
pixels←{all pixels from heatmap}
while pixels is not empty {
    s ←any pixel from pixels
    s ←LocalSearch(s, heatmap)       // s is now local peak
    probe local region of radius R surrounding s for better local peak
    r ←Cover(s, heatmap)
    pixels ← pixels \ r       // remove all pixels in cover
    add s to loci
```

In certain embodiments, the image analysis comprising a Combination of Deep Learning and Computer Vision Approach, wherein I the detection and localization are realized by computer vision algorithms, and a classification is realized by deep learning algorithms, wherein the computer vision algorithms detect and locate possible candidates of analytes, and the deep learning algorithm classifies each possible candidate as a true analyte and false analyte. The location of all true analyte (along with the total count of true analytes) will be recorded as the output.

Detection. The computer vision algorithm detects possible candidate based on the characteristics of analytes, including but not limited to intensity, color, size, shape, distribution, etc. A pre-processing scheme can improve the detection. Pre-processing schemes include contrast enhancement, histogram adjustment, color enhancement, de-nosing, smoothing, de-focus, etc. After pre-processing, the input image is sent to a detector. The detector tells the existing of possible candidate of analyte and gives an estimate of its location. The detection can be based on the analyte structure (such as edge detection, line detection, circle detection, etc.), the connectivity (such as blob detection, connect components, contour detection, etc.), intensity, color, shape using schemes such as adaptive thresholding, etc.

Localization After detection, the computer vision algorithm locates each possible candidate of analytes by providing its boundary or a tight bounding box containing it. This can be achieved through object segmentation algorithms, such as adaptive thresholding, background subtraction, floodfill, mean shift, watershed, etc. Very often, the localization can be combined with detection to produce the detection results along with the location of each possible candidates of analytes.

Classification, the deep learning algorithms, such as convolutional neural networks, achieve start-of-the-art visual classification. We employ deep learning algorithms for classification on each possible candidate of analytes. Various convolutional neural network can be utilized for analyte classification, such as VGGNet, ResNet, MobileNet, DenseNet, etc.

Given each possible candidate of analyte, the deep learning algorithm computes through layers of neurons via convolution filters and non-linear filters to extract high-level features that differentiate analyte against non-analytes. A layer of fully convolutional network will combine high-level features into classification results, which tells whether it is a true analyte or not, or the probability of being an analyte.

Dimension of QMAX Card

The thickness, width, and/or length of the two (or more) plates of the QMAX card can be the same or different.

(1) Shape of the Card:

In some embodiments, the shape of the two plates is round, ellipse, rectangle, triangle, polygonal, ring-shaped, or any superposition of these shapes.

In some embodiments, the two (or more) plates of the QMAX card can have the same size and/or shape, or different size and/or shape.

In some embodiments, at least one of the two (or more) plates of the QMAX card has round corners for user safety concerns, wherein the round corners have a diameter of 100 μm or less, 200 μm or less, 500 μm or less, 1 mm or less, 2 mm or less, 5 mm or less, 10 mm or less, 50 mm or less, or in a range between any two of the values.

Generally, the plates can have any shapes, as long as the shape allows a compress open flow of the sample and the regulation of the sample thickness. However, in some embodiments, a particular shape is advantageous.

(2) Thickness of the Card:

The thickness, width, and/or length of the two (or more) plates of the QMAX card can be the same or different.

In some embodiments, the average thickness for at least one of the plates is 2 nm or less, 10 nm or less, 100 nm or less, 200 nm or less, 500 nm or less, 1000 nm or less, 2 μm (micron) or less, 5 μm or less, 10 μm or less, 20 μm or less, 50 μm or less, 100 μm or less, 150 μm or less, 200 μm or less, 300 μm or less, 500 μm or less, 800 μm or less, 1 mm (millimeter) or less, 2 mm or less, 3 mm or less, 5 mm or less, 10 mm or less, 20 mm or less, 50 mm or less, 100 mm or less, 500 mm or less, or in a range between any two of the values.

In some preferred embodiments, the thickness of at least one of the plates is in the range of 0.5 to 1.5 mm;

In some preferred embodiment, the thickness of at least one of the plates is around 1 mm.

In some preferred embodiments, the thickness of at least one of the plates is in the range of 0.15 to 0.2 mm.

In some preferred embodiment, the thickness of at least one of the plates is around 0.175 mm.

In some embodiments, the thickness of any one of the plates is not uniform across the plate. Employing a different plate thickness at different location can be used to control the plate bending, folding, sample thickness regulation, and others.

(3) Area, Width and Length of the Card:

The area of any one of the plates depends on the specific application.

In some embodiments, the area of at least one of the plate is 1 mm$^2$ (square millimeter) or less, 10 mm$^2$ or less, 25 mm$^2$ or less, 50 mm$^2$ or less, 75 mm$^2$ or less, 1 cm$^2$ (square centimeter) or less, 2 cm$^2$ or less, 3 cm$^2$ or less, 4 cm$^2$ or less, 5 cm$^2$ or less, 10 cm$^2$ or less, 100 cm$^2$ or less, 500 cm$^2$ or less, 1000 cm$^2$ or less, 5000 cm$^2$ or less, 10,000 cm$^2$ or less, 10,000 cm$^2$ or less, or in a range between any of the two values.

In some preferred embodiments, the area of at least one plate of the QMAX card is in the range of 500 mm$^2$ to 1,000 mm$^2$;

In some preferred embodiments, the area of one plate is around 600 mm$^2$ and the width of another plate is around 750 mm$^2$.

In some embodiments, the width of at least one of the plates of the QMAX card is 1 mm or less, 5 mm or less, 10 mm or less, 15 mm or less, 20 mm or less, 25 mm or less, 30 mm or less, 35 mm or less, 40 mm or less, 45 mm or less, 50 mm or less, 100 mm or less, 200 mm or less, 500 mm or less, 1000 mm or less, 5000 mm or less, or in a range between any of the two values.

In some preferred embodiments, the width of at least one plate of the QMAX card is in the range of 20 to 30 mm;

In some preferred embodiments, the width of one plate is around 22 mm and the width of another plate is around 24 mm.

In some embodiments, the length of at least one of the plates of the QMAX card is 1 mm or less, 5 mm or less, 10 mm or less, 15 mm or less, 20 mm or less, 25 mm or less, 30 mm or less, 35 mm or less, 40 mm or less, 45 mm or less, 50 mm or less, 100 mm or less, 200 mm or less, 500 mm or less, 1,000 mm or less, 5,000 mm or less, or in a range between any of the two values.

In some preferred embodiments, the length of at least one plate of the QMAX card is in the range of 20 to 40 mm;

In some preferred embodiments, the length of one plate is around 27 mm and the length of another plate is around 32 mm.

(4) Notch:

In some embodiments, there is a notch or multi notches on the inner side of one of the plates for easily peeling up the other plate and separate two plates.

In some embodiments, the shape of the notch is round, ellipse, rectangle, triangle, polygon, ring-shaped, or any superposition of these shapes.

In some embodiments, the size of the notch is 1 mm$^2$ (square millimeter) or less, 10 mm$^2$ or less, 25 mm$^2$ or less, 50 mm$^2$ or less, 75 mm$^2$ or less or in a range between any of the two values.

In some preferred embodiments, the area of the notch on the QMAX card is in the range of 10 to 30 mm$^2$.

In some preferred embodiments, the notch locates at the short width side on the thicker plate.

(5) Trench:

In some embodiments, there one or more trenches on the inner side of one of the plates for preventing overflow or containing preservative/reagent as disclosed herein.

In some embodiments, the trench is open-ended and in a shape such as straight line, curved line, arc, branched tree, or any other shape with open endings. In some embodiments, the trench is in a closed shape. In some embodiments, the shape of the trench is round, ellipse, rectangle, triangle, polygon, ring-shaped, or any superposition of these shapes. The trench can have any possible cross-sectional shape as well, which is either uniform or not uniform.

In some embodiments, the length of the trench is 0.001 mm or less, 0.005 mm or less, 0.01 mm or less, 0.05 mm or less, 0.1 mm or less, 0.5 mm or less, 1 mm or less, 2 mm or less, 5 mm or less, 10 mm or less, 20 mm or less, 50 mm or less, 100 mm or less, or in a range between any two of these values.

In some embodiments, the average cross-sectional area of the trench is 0.001 mm$^2$ or less, 0.005 mm$^2$ or less, 0.01 mm$^2$ or less, 0.05 mm$^2$ or less, 0.1 mm$^2$ or less, 0.5 mm$^2$ or less, 1 mm$^2$ or less, 2 mm$^2$ or less, 5 mm$^2$ or less, 10 mm$^2$ or less, 20 mm$^2$ or less, or in a range between any two of these values.

(6) Receptacle Slot:

In some embodiments, the receiving area of the receptacle slot, or the lateral area covered by the sliding track has an area larger or equal as the area of the QMAX device.

In some embodiments, the shape of the receiving area of the receptacle slot is round, ellipse, rectangle, triangle, polygon, ring-shaped, or any superposition of these shapes;

In some embodiments, the average gap size of the sliding track is larger than the average thickness of the device by 100 nm, 500 nm, 1 µm, 2 µm, 5 µm, 10 µm, 50 µm, 100 µm, 300 µm, 500 µm, 1 mm, 2 mm, 5 mm, 1 cm, or in a range between any two of the values.

In some preferred embodiments, the average gap size of the slot is larger than the average thickness of the device by 50 µm to 300 µm.

In some embodiments, the receiving area of the receptacle slot is larger than the area of the device by 1 mm$^2$ (square millimeter) or less, 10 mm$^2$ or less, 25 mm$^2$ or less, 50 mm$^2$ or less, 75 mm$^2$ or less, 1 cm$^2$ (square centimeter) or less, 2 cm$^2$ or less, 3 cm$^2$ or less, 4 cm$^2$ or less, 5 cm$^2$ or less, 10 cm$^2$ or less, 100 cm$^2$ or less, or in a range between any of the two values.

In some embodiments, the shape of one of the plates or both of the plates is the same as the shape of the receptacle slot.

In some embodiments, the QMAX device is only partially inside the receptacle slot at best when they are fully engaged, the shape of part of one of the plates or both of the plates is the same as the shape of the receptacle slot.

(7) Others:

In some embodiments, at least one of the plate is in the form of a belt (or strip) that has a width, thickness, and length. In some embodiments, the width is at most 0.1 cm (centimeter), at most 0.5 cm, at most 1 cm, at most 5 cm, at most 10 cm, at most 50 cm, at most 100 cm, at most 500 cm, at most 1,000 cm, or in a range between any two of the values. The length is as long it needed. In some embodiments, the belt is rolled into a roll.

(8) Disposable Cards

In some embodiments, it is a significant advantage of the present invention that the disclosed QMAX cards are made of inexpensive materials and manufactured with low cost, therefore the economic burden to the user is at relatively low level.

In some embodiments, the QMAX cards are configured to be disposable after one-time use.

In some embodiments, the QMAX cards are configured to be environmentally safe and therefore its disposal does not need special treatment. In one aspect, none of the materials for a basic QMAX card (the plates and/or the hinge) as provided herein in some embodiments, are known to be toxic or dangerous to human beings or the environment. In another aspect, the round corner designed for the plates in some embodiments are particularly useful for avoiding unintentional stabbing or slashing injury either to the user or to other people that may have exposure to them, including trash collectors. Moreover, the overflow prevention mechanism in certain embodiments are useful for preventing the unintentional contact with or exposure to the biological and/or chemical sensitive sample material that is deposited in between the plates.

Examples of Present Invention

Device

In certain embodiments of the present invention, a device for analyzing a tissue sample, comprises a first plate, a second plate, and spacers. In certain embodiments, the plates are movable relative to each other into different configurations. In certain embodiments, one or both plates are flexible. In certain embodiments, each of the plates has, on its respective inner surface, a sample contact area for contacting a staining liquid and/or a tissue sample suspected of containing a target analyte. In certain embodiments, one or both of the plates comprise the spacers that are fixed with a respective plate. In certain embodiments, the spacers have a predetermined substantially uniform height and a predetermined inter-spacer distance. In certain embodiments, at least one of the spacers is inside the sample contact area. In certain embodiments, one of the configurations is an open configuration, in which: the two plates are partially or entirely separated apart, the spacing between the plates is not regulated by the spacers, and the staining liquid and the sample are deposited on one or both of the plates. In certain embodiments, another of the configurations is a closed configuration, which is configured after the deposition of the staining liquid and the sample in the open configuration, and in the closed configuration: at least part of the sample is between the two plates and a layer of at least part of staining liquid is between the at least part of the sample and the second plate, wherein the thickness of the at least part of staining liquid layer is regulated by the plates, the sample, and the spacers, and has an average distance between the sample surface and the second plate surface is equal to or less than 250 μm with a small variation.

In certain embodiments of the present invention, a device for analyzing a tissue sample, comprises a first plate, a second plate, and spacers. In certain embodiments, the plates are movable relative to each other into different configurations. In certain embodiments, one or both plates are flexible. In certain embodiments, each of the plates has, on its respective inner surface, a sample contact area for contacting a transfer solution and/or a tissue sample suspected of containing a target analyte. In certain embodiments, one or both of the plates comprise stain agent that is coated on the respective sample contact area and configured to, upon contacting the transfer solution, be dissolved in the transfer solution and stain the tissue sample. In certain embodiments, one or both of the plates comprise the spacers that are fixed with a respective plate. In certain embodiments, the spacers have a predetermined substantially uniform height and a predetermined inter-spacer distance. In certain embodiments, at least one of the spacers is inside the sample contact area. In certain embodiments, one of the configurations is an open configuration, in which: the two plates are partially or entirely separated apart, the spacing between the plates is not regulated by the spacers, and the staining liquid and the sample are deposited on one or both of the plates. In certain embodiments, another of the configurations is a closed configuration, which is configured after the deposition of the staining liquid and the sample in the open configuration, and in the closed configuration: at least part of the sample is between the two plates and a layer of at least part of transfer solution is between the at least part of the sample and the second plate, wherein the thickness of the at least part of transfer solution layer is regulated by the plates, the sample, and the spacers, and has an average distance between the sample surface and the second plate surface is equal to or less than 250 μm with a small variation.

Method

In certain embodiments of the present invention, a method for analyzing a tissue sample, comprises obtaining a tissue sample suspected of containing a target analyte and a staining liquid, obtaining a first plate, a second plate, and spacers, depositing the staining liquid and the tissue sample on one or both of the plates when the plates are in an open configuration, bringing the two plates together and pressing the plates into a closed configuration, and analyzing the target analyte when the plates are in the closed configuration. In certain embodiments, the plates are movable relative to each other into different configurations. In certain embodiments, one or both plates are flexible. In certain embodiments, each of the plates has, on its respective inner surface, a sample contact area for contacting the staining liquid and/or the tissue sample. In certain embodiments, one or both of the plates comprise the spacers that are fixed with a respective plate. In certain embodiments, the spacers have a predetermined substantially uniform height and a predetermined inter-spacer distance. In certain embodiments, and at least one of the spacers is inside the sample contact area. In certain embodiments, the open configuration is a configuration in which the two plates are partially or entirely separated apart, the spacing between the two plates is not regulated by the spacers, and the sample and the staining liquid are deposited on one or both of the plates. In certain embodiments, the pressing comprises conformable pressing, either in parallel or sequentially, an area of at least one of the plates to press the plates together to the closed configuration, wherein the conformable pressing generates a substantially uniform pressure on the plates over the at least part of the sample, and the pressing spreads the at least part of the sample laterally between the inner surfaces of the plates. In certain embodiments, another of the configurations is the closed configuration, which is configured after the deposition of the staining liquid and the sample in the open configuration, and in the closed configuration: at least part of the sample is between the two plates and a layer of at least part of staining liquid is between the at least part of the sample and the second plate, wherein the thickness of the at least part of staining liquid layer is regulated by the plates, the sample, and the spacers, and has an average distance between the sample surface and the second plate surface is equal to or less than 250 µm with a small variation.

In certain embodiments of the present disclosure, a method for analyzing a tissue sample, comprising the steps of obtaining a tissue sample suspected of containing a target analyte and a transfer solution, obtaining a first plate, a second plate, and spacers, depositing the staining liquid and the tissue sample on one or both of the plates when the plates are in an open configuration, bringing the two plates together and pressing the plates into a closed configuration, and analyzing the target analyte when the plates are in the closed configuration. In certain embodiments, the plates are movable relative to each other into different configurations. In certain embodiments, one or both plates are flexible. In certain embodiments, each of the plates has, on its respective inner surface, a sample contact area for contacting a staining liquid and/or a tissue sample suspected of containing a target analyte. In certain embodiments, one or both of the plates comprise stain agents that are coated on the respective sample contact area and configured to, upon contacting a transfer solution, be dissolved in the transfer solution and stain the tissue sample. In certain embodiments, one or both of the plates comprise the spacers that are fixed with a respective plate. In certain embodiments, the spacers have a predetermined substantially uniform height and a predetermined inter-spacer distance. In certain embodiments, at least one of the spacers is inside the sample contact area. In certain embodiments, the open configuration is a configuration in which the two plates are partially or entirely separated apart, the spacing between the two plates is not regulated by the spacers, and the sample and the staining liquid are deposited on one or both of the plates. In certain embodiments, the pressing comprises conformable pressing, either in parallel or sequentially, an area of at least one of the plates to press the plates together to the closed configuration, wherein the conformable pressing generates a substantially uniform pressure on the plates over the at least part of the sample, and the pressing spreads the at least part of the sample laterally between the inner surfaces of the plates. In certain embodiments, another of the configurations is the closed configuration, which is configured after the deposition of the staining liquid and the sample in the open configuration, and in the closed configuration: at least part of the sample is between the two plates and a layer of at least part of staining liquid is between the at least part of the sample and the second plate, wherein the thickness of the at least part of staining liquid layer is regulated by the plates, the sample, and the spacers, and has an average distance between the sample surface and the second plate surface is equal to or less than 250 µm with a small variation.

In certain embodiments of the present invention, a method for analyzing a tissue sample, comprises the steps of obtaining a tissue sample suspected of containing a target analyte and a transfer solution, obtaining a first plate, a second plate, and spacers, depositing the staining liquid and the tissue sample on one or both of the plates when the plates are in an open configuration, bringing the two plates together and pressing the plates into a closed configuration, and without washing, analyzing the target analyte when the plates are in the closed configuration. In certain embodiments, the plates are movable relative to each other into different configurations. In certain embodiments, one or both plates are flexible. In certain embodiments, each of the plates has, on its respective inner surface, a sample contact area for contacting a staining liquid and/or a tissue sample suspected of containing a target analyte. In certain embodiments, one or both of the plates comprise stain agents that are coated on the respective sample contact area and configured to, upon contacting a transfer solution, be dissolved in the transfer solution and stain the tissue sample. In certain embodiments, one or both of the plates comprise the spacers that are fixed with a respective plate. In certain embodiments, the spacers have a predetermined substantially uniform height and a predetermined inter-spacer distance. In certain embodiments, at least one of the spacers is inside the sample contact area. In certain embodiments, the open configuration is a configuration in which the two plates are partially or entirely separated apart, the spacing between the two plates is not regulated by the spacers, and the sample and the staining liquid are deposited on one or both of the plates. In certain embodiments, in the pressing comprises conformable pressing, either in parallel or sequentially, an area of at least one of the plates to press the plates together to the closed configuration, wherein the conformable pressing generates a substantially uniform pressure on the plates over the at least part of the sample, and the pressing spreads the at least part of the sample laterally between the inner surfaces of the plates. In certain embodiments, another of the configurations is the closed configuration, which is configured after the deposition of the staining liquid and the sample in the open configuration, and in the closed configuration at least part of the sample is between the two plates and a layer of at least part of staining liquid is between the at least part of the sample and the second plate, wherein the thickness of the at least part of staining liquid layer is regulated by the plates, the sample, and the spacers, and has an average distance between the sample surface and the second plate surface is equal to or less than 250 µm with a small variation.

System:

In certain embodiments of the present invention, a system for analyzing a tissue sample, comprises a device of any prior embodiment and a detector that detects signals of the analyte in the layer of uniform thickness.

Smartphone System:

In certain embodiments of the present invention, a smartphone system for rapid homogeneous assay, comprises a device of any prior embodiment, and a mobile communication device. In certain embodiments, the mobile communication device comprises one or a plurality of cameras for detecting and/or imaging the sample, electronics, signal processors, hardware and software for receiving and/or processing the detected signal and/or the image of the sample and for remote communication, and an adaptor that is configured to accommodate the device that is in the closed configuration and be engageable to the mobile communication device. In certain embodiments, when engaged with the mobile communication device, the adaptor is configured to facilitate the detection and/or imaging of the analyte in the sample at the closed configuration.

In certain embodiments, the one or both of the plates can be configured such that the sample can be dried thereon at the open configuration, and wherein the sample comprises bodily fluid selected from the group consisting of: amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, urine, and any combination thereof.

In certain embodiments, the staining liquid can have a viscosity in the range of 0.1 to 3.5 mPa S.

In certain embodiments, the sample contact area of one or both of the plates can be configured such that the sample can be dried thereon at the open configuration, and wherein the sample comprises blood smear and is dried on one or both plates.

In certain embodiments, the sample contact area of one or both of the plates can be adhesive to the sample, and wherein the sample is a tissue section having a thickness in the range of 1 μm-200 μm.

In certain embodiments, the sample can be paraffin-embedded.

In certain embodiments, the sample can be fixed.

In certain embodiments, the staining liquid can comprise a fixative capable of fixing the sample.

In certain embodiments, the staining liquid can comprise blocking agents, wherein the blocking agents are configured to disable non-specific endogenous species in the sample to react with detection agents that are used to specifically label the target analyte.

In certain embodiments, the staining liquid can comprise deparaffinizing agents capable of removing paraffin in the sample.

In certain embodiments, the staining liquid can comprise permeabilizing agents capable of permeabilizing cells in the tissue sample that contain the target analyte.

In certain embodiments, the staining liquid can comprise antigen retrieval agents capable of facilitating retrieval of antigen.

In certain embodiments, the staining liquid can comprise detection agents that specifically label the target analyte in the sample.

In certain embodiments, the sample contact area of one or both plates can comprise a storage site that contains blocking agents, wherein the blocking agents are configured to disable non-specific endogenous species in the sample to react with detection agents that are used to specifically label the target analyte.

In certain embodiments, the sample contact area of one or both plates comprise a storage site that contains deparaffinizing agents capable of removing paraffin in the sample.

In certain embodiments, the sample contact area of one or both plates can comprise a storage site that contains permeabilizing agents capable of permeabilizing cells in the tissue sample that contain the target analyte.

In certain embodiments, the sample contact area of one or both plates can comprise a storage site that contains antigen retrieval agents capable of facilitating retrieval of antigen.

In certain embodiments, the sample contact area of one or both plates comprise a storage site that contains detection agents that specifically label the target analyte in the sample.

In certain embodiments, the detection agent comprises dyes for a stain selected from the group consisting of Acid fuchsin, Alcian blue 8 GX, Alizarin red S, Aniline blue WS, Auramine O, Azocarmine B, Azocarmine G, Azure A, Azure B, Azure C, Basic fuchsine, Bismarck brown Y, Brilliant cresyl blue, Brilliant green, Carmine, Chlorazol black E, Congo red, C.I. Cresyl violet, Crystal violet, Darrow red, Eosin B, Eosin Y, Erythrosin, Ethyl eosin, Ethyl green, Fast green F C F, Fluorescein Isothiocyanate, Giemsa Stain, Hematoxylin, Hematoxylin & Eosin, Indigo carmine, Janus green B, Jenner stain 1899, Light green SF, Malachite green, Martius yellow, Methyl orange, Methyl violet 2B, Methylene blue, Methylene blue, Methylene violet, (Bernthsen), Neutral red, Nigrosin, Nile blue A, Nuclear fast red, Oil Red, Orange G, Orange II, Orcein, Pararosaniline, Phloxin B, Protargol S, Pyronine B, Pyronine, Resazurin, Rose Bengal, Safranine O, Sudan black B, Sudan III, Sudan IV, Tetrachrome stain (MacNeal), Thionine, Toluidine blue, Weigert, Wright stain, and any combination thereof.

In certain embodiments, one or both of the plates can further comprise, on the respective sample contact area, cell viability dye selected from the group consisting of: Propidium Iodide, 7-AAD, Trypan blue, Calcein Violet AM, Calcein AM, Fixable Viability Dyes, SYTO9 and other nucleic acid dyes, Resazurin and Formazan (MTT/XTT) and other mitochondrial dyes, and any combination thereof.

In certain embodiments, the detection agent comprises antibodies configured to specifically bind to protein analyte in the sample.

In certain embodiments, the detection agent can comprise oligonucleotide probes configured to specifically bind to DNA and/or RNA in the sample.

In certain embodiments, the detection agent is labeled with a reporter molecule, wherein the reporter molecule is configured to provide a detectable signal to be read and analyzed.

In certain embodiments, the signal can be selected from the group consisting of luminescence selected from photoluminescence, electroluminescence, and electrochemiluminescence, light absorption, reflection, transmission, diffraction, scattering, or diffusion, surface Raman scattering, electrical impedance selected from resistance, capacitance, and inductance, magnetic relaxivity; and any combination thereof.

In certain embodiments, the sample contact area of one or both of the plates can comprise a binding site that contains capture agents, wherein the capture agents are configured to bind to the target analyte on the surface of cells in the sample and immobilize the cells.

In certain embodiments, the depositing step (c) can comprise depositing and drying the sample on one or both of the plates before depositing the remaining of the staining liquid on top of the dried sample, and wherein the sample comprises blood smear and is dried on one or both plates.

In certain embodiments, the depositing step (c) can comprise depositing and attaching the sample to one or both of the plates before depositing the staining liquid on top of the sample, wherein the sample contact area of one or both of the plates is adhesive to the sample, and wherein the sample is a tissue section having a thickness in the range of 1 μm-200 μm.

In certain embodiments, before step (e), the method can include the step of incubating the sample at the closed configuration for a period of time that is longer than the time it takes for the detection agent to diffuse across the layer of uniform thickness and the sample.

In certain embodiments, before step (e), the method can further comprise the step of incubating the sample at the closed configuration at a predetermined temperature in the range of 30-75° C.

In certain embodiments, the staining liquid can comprise the transfer solution.

In certain embodiments, the mobile communication device can be configured to communicate test results to a medical professional, a medical facility or an insurance company.

In certain embodiments, the mobile communication device can be further configured to communicate information on the subject with the medical professional, medical facility or insurance company.

In certain embodiments, the mobile communication device can be configured to receive a prescription, diagnosis or a recommendation from a medical professional.

In certain embodiments, the mobile communication device can communicate with the remote location via a Wi-Fi or cellular network.

In certain embodiments, the mobile communication device can be a mobile phone.

In certain embodiments, in the device that comprises the two plates and spacers, the pressing can be by a human hand.

In certain embodiments, in the device that comprises the two plates and spacers, at least a portion of the inner surface of one plate or both plates can be hydrophilic.

In certain embodiments, in the device that comprises two plates and spacers, the inter spacer distance can be periodic.

In certain embodiments, in the device that comprises two plates and spacers, the sample can be a deposition directly from a subject to the plate without using any transferring devices.

In certain embodiment, in the device that comprises two plates and spacers, after the sample deformation is in the closed configuration, the sample maintains the same final sample thickness, when some or all of the compressing forces are removed.

In certain embodiments, in the device that comprises two plates and spacers, the spacers can have pillar shape and nearly uniform cross-section.

In certain embodiments, in the device that comprises two plates and spacers, the inter spacer distance (ISD) can be equal to or less than about 120 μm (micrometer).

In certain embodiments, in the device that comprises two plates and spacers, the inter spacer distance (ISD) is equal or less than about 100 μm (micrometer).

In certain embodiments, in the device that comprises two plates and spacers, the fourth power of the inter-spacer-distance (ISD) divided by the thickness (h) and the Young's modulus (E) of the flexible plate ($ISD^4/(hE)$) is $5\times10^6$ μm³/GPa or less.

In certain embodiments, in the device that comprises two plates and spacers, wherein the fourth power of the inter-spacer-distance (ISD) divided by the thickness (h) and the Young's modulus (E) of the flexible plate ($ISD^4/(hE)$) is $5\times10^5$ μm³/GPa or less.

In certain embodiments, in the device that comprises two plates and spacers, the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height can be at least 1 (one).

In certain embodiments, in the device that comprises two plates and spacers, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one), wherein the fourth power of the inter-spacer-distance (ISD) divided by the thickness (h) and the Young's modulus (E) of the flexible plate ($ISD^4/(hE)$) can be $5\times10^6$ μm³/GPa or less.

In certain embodiments, the ratio of the inter-spacing distance of the spacers to the average width of the spacer can be 2 or larger, and the filling factor of the spacers multiplied by the Young's modulus of the spacers can be 2 MPa or larger.

In certain embodiments, the analyte can be the analyte in detection of proteins, peptides, nucleic acids, synthetic compounds, and inorganic compounds.

In certain embodiments, the sample can be a biological sample selected from amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, and urine.

In certain embodiments, the spacers can have a shape of pillars and a ratio of the width to the height of the pillar can be equal or larger than one.

In certain embodiments, the sample that is deposited on one or both of the plates can have an unknown volume.

In certain embodiments the spacers can have a shape of pillar, and the pillar can have a substantially uniform cross-section.

In certain embodiments, the samples can be for the detection, purification and quantification of chemical compounds or biomolecules that correlates with the stage of certain diseases.

In certain embodiments, the samples can be related to infectious and parasitic disease, injuries, cardiovascular disease, cancer, mental disorders, neuropsychiatric disorders, pulmonary diseases, renal diseases, and other and organic diseases.

In certain embodiments, the samples can be related to the detection, purification and quantification of microorganism.

In certain embodiments, the samples can be related to virus, fungus and bacteria from environment, e.g., water, soil, or biological samples.

In certain embodiments, the samples is related to the detection, quantification of chemical compounds or biological samples that pose hazard to food safety or national security, e.g. toxic waste, anthrax.

In certain embodiments, the samples are related to quantification of vital parameters in medical or physiological monitor.

In certain embodiments, the samples are related to glucose, blood, oxygen level, total blood count.

In certain embodiments, the samples are related to the detection and quantification of specific DNA or RNA from biosamples.

In certain embodiments, the samples are related to the sequencing and comparing of genetic sequences in DNA in the chromosomes and mitochondria for genome analysis.

In certain embodiments, the samples are related to detect reaction products, e.g., during synthesis or purification of pharmaceuticals.

In certain embodiments, the samples are cells, tissues, bodily fluids, and stool.

In certain embodiments, the sample is the sample in the detection of proteins, peptides, nucleic acids, synthetic compounds, inorganic compounds.

In certain embodiments, the sample is the sample in the fields of human, veterinary, agriculture, foods, environments, and drug testing.

In certain embodiments, the sample is a biological sample is selected from blood, serum, plasma, a nasal swab, a nasopharyngeal wash, saliva, urine, gastric fluid, spinal fluid, tears, stool, mucus, sweat, earwax, oil, a glandular secretion, cerebral spinal fluid, tissue, semen, vaginal fluid, interstitial fluids derived from tumorous tissue, ocular fluids, spinal fluid, a throat swab, breath, hair, finger nails, skin, biopsy, placental fluid, amniotic fluid, cord blood, lymphatic fluids, cavity fluids, sputum, pus, microbiota, meconium, breast milk, exhaled condensate nasopharyngeal wash, nasal swab, throat swab, stool samples, hair, finger nail, ear wax, breath, connective tissue, muscle tissue, nervous tissue, epithelial tissue, cartilage, cancerous sample, or bone.

Device and Assay with High Uniformity

Sample Viscosity

In the present invention, the samples to be manipulated and/or analyzed can have a various range of viscosities. For examples, the typical viscosity range is 1.31 to 0.28 (mPa s) from 10 to 100° C. for water; 1.05 to 0.70 (mPa s) from 19 to 37° C. for PBS buffer; 2.4 to 1.45 (mPa s) from 17 to 45° C. for plasma; 2.87 to 2.35 (mPa s) from 35 to 42° C. for whole blood; and 0.797 to 0.227 (mPa s) from 0 to 100° C. for methanol. In some embodiments, the sample has a viscosity from 0.1 to 4 (mPa s). In some embodiments, the sample has viscosity of from 4 to 50 (mPa s). In a preferred embodiment, the sample has viscosity of from 0.5 to 3.5 (mPa s).

Flat Top of Pillar Spacers

In certain embodiments of the present invention, the spacers are pillars that have a flat top and a foot fixed on one plate, wherein the flat top has a smoothness with a small surface variation, and the variation is less than 5, 10 nm, 20 nm, 30 nm, 50 nm, 100 nm, 200 nm, 300 nm, 400 nm, 500 nm, 600 nm, 700 nm, 800 nm, 1000 nm, or in a range between any two of the values. A preferred flat pillar top smoothness is that surface variation of 50 nm or less.

Furthermore, the surface variation is relative to the spacer height and the ratio of the pillar flat top surface variation to the spacer height is less than 0.5%, 1%, 3%, 5%, 7%, 10%, 15%, 20%, 30%, 40%, or in a range between any two of the values. A preferred flat pillar top smoothness has a ratio of the pillar flat top surface variation to the spacer height is less than 2%, 5%, or 10%.

Sidewall Angle of Pillar Spacers

In certain embodiments of the present invention, the spacers are pillars that have a sidewall angle. In some embodiments, the sidewall angle is less than 5 degree (measured from the normal of a surface), 10 degree, 20 degree, 30 degree, 40 degree, 50 degree, 70 degree, or in a range between any two of the values. In a preferred embodiment, the sidewall angle is less 5 degree, 10 degree, or 20 degree.

Formation of Uniform Thin Fluidic Layer by an Imprecise Force Pressing

In certain embodiment of the present invention, a uniform thin fluidic sample layer is formed by using a pressing with an imprecise force. The term "imprecise pressing force" without adding the details and then adding a definition for imprecise pressing force. As used herein, the term "imprecise" in the context of a force (e.g. "imprecise pressing force") refers to a force that (a) has a magnitude that is not precisely known or precisely predictable at the time the force is applied; (b) has a pressure in the range of 0.01 kg/cm$^2$ (centimeter square) to 100 kg/cm$^2$, (c) varies in magnitude from one application of the force to the next; and (d) the imprecision (i.e. the variation) of the force in (a) and (c) is at least 20% of the total force that actually is applied.

An imprecise force can be applied by human hand, for example, e.g., by pinching an object together between a thumb and index finger, or by pinching and rubbing an object together between a thumb and index finger.

In some embodiments, the imprecise force by the hand pressing has a pressure of 0.01 kg/cm2, 0.1 kg/cm2, 0.5 kg/cm2, 1 kg/cm2, 2 kg/cm2, kg/cm2, 5 kg/cm2, 10 kg/cm2, 20 kg/cm2, 30 kg/cm2, 40 kg/cm2, 50 kg/cm2, 60 kg/cm2, 100 kg/cm2, 150 kg/cm2, 200 kg/cm2, or a range between any two of the values; and a preferred range of 0.1 kg/cm2 to 0.5 kg/cm2, 0.5 kg/cm2 to 1 kg/cm2, 1 kg/cm2 to 5 kg/cm2, 5 kg/cm2 to 10 kg/cm2 (Pressure).

Spacer Filling Factor.

The term "spacer filling factor" or "filling factor" refers to the ratio of the spacer contact area to the total plate area", wherein the spacer contact area refers, at a closed configuration, the contact area that the spacer's top surface contacts to the inner surface of a plate, and the total plate area refers the total area of the inner surface of the plate that the flat top of the spacers contact. Since there are two plates and each spacer has two contact surfaces each contacting one plate, the filling fact is the filling factor of the smallest.

For example, if the spacers are pillars with a flat top of a square shape (10 μm×10 μm), a nearly uniform cross-section and 2 μm tall, and the spacers are periodic with a period of 100 μm, then the filing factor of the spacer is 1%. If in the above example, the foot of the pillar spacer is a square shape of 15 μm×15 μm, then the filling factor is still 1% by the definition.

IDS$^4$/hE

A device for forming a thin fluidic sample layer with a uniform predetermined thickness by pressing, comprising:
 a first plate, a second plate, and spacers, wherein:
  i. the plates are movable relative to each other into different configurations;
  ii. one or both plates are flexible;
  iii. each of the plates comprises an inner surface that has a sample contact area for contacting a fluidic sample;
  iv. each of the plates comprises, on its respective outer surface, a force area for applying an pressing force that forces the plates together;
  v. one or both of the plates comprise the spacers that are permanently fixed on the inner surface of a respective plate;
  vi. the spacers have a predetermined substantially uniform height that is equal to or less than 200 microns, and a predetermined fixed inter-spacer-distance;
  vii. the fourth power of the inter-spacer-distance (ISD) divided by the thickness (h) and the Young's modulus (E) of the flexible plate (ISD$^4$/(hE)) is 5×10$^6$ μm$^3$/GPa or less; and
  viii. at least one of the spacers is inside the sample contact area;
 wherein one of the configurations is an open configuration, in which: the two plates are partially or completely separated apart, the spacing between the plates is not regulated by the spacers, and the sample is deposited on one or both of the plates;
 wherein another of the configurations is a closed configuration which is configured after the sample is deposited in the open configuration and the plates are forced to the closed configuration by applying the pressing force on the force area; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers.

A method of forming a thin fluidic sample layer with a uniform predetermined thickness by pressing, comprising the steps of:
(a) obtaining a device of any prior embodiment;
(b) depositing a fluidic sample on one or both of the plates; when the plates are configured in an open configuration, wherein the open configuration is a configuration in which the two plates are partially or completely separated apart and the spacing between the plates is not regulated by the spacers;
(c) after (b), forcing the two plates into a closed configuration, in which: at least part of the sample is compressed by the two plates into a layer of substantially uniform thickness, wherein the uniform thickness of the layer is confined by the sample contact surfaces of the plates and is regulated by the plates and the spacers.

A device for analyzing a fluidic sample, comprising:
a first plate, a second plate, and spacers, wherein:
i. the plates are movable relative to each other into different configurations;
ii. one or both plates are flexible;
iii. each of the plates has, on its respective inner surface, a sample contact area for contacting a fluidic sample,
iv. one or both of the plates comprise the spacers and the spacers are fixed on the inner surface of a respective plate;
v. the spacers have a predetermined substantially uniform height that is equal to or less than 200 microns, and the inter-spacer-distance is predetermined;
vi. the Young's modulus of the spacers multiplied by the filling factor of the spacers is at least 2 MPa; and
vii. at least one of the spacers is inside the sample contact area; and
wherein one of the configurations is an open configuration, in which: the two plates are partially or completely separated apart, the spacing between the plates is not regulated by the spacers, and the sample is deposited on one or both of the plates; and
wherein another of the configurations is a closed configuration which is configured after the sample is deposited in the open configuration; and in the closed configuration: at least part of the sample is compressed by the two plates into a layer of highly uniform thickness, wherein the uniform thickness of the layer is confined by the sample contact surfaces of the plates and is regulated by the plates and the spacers.

A method of forming a thin fluidic sample layer with a uniform predetermined thickness by pressing, comprising the steps of:
(a) obtaining a device of embodiment any prior embodiment;
(b) depositing a fluidic sample on one or both of the plates; when the plates are configured in an open configuration, wherein the open configuration is a configuration in which the two plates are partially or completely separated apart and the spacing between the plates is not regulated by the spacers;
(c) after (b), forcing the two plates into a closed configuration, in which: at least part of the sample is compressed by the two plates into a layer of substantially uniform thickness, wherein the uniform thickness of the layer is confined by the sample contact surfaces of the plates and is regulated by the plates and the spacers.

A device for analyzing a fluidic sample, comprising:
a first plate and a second plate, wherein:
i. the plates are movable relative to each other into different configurations;
ii. one or both plates are flexible;
iii. each of the plates has, on its respective surface, a sample contact area for contacting a sample that contains an analyte,
iv. one or both of the plates comprise spacers that are permanently fixed to a plate within a sample contact area, wherein the spacers have a predetermined substantially uniform height and a predetermined fixed inter-spacer distance that is at least about 2 times larger than the size of the analyte, up to 200 μm, and wherein at least one of the spacers is inside the sample contact area;
wherein one of the configurations is an open configuration, in which: the two plates are separated apart, the spacing between the plates is not regulated by the spacers, and the sample is deposited on one or both of the plates; and
wherein another of the configurations is a closed configuration which is configured after the sample deposition in the open configuration; and in the closed configuration: at least part of the sample is compressed by the two plates into a layer of highly uniform thickness, wherein the uniform thickness of the layer is confined by the sample contact surfaces of the plates and is regulated by the plates and the spacers.

A method of forming a thin fluidic sample layer with a uniform predetermined thickness by pressing, comprising the steps of:
(a) obtaining a device of any prior embodiment;
(b) depositing a fluidic sample on one or both of the plates; when the plates are configured in an open configuration, wherein the open configuration is a configuration in which the two plates are partially or completely separated apart and the spacing between the plates is not regulated by the spacers;
(c) after (b), forcing the two plates into a closed configuration, in which: at least part of the sample is compressed by the two plates into a layer of substantially uniform thickness, wherein the uniform thickness of the layer is confined by the sample contact surfaces of the plates and is regulated by the plates and the spacers.

A device for forming a thin fluidic sample layer with a uniform predetermined thickness by pressing, comprising:
a first plate, a second plate, and spacers, wherein:
i. the plates are movable relative to each other into different configurations;
ii. one or both plates are flexible;
iii. each of the plates comprises, on its respective inner surface, a sample contact area for contacting and/or compressing a fluidic sample;
iv. each of the plates comprises, on its respective outer surface, an area for applying a force that forces the plates together;
v. one or both of the plates comprise the spacers that are permanently fixed on the inner surface of a respective plate;

vi. the spacers have a predetermined substantially uniform height that is equal to or less than 200 microns, a predetermined width, and a predetermined fixed inter-spacer-distance;
vii. a ratio of the inter-spacer-distance to the spacer width is 1.5 or larger; and
viii. at least one of the spacers is inside the sample contact area;

wherein one of the configurations is an open configuration, in which: the two plates are partially or completely separated apart, the spacing between the plates is not regulated by the spacers, and the sample is deposited on one or both of the plates;

wherein another of the configurations is a closed configuration which is configured after the sample deposition in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers.

A method of forming a thin fluidic sample layer with a uniform predetermined thickness by pressing with an imprecise pressing force, comprising the steps of:

(a) obtaining a device of embodiment any prior embodiment;
(b) obtaining a fluidic sample;
(c) depositing the sample on one or both of the plates; when the plates are configured in an open configuration, wherein the open configuration is a configuration in which the two plates are partially or completely separated apart and the spacing between the plates is not regulated by the spacers;
(d) after (c), forcing the two plates into a closed configuration, in which: at least part of the sample is compressed by the two plates into a layer of substantially uniform thickness, wherein the uniform thickness of the layer is confined by the sample contact surfaces of the plates and is regulated by the plates and the spacers.

The devices or methods of any prior embodiment, wherein the spacers have a shape of pillar with a foot fixed on one of the plate and a flat top surface for contacting the other plate.

The devices or methods of any prior embodiment, wherein the spacers have a shape of pillar with a foot fixed on one of the plate, a flat top surface for contacting the other plate, substantially uniform cross-section.

The devices or methods of any prior embodiment, wherein the spacers have a shape of pillar with a foot fixed on one of the plate and a flat top surface for contacting the other plate, wherein the flat top surface of the pillars has a variation in less than 10 nm.

The devices or methods of any prior embodiment, wherein the spacers have a shape of pillar with a foot fixed on one of the plate and a flat top surface for contacting the other plate, wherein the flat top surface of the pillars has a variation in less than 50 nm.

The devices or methods of any prior embodiment, wherein the spacers have a shape of pillar with a foot fixed on one of the plate and a flat top surface for contacting the other plate, wherein the flat top surface of the pillars has a variation in less than 50 nm.

The devices or methods of any prior embodiment, wherein the spacers have a shape of pillar with a foot fixed on one of the plate and a flat top surface for contacting the other plate, wherein the flat top surface of the pillars has a variation in less than 10 nm, 20 nm, 30 nm, 100 nm, 200 nm, or in a range of any two of the values.

The devices or methods of any prior embodiment, wherein the Young's modulus of the spacers multiplied by the filling factor of the spacers is at least 2 MPa.

The devices or methods of any prior embodiment, wherein the sample comprises an analyte and the predetermined constant inter-spacer distance is at least about 2 times larger than the size of the analyte, up to 200 μm.

The devices or methods of any prior embodiment, wherein the sample comprise an analyte, the predetermined constant inter-spacer distance is at least about 2 times larger than the size of the analyte, up to 200 μm, and the Young's modulus of the spacers multiplied by the filling factor of the spacers is at least 2 MPa.

The devices or methods of any prior embodiment, wherein a fourth power of the inter-spacer-distance (IDS) divided by the thickness (h) and the Young's modulus (E) of the flexible plate (ISD$^4$/(hE)) is $5 \times 10^6$ μm$^3$/GPa or less.

The devices or methods of any prior embodiment, wherein a fourth power of the inter-spacer-distance (IDS) divided by the thickness (h) and the Young's modulus (E) of the flexible plate (ISD$^4$/(hE)) is $1 \times 10^6$ μm$^3$/GPa or less.

The devices or methods of any prior embodiment, wherein a fourth power of the inter-spacer-distance (IDS) divided by the thickness (h) and the Young's modulus (E) of the flexible plate (ISD$^4$/(hE)) is $5 \times 10^5$ μm$^3$/GPa or less.

The devices or methods of any prior embodiment, wherein the Young's modulus of the spacers multiplied by the filling factor of the spacers is at least 2 MPa, and a fourth power of the inter-spacer-distance (IDS) divided by the thickness (h) and the Young's modulus (E) of the flexible plate (ISD$^4$/(hE)) is $1 \times 10^5$ μm$^3$/GPa or less.

The devices or methods of any prior embodiment, wherein the Young's modulus of the spacers multiplied by the filling factor of the spacers is at least 2 MPa, and a fourth power of the inter-spacer-distance (IDS) divided by the thickness (h) and the Young's modulus (E) of the flexible plate (ISD$^4$/(hE)) is $1 \times 10^4$ μm$^3$/GPa or less.

The devices or methods of any prior embodiment, wherein the Young's modulus of the spacers multiplied by the filling factor of the spacers is at least 20 MPa.

The devices or methods of any prior embodiment, wherein the ratio of the inter-spacing distance of the spacers to the average width of the spacer is 2 or larger.

The devices or methods of any prior embodiment, wherein the ratio of the inter-spacing distance of the spacers to the average width of the spacer is 2 or larger, and the Young's modulus of the spacers multiplied by the filling factor of the spacers is at least 2 MPa.

The devices or methods of any prior embodiment, wherein inter-spacer distance that is at least about 2 times larger than the size of the analyte, up to 200 μm.

The devices or methods of any prior embodiment, wherein a ratio of the inter-spacer-distance to the spacer width is 1.5 or larger.

The devices or methods of any prior embodiment, wherein a ratio of the width to the height of the spacer is 1 or larger.

The devices or methods of any prior embodiment, wherein a ratio of the width to the height of the spacer is 1.5 or larger.

The devices or methods of any prior embodiment, wherein a ratio of the width to the height of the spacer is 2 or larger.

The devices or methods of any prior embodiment, wherein a ratio of the width to the height of the spacer is larger than 2, 3, 5, 10, 20, 30, 50, or in a range of any two the value.

The methods of any prior embodiment, wherein the force that presses the two plates into the closed configuration is an imprecise pressing force.

The methods of any prior embodiment, wherein the force that presses the two plates into the closed configuration is an imprecise pressing force provided by human hand.

The methods of any prior embodiment, wherein the forcing of the two plates to compress at least part of the sample into a layer of substantially uniform thickness comprises a use of a conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and wherein the reduced thickness of the sample reduces the time for mixing the reagents on the storage site with the sample.

The methods of any prior embodiment, wherein the pressing force is an imprecise force that has a magnitude which is, at the time that the force is applied, either (a) unknown and unpredictable, or (b) cannot be known and cannot be predicted within an accuracy equal or better than 20% of the average pressing force applied.

The methods of any prior embodiment, wherein the pressing force is an imprecise force that has a magnitude which is, at the time that the force is applied, either (a) unknown and unpredictable, or (b) cannot be known and cannot be predicted within an accuracy equal or better than 30% of the average pressing force applied.

The methods of any prior embodiment, wherein the pressing force is an imprecise force that has a magnitude which is, at the time that the force is applied, either (a) unknown and unpredictable, or (b) cannot be known and cannot be predicted within an accuracy equal or better than 30% of the average pressing force applied; and wherein the layer of highly uniform thickness has a variation in thickness of 20% or less.

The methods of any prior embodiment, wherein the pressing force is an imprecise force that has a magnitude which cannot, at the time that the force is applied, be determined within an accuracy equal or better than 30%, 40%, 50%, 70%, 100%, 200%, 300%, 500%, 1000%, 2000%, or in a range between any of the two values.

The devices or methods of any prior embodiment, wherein the flexible plate has a thickness of in the range of 10 μm to 200 μm.

The devices or methods of any prior embodiment, wherein the flexible plate has a thickness of in the range of 20 μm to 100 μm.

The devices or methods of any prior embodiment, wherein the flexible plate has a thickness of in the range of 25 μm to 180 μm.

The devices or methods of any prior embodiment, wherein the flexible plate has a thickness of in the range of 200 μm to 260 μm.

The devices or methods of any prior embodiment, wherein the flexible plate has a thickness of equal to or less than 250 μm, 225 μm, 200 μm, 175 μm, 150 μm, 125 μm, 100 μm, 75 μm, 50 μm, 25 μm, 10 μm, 5 μm, 1 μm, or in a range between the two of the values.

The devices or methods of any prior method, wherein the sample has a viscosity in the range of 0.1 to 4 (mPa s).

The devices or methods of any prior embodiment, wherein the flexible plate has a thickness of in the range of 200 μm to 260 μm.

The devices or methods of any prior embodiment, wherein the flexible plate has a thickness in the range of 20 μm to 200 μm and Young's modulus in the range 0.1 to 5 GPa.

The method of any prior claim, wherein the sample deposition of step (b) is a deposition directly from a subject to the plate without using any transferring devices.

The method any prior claim, wherein during the deposition of step (b), the amount of the sample deposited on the plate is unknown.

The method of any prior claim, wherein the method further comprises a analyzing step (e) that analyze the sample.

The method of any prior claim, wherein the analyzing step (e) comprises calculating the volume of a relevant sample volume by measuring the lateral area of the relevant sample volume and calculating the volume from the lateral area and the predetermined spacer height.

The method of any prior claim, wherein the analyzing step (e) comprises measuring:
  i. imaging, iiluminescence selected from photoluminescence, electroluminescence, and electrochemiluminescence,
  iii. surface Raman scattering,
  iv. electrical impedance selected from resistance, capacitance, and inductance, or
  v. any combination of i-iv.

The method of any prior claim, wherein the analyzing step (e) comprises reading, image analysis, or counting of the analyte, or a combination of thereof.

The method of any prior claim, wherein the sample contains one or plurality of analytes, and one or both plate sample contact surfaces comprise one or a plurality of binding sites that each binds and immobilize a respective analyte.

The method of any prior claim, wherein one or both plate sample contact surfaces comprise one or a plurality of storage sites that each stores a reagent or reagents, wherein the reagent(s) dissolve and diffuse in the sample during or after step (c).

The method of any prior claim, wherein one or both plate sample contact surfaces comprises one or a plurality of amplification sites that are each capable of amplifying a signal from the analyte or a label of the analyte when the analyte or label is within 500 nm from an amplification site.

The method of any prior claim, wherein:
  i. one or both plate sample contact surfaces comprise one or a plurality of binding sites that each binds and immobilize a respective analyte; or
  ii. one or both plate sample contact surfaces comprise, one or a plurality of storage sites that each stores a reagent or reagents; wherein the reagent(s) dissolve and diffuse in the sample during or after step (c), and wherein the sample contains one or plurality of analytes; or
  iii. one or a plurality of amplification sites that are each capable of amplifying a signal from the analyte or a label of the analyte when the analyte or label is 500 nm from the amplification site; or
  iv. any combination of i to iii.

The devices or methods of any prior embodiment, wherein the liquid sample is a biological sample selected from amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, and urine.

The devices or methods of any prior embodiment, wherein the layer of uniform thickness in the closed configuration is less than 150 μm.

The method of any prior claim, wherein the pressing is provided by a pressured liquid, a pressed gas, or a conformal material.

The method of any prior claim, wherein the analyzing comprises counting cells in the layer of uniform thickness.

The method of any prior claim, wherein the analyzing comprises performing an assay in the layer of uniform thickness.

The devices or methods of any prior embodiment, wherein the assay is a binding assay or biochemical assay.

The method of any prior embodiment, wherein the sample deposited has a total volume less 0.5 μL The method of any prior embodiment, wherein multiple drops of sample are deposited onto one or both of the plates.

The devices or methods of any prior embodiment, wherein the inter-spacer distance is in the range of 1 μm to 120 μm.

The devices or methods of any prior embodiment, wherein the inter-spacer distance is in the range of 120 μm to 50 μm.

The devices or methods of any prior embodiment, wherein the inter-spacer distance is in the range of 120 μm to 200 μm.

The device of any prior device claim, wherein the flexible plates have a thickness in the range of 20 μm to 250 μm and Young's modulus in the range 0.1 to 5 GPa.

The device of any prior device claim, wherein for a flexible plate, the thickness of the flexible plate times the Young's modulus of the flexible plate is in the range 60 to 750 GPa-μm.

The device of any prior device claim, wherein the layer of uniform thickness sample is uniform over a lateral area that is at least 1 mm$^2$.

The device of any prior device claim, wherein the layer of uniform thickness sample is uniform over a lateral area that is at least 3 mm$^2$.

The device of any prior device claim, wherein the layer of uniform thickness sample is uniform over a lateral area that is at least 5 mm$^2$.

The device of any prior device claim, wherein the layer of uniform thickness sample is uniform over a lateral area that is at least 10 mm$^2$.

The device of any prior device claim, wherein the layer of uniform thickness sample is uniform over a lateral area that is at least 20 mm$^2$.

The device of any prior device claim, wherein the layer of uniform thickness sample is uniform over a lateral area that is in a range of 20 mm$^2$ to 100 mm$^2$.

The device of any prior device claim, wherein the layer of uniform thickness sample has a thickness uniformity of up to +/−5% or better.

The device of any prior device claim, wherein the layer of uniform thickness sample has a thickness uniformity of up to +/−10% or better.

The device of any prior device claim, wherein the layer of uniform thickness sample has a thickness uniformity of up to +/−20% or better.

The device of any prior device claim, wherein the layer of uniform thickness sample has a thickness uniformity of up to +/−30% or better.

The device of any prior device claim, wherein the layer of uniform thickness sample has a thickness uniformity of up to +/−40% or better.

The device of any prior device claim, wherein the layer of uniform thickness sample has a thickness uniformity of up to +/−50% or better.

The device of any prior device claim, wherein the spacers are pillars with a cross-sectional shape selected from round, polygonal, circular, square, rectangular, oval, elliptical, or any combination of the same.

The device of any prior device claim, wherein the spacers have pillar shape, have a substantially flat top surface, and have substantially uniform cross-section, wherein, for each spacer, the ratio of the lateral dimension of the spacer to its height is at least 1.

The device of any prior device claim, wherein the inter spacer distance is periodic.

The device of any prior device claim, wherein the spacers have a filling factor of 1% or higher, wherein the filling factor is the ratio of the spacer contact area to the total plate area.

The device of any prior device claim, wherein the Young's modulus of the spacers times the filling factor of the spacers is equal or larger than 20 MPa, wherein the filling factor is the ratio of the spacer contact area to the total plate area.

The device of any prior device claim, wherein the spacing between the two plates at the closed configuration is in less 200 μm.

The device of any prior device claim, wherein the spacing between the two plates at the closed configuration is a value selected from between 1.8 μm and 3.5 μm.

The device of any prior device claim, wherein the spacing are fixed on a plate by directly embossing the plate or injection molding of the plate.

The device of any prior device claim, wherein the materials of the plate and the spacers are selected from polystyrene, PMMA, PC, COC, COP, or another plastic.

The device of any prior device claim, wherein the spacers have a pillar shape, and the sidewall corners of the spacers have a round shape with a radius of curvature at least 1 μm.

The device of any prior device claim, wherein the spacers have a density of at least 1,000/mm$^2$.

The device of any prior device claim, wherein at least one of the plates is transparent.

The device of any prior device claim, wherein the mold used to make the spacers is fabricated by a mold containing features that are fabricated by either (a) directly reactive ion etching or ion beam etched or (b) by a duplication or multiple duplication of the features that are reactive ion etched or ion beam etched.

The devices or methods of any prior embodiment, wherein the spacers are configured, such that the filling factor is in the range of 1% to 5%.

The devices or methods of any prior embodiment, wherein the surface variation is relative to the spacer height and the ratio of the pillar flat top surface variation to the spacer height is less than 0.5%, 1%, 3%, 5%, 7%, 10%, 15%, 20%, 30%, 40%, or in a range between any two of the values. A preferred flat pillar top smoothness has a ratio of the pillar flat top surface variation to the spacer height is less than 2%, 5%, or 10%.

The devices or methods of any prior embodiment, wherein the spacers are configured, such that the filling factor is in the range of 1% to 5%.

The devices or methods of any prior embodiment, wherein the spacers are configured, such that the filling factor is in the range of 5% to 10%.

The devices or methods of any prior embodiment, wherein the spacers are configured, such that the filling factor is in the range of 10% to 20%.

The devices or methods of any prior embodiment, wherein the spacers are configured, such that the filling factor is in the range of 20% to 30%.

The devices or methods of any prior embodiment, wherein the spacers are configured, such that the filling factor is 5%, 10%, 20%, 30%, 40%, 50%, or in a range of any two of the values.

The devices or methods of any prior embodiment, wherein the spacers are configured, such that the filling factor is 50%, 60%, 70%, 80%, or in a range of any two of the values.

The devices or methods of any prior embodiment, wherein the spacers are configured, such that the filling factor multiplies the Young's modulus of the spacer is in the range of 2 MPa and 10 MPa.

The devices or methods of any prior embodiment, wherein the spacers are configured, such that the filling factor multiplies the Young's modulus of the spacer is in the range of 10 MPa and 20 MPa.

The devices or methods of any prior embodiment, wherein the spacers are configured, such that the filling factor multiplies the Young's modulus of the spacer is in the range of 20 MPa and 40 MPa.

The devices or methods of any prior embodiment, wherein the spacers are configured, such that the filling factor multiplies the Young's modulus of the spacer is in the range of 40 MPa and 80 MPa.

The devices or methods of any prior embodiment, wherein the spacers are configured, such that the filling factor multiplies the Young's modulus of the spacer is in the range of 80 MPa and 120 MPa.

The devices or methods of any prior embodiment, wherein the spacers are configured, such that the filling factor multiplies the Young's modulus of the spacer is in the range of 120 MPa to 150 MPa.

The devices or methods of any prior embodiment, wherein the device further comprises a dry reagent coated on one or both plates.

The devices or methods of any prior embodiment, wherein the device further comprises, on one or both plates, a dry binding site that has a predetermined area, wherein the dry binding site binds to and immobilizes an analyte in the sample.

The devices or methods of any prior embodiment, wherein the device further comprises, on one or both plates, a releasable dry reagent and a release time control material that delays the time that the releasable dry regent is released into the sample.

The device of any prior embodiment, wherein the release time control material delays the time that the dry regent starts is released into the sample by at least 3 seconds.

The device of any prior embodiment, wherein the regent comprises anticoagulant and/or staining reagent(s).

The device of any prior embodiment, wherein the reagent comprises cell lysing reagent(s).

The devices or methods of any prior embodiment, wherein the device further comprises, on one or both plates, one or a plurality of dry binding sites and/or one or a plurality of reagent sites.

The device of any prior device embodiment, wherein the analyte comprises a molecule (e.g., a protein, peptides, DNA, RNA, nucleic acid, or other molecule), cells, tissues, viruses, and nanoparticles with different shapes.

The device of any prior device embodiment, wherein the analyte comprises white blood cells, red blood cells and platelets.

The device of any prior device embodiment, wherein the analyte is stained.

The devices or methods of any prior embodiment, wherein the spacers regulating the layer of uniform thickness have a filling factor of at least 1%, wherein the filling factor is the ratio of the spacer area in contact with the layer of uniform thickness to the total plate area in contact with the layer of uniform thickness.

The devices or methods of any prior embodiment, wherein for spacers regulating the layer of uniform thickness, the Young's modulus of the spacers times the filling factor of the spacers is equal or larger than 10 MPa, wherein the filling factor is the ratio of the spacer area in contact with the layer of uniform thickness to the total plate area in contact with the layer of uniform thickness.

The devices or methods of any prior embodiment, wherein for a flexible plate, the thickness of the flexible plate times the Young's modulus of the flexible plate is in the range 60 to 750 GPa-µm.

The devices or methods of any prior embodiment, wherein for a flexible plate, the fourth power of the inter-spacer-distance (ISD) divided by the thickness of the flexible plate (h) and the Young's modulus (E) of the flexible plate, $ISD^4/(hE)$, is equal to or less than $10^6$ µm$^3$/GPa, The devices or methods of any prior embodiment, wherein one or both plates comprises a location marker, either on a surface of or inside the plate, that provide information of a location of the plate.

The devices or methods of any prior embodiment, wherein one or both plates comprises a scale marker, either on a surface of or inside the plate, that provide information of a lateral dimension of a structure of the sample and/or the plate.

The devices or methods of any prior embodiment, wherein one or both plates comprises an imaging marker, either on surface of or inside the plate, that assists an imaging of the sample.

The devices or methods of any prior embodiment, wherein the spacers functions as a location marker, a scale marker, an imaging marker, or any combination of thereof.

The devices or methods of any prior embodiment, wherein the average thickness of the layer of uniform thickness is about equal to a minimum dimension of an analyte in the sample.

The devices or methods of any prior embodiment, wherein the inter-spacer distance is in the range of 7 µm to 50 µm.

The devices or methods of any prior embodiment, wherein the inter-spacer distance is in the range of 50 µm to 120 µm.

The devices or methods of any prior embodiment, wherein the inter-spacer distance is in the range of 120 µm to 200 µm (micron).

The devices or methods of any prior embodiment, wherein the inter-spacer distance is substantially periodic.

The devices or methods of any prior embodiment, wherein the spacers are pillars with a cross-sectional shape selected from round, polygonal, circular, square, rectangular, oval, elliptical, or any combination of the same.

The devices or methods of any prior embodiment, wherein the spacers have are pillar shape and have a substantially flat top surface, wherein, for each spacer, the ratio of the lateral dimension of the spacer to its height is at least 1.

The devices or methods of any prior embodiment, wherein each spacer has the ratio of the lateral dimension of the spacer to its height is at least 1.

The devices or methods of any prior embodiment, wherein the minimum lateral dimension of spacer is less than or substantially equal to the minimum dimension of an analyte in the sample.

The devices or methods of any prior embodiment, wherein the minimum lateral dimension of spacer is in the range of 0.5 μm to 100 μm.

The devices or methods of any prior embodiment, wherein the minimum lateral dimension of spacer is in the range of 0.5 μm to 10 μm.

The devices or methods of any prior embodiment, wherein the sample is blood.

The devices or methods of any prior embodiment, wherein the sample is whole blood without dilution by liquid.

The devices or methods of any prior embodiment, wherein the sample is a biological sample selected from amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, and urine.

The devices or methods of any prior embodiment, wherein the sample is a biological sample, an environmental sample, a chemical sample, or clinical sample.

The devices or methods of any prior embodiment, wherein the spacers have a pillar shape, and the sidewall corners of the spacers have a round shape with a radius of curvature at least 1 μm.

The devices or methods of any prior embodiment, wherein the spacers have a density of at least $100/mm^2$.

The devices or methods of any prior embodiment, wherein the spacers have a density of at least $1,000/mm^2$.

The devices or methods of any prior embodiment, wherein at least one of the plates is transparent.

The devices or methods of any prior embodiment, wherein at least one of the plates is made from a flexible polymer.

The devices or methods of any prior embodiment, wherein, for a pressure that compresses the plates, the spacers are not compressible and/or, independently, only one of the plates is flexible.

The device of any of any prior embodiment, wherein the flexible plate has a thickness in the range of 10 μm to 200 μm.

The devices or methods of any prior embodiment, wherein the variation is less than 30%.

The devices or methods of any prior embodiment, wherein the variation is less than 10%.

The devices or methods of any prior embodiment, wherein the variation is less than 5%.

The devices or methods of any prior embodiment, wherein the first and second plates are connected and are configured to be changed from the open configuration to the closed configuration by folding the plates.

The devices or methods of any prior embodiment, wherein the first and second plates are connected by a hinge and are configured to be changed from the open configuration to the closed configuration by folding the plates along the hinge.

The devices or methods of any prior embodiment, wherein the first and second plates are connected by a hinge that is a separate material to the plates, and are configured to be changed from the open configuration to the closed configuration by folding the plates along the hinge The devices or methods of any prior embodiment, wherein the first and second plates are made in a single piece of material and are configured to be changed from the open configuration to the closed configuration by folding the plates.

The devices or methods of any prior embodiment, wherein the layer of uniform thickness sample is uniform over a lateral area that is at least 1 $mm^2$.

The devices or methods of any prior embodiment, wherein the device is configured to analyze the sample in 60 seconds or less.

The devices or methods of any prior embodiment, wherein at the closed configuration, the final sample thickness device is configured to analyze the sample in 60 seconds or less.

The devices or methods of any prior embodiment, wherein at the closed configuration, the final sample thickness device is configured to analyze the sample in 10 seconds or less.

The devices or methods of any prior embodiment, wherein the dry binding site comprises a capture agent.

The devices or methods of any prior embodiment, wherein the dry binding site comprises an antibody or nucleic acid.

The devices or methods of any prior embodiment, wherein the releasable dry reagent is a labeled reagent.

The devices or methods of any prior embodiment, wherein the releasable dry reagent is a fluorescently-labeled reagent.

The devices or methods of any prior embodiment, wherein the releasable dry reagent is a fluorescently-labeled antibody.

The devices or methods of any prior embodiment, wherein the releasable dry reagent is a cell stain.

The devices or methods of any prior embodiment, wherein the releasable dry reagent is a cell lysing.

The devices or methods of any prior embodiment, wherein the detector is an optical detector that detects an optical signal.

The devices or methods of any prior embodiment, wherein the detector is an electric detector that detect electrical signal.

The device of any prior device embodiment, wherein the spacing are fixed on a plate by directly embossing the plate or injection molding of the plate.

The device of any prior device embodiment, wherein the materials of the plate and the spacers are selected from polystyrene, PMMA, PC, COC, COP, or another plastic.

A system for rapidly analyzing a sample using a mobile phone comprising:

(a) a device of any prior embodiment;
(b) a mobile communication device comprising:
  i. one or a plurality of cameras for the detecting and/or imaging the sample;
  ii. electronics, signal processors, hardware and software for receiving and/or processing the detected signal and/or the image of the sample and for remote communication; and
(c) a light source from either the mobile communication device or an external source;
wherein the detector in The devices or methods of any prior embodiment is provided by the mobile communication device, and detects an analyte in the sample at the closed configuration.

The system of any prior system embodiment, wherein one of the plates has a binding site that binds an analyte, wherein at least part of the uniform sample thickness layer is over the binding site, and is substantially less than the average lateral linear dimension of the binding site.

The system of any prior system embodiment, further comprising:
(d) a housing configured to hold the sample and to be mounted to the mobile communication device.

The system of any prior system embodiment, wherein the housing comprises optics for facilitating the imaging and/or signal processing of the sample by the mobile communication device, and a mount configured to hold the optics on the mobile communication device.

The system of any prior system embodiment, wherein an element of the optics in the housing is movable relative to the housing.

The system of any prior system embodiment, wherein the mobile communication device is configured to communicate test results to a medical professional, a medical facility or an insurance company.

The system of any prior system embodiment, wherein the mobile communication device is further configured to communicate information on the test and the subject with the medical professional, medical facility or insurance company.

The system of any prior system embodiment, wherein the mobile communication device is further configured to communicate information of the test to a cloud network, and the cloud network process the information to refine the test results.

The system of any prior system embodiment, wherein the mobile communication device is further configured to communicate information of the test and the subject to a cloud network, the cloud network process the information to refine the test results, and the refined test results will send back the subject.

The system of any prior system embodiment, wherein the mobile communication device is configured to receive a prescription, diagnosis or a recommendation from a medical professional.

The system of any prior system embodiment, wherein the mobile communication device is configured with hardware and software to:
(a) capture an image of the sample;
(b) analyze a test location and a control location in in image; and
(c) compare a value obtained from analysis of the test location to a threshold value that characterizes the rapid diagnostic test.

The system of any prior system embodiment, wherein at least one of the plates comprises a storage site in which assay reagents are stored.

The system of any prior system embodiment, at least one of the cameras reads a signal from the device.

The system of any prior system embodiment, wherein the mobile communication device communicates with the remote location via a Wi-Fi or cellular network.

The system of any prior system embodiment, wherein the mobile communication device is a mobile phone.

A method for rapidly analyzing an analyte in a sample using a mobile phone, comprising:
(a) depositing a sample on the device of any prior system embodiment;
(b) assaying an analyte in the sample deposited on the device to generate a result; and
(c) communicating the result from the mobile communication device to a location remote from the mobile communication device.

The method of any prior embodiment, wherein the analyte comprises a molecule (e.g., a protein, peptides, DNA, RNA, nucleic acid, or other molecule), cells, tissues, viruses, and nanoparticles with different shapes.

The method of any prior embodiment, wherein the analyte comprises white blood cell, red blood cell and platelets.

The method of any prior embodiment, wherein the assaying comprises performing a white blood cells differential assay.

The method of any prior embodiment, wherein the method comprises:
analyzing the results at the remote location to provide an analyzed result; and
communicating the analyzed result from the remote location to the mobile communication device.

The method of any prior embodiment, wherein the analysis is done by a medical professional at a remote location.

The method of any prior embodiment, wherein the mobile communication device receives a prescription, diagnosis or a recommendation from a medical professional at a remote location.

The method of any prior embodiment, wherein the sample is a bodily fluid.

The method of any prior embodiment, wherein the bodily fluid is blood, saliva or urine.

The method of any prior embodiment, wherein the sample is whole blood without dilution by a liquid.

The method of any prior embodiment, wherein the assaying step comprises detecting an analyte in the sample.

The method of any prior embodiment, wherein the analyte is a biomarker.

The method of any prior embodiment, wherein the analyte is a protein, nucleic acid, cell, or metabolite.

The method of any prior embodiment, wherein the method comprises counting the number of red blood cells.

The method of any of any prior embodiment, wherein the method comprises counting the number of white blood cells.

The method of any prior embodiment, wherein method comprises staining the cells in the sample and counting the number of neutrophils, lymphocytes, monocytes, eosinophils and basophils.

The method of any prior embodiments embodiment, wherein the assay done in step (b) is a binding assay or a biochemical assay.

A method for analyzing a sample comprising:
obtaining a device of any prior device embodiment;
depositing the sample onto one or both plates of the device;
placing the plates in a closed configuration and applying an external force over at least part of the plates; and analyzing the in the layer of uniform thickness while the plates are the closed configuration.

The devices or methods of any prior embodiment, wherein the first plate further comprises, on its surface, a first predetermined assay site and a second predetermined assay site, wherein the distance between the edges of the assay site is substantially larger than the thickness of the uniform thickness layer when the plates are in the closed position, wherein at least a part of the uniform thickness layer is over the predetermined assay sites, and wherein the sample has one or a plurality of analytes that are capable of diffusing in the sample.

The devices or methods of any prior embodiment, wherein the first plate has, on its surface, at least three analyte assay sites, and the distance between the edges of any two neighboring assay sites is substantially larger than the thickness of the uniform thickness layer when the plates are in the closed position, wherein at least a part of the uniform thickness layer is over the assay sites, and wherein the sample has one or a plurality of analytes that are capable of diffusing in the sample.

The devices or methods of any prior embodiment, wherein the first plate has, on its surface, at least two neighboring analyte assay sites that are not separated by a distance that is substantially larger than the thickness of the uniform thickness layer when the plates are in the closed position, wherein at least a part of the uniform thickness layer is over the assay sites, and wherein the sample has one or a plurality of analytes that are capable of diffusing in the sample.

The devices or methods of any prior embodiment, wherein the analyte assay area is between a pair of electrodes.

The devices or methods of any prior embodiment, wherein the assay area is defined by a patch of dried reagent.

The devices or methods of any prior embodiment, wherein the assay area binds to and immobilizes the analyte The devices or methods of any prior embodiment, wherein the assay area is defined by a patch of binding reagent that, upon contacting the sample, dissolves into the sample, diffuses in the sample, and binds to the analyte.

The devices or methods of any prior embodiment, wherein the inter-spacer distance is in the range of 14 µm to 200 µm.

The devices or methods of any prior embodiment, wherein the inter-spacer distance is in the range of 7 µm to 20 µm.

The devices or methods of any prior embodiment, wherein the spacers are pillars with a cross-sectional shape selected from round, polygonal, circular, square, rectangular, oval, elliptical, or any combination of the same.

The devices or methods of any prior embodiment, wherein the spacers have are pillar shape and have a substantially flat top surface, wherein, for each spacer, the ratio of the lateral dimension of the spacer to its height is at least 1.

The devices or methods of any prior embodiment, wherein the spacers have a pillar shape, and the sidewall corners of the spacers have a round shape with a radius of curvature at least 1 µm.

The devices or methods of any prior embodiment, wherein the spacers have a density of at least 1,000/mm$^2$.

The devices or methods of any prior embodiment, wherein at least one of the plates is transparent.

The devices or methods of any prior embodiment, wherein at least one of the plates is made from a flexible polymer.

The devices or methods of any prior embodiment, wherein only one of the plates is flexible.

The device of any prior embodiment, wherein the area-determination device is a camera.

The devices or methods of any prior embodiment, wherein the deformable sample comprises a liquid sample.

The devices or methods of any prior embodiment, wherein the imprecision force has a variation at least 30% of the total force that actually is applied.

The devices or methods of any prior embodiment, wherein the imprecision force has a variation at least 20%, 30%, 40%, 50%, 60, 70%, 80%, 90% 100%, 150%, 200%, 300%, 500%, or in a range of any two values, of the total force that actually is applied.

The device of any prior embodiment, wherein spacers have a flat top.

The device of any prior embodiment, wherein the device is further configured to have, after the pressing force is removed, a sample thickness that is substantially the same in thickness and uniformity as that when the force is applied.

The device of any prior embodiment, wherein the imprecise force is provided by human hand.

The device of any prior embodiment, wherein the inter spacer distance is substantially constant.

The device of any prior embodiment, wherein the inter spacer distance is substantially periodic in the area of the uniform sample thickness area.

The device of any prior embodiment, wherein the multiplication product of the filling factor and the Young's modulus of the spacer is 2 MPa or larger.

The device of any prior embodiment, wherein the force is applied by hand directly or indirectly.

The device of any prior embodiment, wherein the force applied is in the range of 1 N to 20 N.

The device of any prior embodiment, wherein the force applied is in the range of 20 N to 200 N.

The device of any prior embodiment wherein the highly uniform layer has a thickness that varies by less than 15%, 10%, or 5% of an average thickness.

The device of any prior embodiment, wherein the imprecise force is applied by pinching the device between a thumb and forefinger.

The device of any prior embodiment, wherein the predetermined sample thickness is larger than the spacer height.

The device of any prior embodiment, wherein the device holds itself in the closed configuration after the pressing force has been removed.

The device of any prior embodiment, wherein the uniform thickness sample layer area is larger than that area upon which the pressing force is applied.

The device of any prior embodiment, wherein the spacers do not significantly deform during application of the pressing force.

The device of any prior embodiment, wherein the pressing force is not predetermined beforehand and is not measured.

In some embodiments, the fluidic sample is replaced by a deformable sample and the embodiments for making at least a part of the fluidic sample into a uniform thickness layer can make at least a part of the deformable sample into a uniform thickness layer.

The devices and methods of any prior device claim, wherein the inter spacer distance is periodic.

The devices and methods of any prior device claim, wherein the spacers have a flat top.

The devices and methods of any prior device claim, wherein the inter spacer distance is at least two times large than the size of the targeted analyte in the sample.

Manufacturing of Q-Card

An embodiment of the Q-Card comprising: a first plate, a second plate, and a hinge, wherein
  i. the first plate, that is about 200 nm to 1500 nm thick, comprises, on its inner surface, (a) a sample contact area for contacting a sample, and (b) a sample overflow dam that surrounds the sample contact area is configured to present a sample flow outside of the dam;
  ii. the second plate is 10 μm
  iii. to 250 μm thick and comprises, on its inner surface, (a) a sample contact area for contacting a sample, and (b) spacers on the sample contact area;
  iv. the hinge that connect the first and the second plates; and
wherein the first and second plate are movable relative to each other around the axis of the hinge.

An embodiment of the Q-Card comprising: a first plate, a second plate, and a hinge, wherein
  i. the first plate, that is about 200 nm to 1500 nm thick, comprises, on its inner surface, (a) a sample contact area for contacting a sample, (b) a sample overflow dam that surrounds the sample contact area is configured to present a sample flow outside of the dam, and (c) spacers on the sample contact area;
  ii. the second plate, that is 10 μm to 250 μm thick, comprises, on its inner surface, a sample contact area for contacting a sample;
  iii. the hinge that connect the first and the second plates; and
wherein the first and second plate are movable relative to each other around the axis of the hinge.

An embodiment of the Q-Card comprising: a first plate, a second plate, and a hinge, wherein
  i. the first plate, that is about 200 nm to 1500 nm thick, comprises, on its inner surface, (a) a sample contact area for contacting a sample, and (b) spacers on the sample contact area;
  ii. the second plate, that is 10 μm to 250 μm thick, comprises, on its inner surface, (a) a sample contact area for contacting a sample, and (b) a sample overflow dam that surrounds the sample contact area is configured to present a sample flow outside of the dam; and
  iii. the hinge that connect the first and the second plates; and
wherein the first and second plate are movable relative to each other around the axis of the hinge.

An embodiment of the Q-Card comprising: a first plate, a second plate, and a hinge, wherein
  i. the first plate, that is about 200 nm to 1500 nm thick, comprises, on its inner surface, a sample contact area for contacting a sample;
  ii. the second plate, that is 10 μm to 250 μm thick, comprises, on its inner surface, (a) a sample contact area for contacting a sample, (b) a sample overflow dam that surrounds the sample contact area is configured to present a sample flow outside of the dam, and (c) spacers on the sample contact area; and
  iii. the hinge that connect the first and the second plates; and
wherein the first and second plate are movable relative to each other around the axis of the hinge.

An embodiment of a method for fabricating the Q-Card of any embodiments of the present disclosure, comprising:
  (a) injection molding of the first plate,
  (b) nanoimprinting or extrusion printing of the second plate.

An embodiment of a method for fabricating the Q-Card of any embodiment of the present disclosure, comprising:
  (a) Laser cutting the first plate,
  (b) nanoimprinting or extrusion printing of the second plate.

An embodiment of a method for fabricating the Q-Card of any embodiments of the present disclosure, comprising:
  (a) Injection molding and laser cutting the first plate,
  (b) nanoimprinting or extrusion printing of the second plate.

An embodiment of a method for fabricating the Q-Card of any embodiment of the present disclosure, comprising: nanoimprinting or extrusion printing to fabricated both the first and the second plate.

An embodiment of a method for fabricating the Q-Card of any embodiment of the present disclosure, comprising: fabricating the first plate or the second plate, using injection molding, laser cutting the first plate, nanoimprinting, extrusion printing, or a combination of thereof.

The method of any embodiment of the present disclosure, wherein the method further comprises a step of attach the hinge on the first and the second plates after the fabrication of the first and second plates.

Compressed Regulated Open Flow" (CROF)

In assaying, a manipulation of a sample or a reagent can lead to improvements in the assaying. The manipulation includes, but not limited to, manipulating the geometric shape and location of a sample and/or a reagent, a mixing or a binding of a sample and a reagent, and a contact area of a sample of reagent to a plate.

Many embodiments of the present invention manipulate the geometric size, location, contact areas, and mixing of a sample and/or a reagent using a method, termed "compressed regulated open flow (CROF)", and a device that performs CROF.

The term "compressed open flow (COF)" refers to a method that changes the shape of a flowable sample deposited on a plate by (i) placing other plate on top of at least a part of the sample and (ii) then compressing the sample between two plates by pushing the two plates towards each other; wherein the compression reduces a thickness of at least a part of the sample and makes the sample flow into open spaces between the plates.

The term "compressed regulated open flow" or "CROF" (or "self-calibrated compressed open flow" or "SCOF" or "SCCOF") refers to a particular type of COF, wherein the final thickness of a part or entire sample after the compression is "regulated" by spacers, wherein the spacers, that are placed between the two plates.

The term "the final thickness of a part or entire sample is regulated by spacers" in a CROF means that during a CROF, once a specific sample thickness is reached, the relative movement of the two plates and hence the change of sample thickness stop, wherein the specific thickness is determined by the spacer.

One embodiment of the method of CROF, as illustrated in Fig. A1, comprises:
  (a) obtaining a sample, that is flowable;
  (b) obtaining a first plate and a second plate that are movable relative to each other into different configurations, wherein each plate has a sample contact surface that is substantially planar, wherein one or both of the plates comprise spacers and the spacers have a predetermined height, and the spacers are on a respective sample contacting surface;

(c) depositing, when the plates are configured in an open configuration, the sample on one or both of the plates; wherein the open configuration is a configuration in which the two plates are either partially or completely separated apart and the spacing between the plates is not regulated by the spacers; and (d) after (c), spreading the sample by bringing the plates into a closed configuration, wherein, in the closed configuration: the plates are facing each other, the spacers and a relevant volume of the sample are between the plates, the thickness of the relevant volume of the sample is regulated by the plates and the spacers, wherein the relevant volume is at least a portion of an entire volume of the sample, and wherein during the sample spreading, the sample flows laterally between the two plates.

The term "plate" refers to, unless being specified otherwise, the plate used in a CROF process, which a solid that has a surface that can be used, together with another plate, to compress a sample placed between the two plate to reduce a thickness of the sample.

The term "the plates" or "the pair of the plates" refers to the two plates in a CROF process.

The term "first plate" or "second plate" refers to the plate use in a CROF process.

The term "the plates are facing each other" refers to the cases where a pair of plates are at least partially facing each other.

The term "spacers" or "stoppers" refers to, unless stated otherwise, the mechanical objects that set, when being placed between two plates, a limit on the minimum spacing between the two plates that can be reached when compressing the two plates together. Namely, in the compressing, the spacers will stop the relative movement of the two plates to prevent the plate spacing becoming less than a preset (i.e. predetermined) value. There are two types of the spacers: "open-spacers" and "enclosed-spacers".

The term "open-spacer" means the spacer have a shape that allows a liquid to flow around the entire perimeter of the spacer and flow pass the spacer. For example, a pillar is an open spacer.

The term of "enclosed spacer" means the spacer of having a shape that a liquid cannot flow abound the entire perimeter of the spacer and cannot flow pass the spacer. For example, a ring shape spacer is an enclosed spacer for a liquid inside the ring, where the liquid inside the ring spacer remains inside the ring and cannot go to outside (outside perimeter).

The term "a spacer has a predetermined height" and "spacers have predetermined inter-spacer distance" means, respectively, that the value of the spacer height and the inter spacer distance is known prior to a CROF process. It is not predetermined, if the value of the spacer height and the inter-spacer distance is not known prior to a CROF process. For example, in the case that beads are sprayed on a plate as spacers, where beads are landed on random locations of the plate, the inter-spacer distance is not predetermined. Another example of not predetermined inter spacer distance is that the spacers moves during a CROF processes.

The term "a spacer is fixed on its respective plate" in a CROF process means that the spacer is attached to a location of a plate and the attachment to that location is maintained during a CROF (i.e. the location of the spacer on respective plate does not change). An example of "a spacer is fixed with its respective plate" is that a spacer is monolithically made of one piece of material of the plate, and the location of the spacer relative to the plate surface does not change during CROF. An example of "a spacer is not fixed with its respective plate" is that a spacer is glued to a plate by an adhesive, but during a use of the plate, during CROF, the adhesive cannot hold the spacer at its original location on the plate surface and the spacer moves away from its original location on the plate surface.

The term "a spacer is fixed to a plate monolithically" means the spacer and the plate behavior like a single piece of an object where, during a use, the spacer does not move or separated from its original location on the plate.

The term "open configuration" of the two plates in a CROF process means a configuration in which the two plates are either partially or completely separated apart and the spacing between the plates is not regulated by the spacers The term "closed configuration" of the two plates in a CROF process means a configuration in which the plates are facing each other, the spacers and a relevant volume of the sample are between the plates, the thickness of the relevant volume of the sample is regulated by the plates and the spacers, wherein the relevant volume is at least a portion of an entire volume of the sample.

The term "a sample thickness is regulated by the plate and the spacers" in a CROF process means that for a give condition of the plates, the sample, the spacer, and the plate compressing method, the thickness of at least a port of the sample at the closed configuration of the plates can be predetermined from the properties of the spacers and the plate.

The term "inner surface" or "sample surface" of a plate in a CROF device refers to the surface of the plate that touches the sample, while the other surface (that does not touch the sample) of the plate is termed "outer surface".

The term "X-Plate" of a CROF device refers to a plate that comprises spaces that are on the sample surface of the plate, wherein the spacers have a predetermined inter-spacer distance and spacer height, and wherein at least one of the spacers is inside the sample contact area.

The term "CROF device" refers to a device that performs a CROF process. The term "CROFed" means that a CROF process is used. For example, the term "a sample was CROFed" means that the sample was put inside a CROF device, a CROF process was performed, and the sample was hold, unless stated otherwise, at a final configuration of the CROF.

The term "CROF plates" refers to the two plates used in performing a CROF process.

The term "surface smoothness" or "surface smoothness variation" of a planar surface refers to the average deviation of a planar surface from a perfect flat plane over a short distance that is about or smaller than a few micrometers. The surface smoothness is different from the surface flatness variation. A planar surface can have a good surface flatness, but poor surface smoothness.

The term "surface flatness" or "surface flatness variation" of a planar surface refers to the average deviation of a planar surface from a perfect flat plane over a long distance that is about or larger than 10 µm. The surface flatness variation is different from the surface smoothness. A planar surface can have a good surface smoothness, but poor surface flatness (i.e. large surface flatness variation).

The term "relative surface flatness" of a plate or a sample is the ratio of the plate surface flatness variation to the final sample thickness.

The term "final sample thickness" in a CROF process refers to, unless specified otherwise, the thickness of the sample at the closed configuration of the plates in a CORF process.

The term "compression method" in CROF refers to a method that brings two plates from an open configuration to a closed configuration.

The term of "interested area" or "area of interest" of a plate refers to the area of the plate that is relevant to the function that the plates perform.

The term "at most" means "equal to or less than". For example, a spacer height is at most 1 µm, it means that the spacer height is equal to or less than 1 µm.

The term "sample area" means the area of the sample in the direction approximately parallel to the space between the plates and perpendicular to the sample thickness.

The term "sample thickness" refers to the sample dimension in the direction normal to the surface of the plates that face each other (e.g., the direction of the spacing between the plates).

The term "plate-spacing" refers to the distance between the inner surfaces of the two plates.

The term "deviation of the final sample thickness" in a CROF means the difference between the predetermined spacer height (determined from fabrication of the spacer) and the average of the final sample thickness, wherein the average final sample thickness is averaged over a given area (e.g. an average of 25 different points (4 mm apart) over 1.6 cm by 1.6 cm area).

The term "uniformity of the measured final sample thickness" in a CROF process means the standard deviation of the measured final sample thickness over a given sample area (e.g. the standard deviation relative to the average).

The term "relevant volume of a sample" and "relevant area of a sample" in a CROF process refers to, respectively, the volume and the area of a portion or entire volume of the sample deposited on the plates during a CROF process, that is relevant to a function to be performed by a respective method or device, wherein the function includes, but not limited to, reduction in binding time of analyte or entity, detection of analytes, quantify of a volume, quantify of a concentration, mixing of reagents, or control of a concentration (analytes, entity or reagents).

The term "some embodiments", "in some embodiments" "in the present invention, in some embodiments", "embodiment", "one embodiment", "another embodiment", "certain embodiments", "many embodiments", or alike refers, unless specifically stated otherwise, to an embodiment(s) that is (are) applied to the entire disclosure (i.e. the entire invention).

The term "height" or "thickness" of an object in a CROF process refers to, unless specifically stated, the dimension of the object that is in the direction normal to a surface of the plate. For example, spacer height is the dimension of the spacer in the direction normal to a surface of the plate, and the spacer height and the spacer thickness means the same thing.

The term "area" of an object in a CROF process refers to, unless specifically stated, the area of the object that is parallel to a surface of the plate. For example, spacer area is the area of the spacer that is parallel to a surface of the plate.

The term "lateral" or "laterally" in a CROF process refers to, unless specifically stated, the direction that is parallel to a surface of the plate.

The term "width" of a spacer in a CROF process refers to, unless specifically stated, a lateral dimension of the spacer.

The term "a spacer inside a sample" means that the spacer is surrounded by the sample (e.g. a pillar spacer inside a sample).

The term "critical bending span" of a plate in a CROF process refers the span (i.e. distance) of the plate between two supports, at which the bending of the plate, for a given flexible plate, sample, and compression force, is equal to an allowed bending. For example, if an allowed bending is 50 nm and the critical bending span is 40 µm for a given flexible plate, sample, and compression force, the bending of the plate between two neighboring spacers 40 µm apart will be 50 nm, and the bending will be less than 50 nm if the two neighboring spacers is less than 40 µm.

The term "flowable" for a sample means that when the thickness of the sample is reduced, the lateral dimension increases. For an example, a stool sample is regarded flowable.

In some embodiments of the present invention, a sample under a CROF process do not to be flowable to benefit from the process, as long as the sample thickness can be reduced under a CROF process. For an example, to stain a tissue by put a dye on a surface of the CROF plate, a CROF process can reduce the tissue thickness and hence speed up the saturation incubation time for staining by the dye.

The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF) that regulate the spacing between the plates. The term "X-plate" refers to one of the two plates in a CROF card, wherein the spacers are fixed to this plate. More descriptions of the COF Card, CROF Card, and X-plate are described in the provisional application Ser. Nos. 62/456,065, filed on Feb. 7, 2017, which is incorporated herein in its entirety for all purposes.

Additional Notes

Further examples of inventive subject matter according to the present disclosure are described in the following enumerated paragraphs.

It must be noted that as used herein and in the appended claims, the singular forms "a", "an", and "the" include plural referents unless the context clearly dictates otherwise, e.g., when the word "single" is used. For example, reference to "an analyte" includes a single analyte and multiple analytes, reference to "a capture agent" includes a single capture agent and multiple capture agents, reference to "a detection agent" includes a single detection agent and multiple detection agents, and reference to "an agent" includes a single agent and multiple agents.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function. Similarly, subject matter that is recited as being configured to perform a particular function may additionally or alternatively be described as being operative to perform that function.

As used herein, the phrase, "for example," the phrase, "as an example," and/or simply the terms "example" and "exemplary" when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

As used herein, the phrases "at least one of" and "one or more of," in reference to a list of more than one entity, means any one or more of the entity in the list of entity, and is not limited to at least one of each and every entity specifically listed within the list of entity. For example, "at least one of A and B" (or, equivalently, "at least one of A or B," or, equivalently, "at least one of A and/or B") may refer to A alone, B alone, or the combination of A and B.

As used herein, the term "and/or" placed between a first entity and a second entity means one of (1) the first entity, (2) the second entity, and (3) the first entity and the second entity. Multiple entity listed with "and/or" should be construed in the same manner, i.e., "one or more" of the entity so conjoined. Other entity may optionally be present other than the entity specifically identified by the "and/or" clause, whether related or unrelated to those entities specifically identified.

Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

One with skill in the art will appreciate that the present invention is not limited in its application to the details of construction, the arrangements of components, category selections, weightings, pre-determined signal limits, or the steps set forth in the description or drawings herein. The invention is capable of other embodiments and of being practiced or being carried out in many different ways.

The practice of various embodiments of the present disclosure employs, unless otherwise indicated, conventional techniques of immunology, biochemistry, chemistry, molecular biology, microbiology, cell biology, genomics and recombinant DNA, which are within the skill of the art. See Green and Sambrook, MOLECULAR CLONING: A LABORATORY MANUAL, 4$^{th}$ edition (2012); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

Related Documents and Additional Examples

The present invention includes a variety of embodiments, which can be combined in multiple ways as long as the various components do not contradict one another. The embodiments should be regarded as a single invention file: each filing has other filing as the references and is also referenced in its entirety and for all purpose, rather than as a discrete independent. These embodiments include not only the disclosures in the current file, but also the documents that are herein referenced, incorporated, or to which priority is claimed.

(1) Definitions

The terms used in describing the devices/apparatus, systems, and methods herein disclosed are defined in the current application, or in PCT Application (designating U.S.) Nos. PCT/US2016/046437 and PCT/US2016/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF card) that regulate the spacing between the plates. The term "X-plate" refers to one of the two plates in a CROF card, wherein the spacers are fixed to this plate. More descriptions of the COF Card, CROF Card, and X-plate are given in the provisional application Ser. No. 62/456,065, filed on Feb. 7, 2017, which is incorporated herein in its entirety for all purposes.

(2) Sample

The devices/apparatus, systems, and methods herein disclosed can be applied to manipulation and detection of various types of samples. The samples are herein disclosed, listed, described, and/or summarized in PCT Application (designating U.S.) Nos. PCT/US2016/046437 and PCT/US2016/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The devices, apparatus, systems, and methods herein disclosed can be used for samples such as but not limited to diagnostic samples, clinical samples, environmental samples and foodstuff samples. The types of sample include but are not limited to the samples listed, described and/or summarized in PCT Application (designating U.S.) Nos. PCT/US2016/046437 and PCT/US2016/051775, which were respectively filed on Aug. 10, 2016 and Sep. 14, 2016, and are hereby incorporated by reference by their entireties.

For example, in some embodiments, the devices, apparatus, systems, and methods herein disclosed are used for a sample that includes cells, tissues, bodily fluids and/or a mixture thereof. In some embodiments, the sample comprises a human body fluid. In some embodiments, the sample comprises at least one of cells, tissues, bodily fluids, stool, amniotic fluid, aqueous humour, vitreous humour, blood, whole blood, fractionated blood, plasma, serum, breast milk, cerebrospinal fluid, cerumen, chyle, chime, endolymph, perilymph, feces, gastric acid, gastric juice, lymph, mucus, nasal drainage, phlegm, pericardial fluid, peritoneal fluid, pleural fluid, pus, rheum, saliva, sebum, semen, sputum, sweat, synovial fluid, tears, vomit, urine, and exhaled breath condensate.

In some embodiments, the devices, apparatus, systems, and methods herein disclosed are used for an environmental sample that is obtained from any suitable source, such as but not limited to: river, lake, pond, ocean, glaciers, icebergs, rain, snow, sewage, reservoirs, tap water, drinking water, etc.; solid samples from soil, compost, sand, rocks, concrete, wood, brick, sewage, etc.; and gaseous samples from the air, underwater heat vents, industrial exhaust, vehicular exhaust, etc. In certain embodiments, the environmental sample is fresh from the source; in certain embodiments, the environmental sample is processed. For example, samples that are not in liquid form are converted to liquid form before the subject devices, apparatus, systems, and methods are applied.

In some embodiments, the devices, apparatus, systems, and methods herein disclosed are used for a foodstuff sample, which is suitable or has the potential to become suitable for animal consumption, e.g., human consumption. In some embodiments, a foodstuff sample includes raw ingredients, cooked or processed food, plant and animal sources of food, preprocessed food as well as partially or fully processed food, etc. In certain embodiments, samples that are not in liquid form are converted to liquid form before the subject devices, apparatus, systems, and methods are applied.

The subject devices, apparatus, systems, and methods can be used to analyze any volume of the sample. Examples of the volumes include, but are not limited to, about 10 mL or less, 5 mL or less, 3 mL or less, 1 microliter ($\mu L$, also "uL" herein) or less, 500 $\mu L$ or less, 300 $\mu L$ or less, 250 $\mu L$ or less, 200 $\mu L$ or less, 170 $\mu L$ or less, 150 $\mu L$ or less, 125 $\mu L$ or less, 100 $\mu L$ or less, 75 $\mu L$ or less, 50 $\mu L$ or less, 25 $\mu L$ or less, 20 $\mu L$ or less, 15 $\mu L$ or less, 10 $\mu L$ or less, 5 $\mu L$ or less, 3 $\mu L$ or less, 1 $\mu L$ or less, 0.5 $\mu L$ or less, 0.1 $\mu L$ or less, 0.05 $\mu L$ or less, 0.001 $\mu L$ or less, 0.0005 $\mu L$ or less, 0.0001 $\mu L$ or less, 10 $\mu L$ or less, 1 $\mu L$ or less, or a range between any two of the values.

In some embodiments, the volume of the sample includes, but is not limited to, about 100 $\mu L$ or less, 75 $\mu L$ or less, 50 $\mu L$ or less, 25 $\mu L$ or less, 20 $\mu L$ or less, 15 $\mu L$ or less, 10 $\mu L$ or less, 5 $\mu L$ or less, 3 $\mu L$ or less, 1 $\mu L$ or less, 0.5 $\mu L$ or less, 0.1 $\mu L$ or less, 0.05 $\mu L$ or less, 0.001 $\mu L$ or less, 0.0005 $\mu L$ or less, 0.0001 $\mu L$ or less, 10 $\mu L$ or less, 1 $\mu L$ or less, or a range between any two of the values. In some embodiments, the volume of the sample includes, but is not limited to, about 10 $\mu L$ or less, 5 $\mu L$ or less, 3 $\mu L$ or less, 1 $\mu L$ or less, 0.5 $\mu L$ or less, 0.1 $\mu L$ or less, 0.05 $\mu L$ or less, 0.001 $\mu L$ or less, 0.0005 $\mu L$ or less, 0.0001 $\mu L$ or less, 10 $\mu L$ or less, 1 $\mu L$ or less, or a range between any two of the values.

In some embodiments, the amount of the sample is about a drop of liquid. In certain embodiments, the amount of sample is the amount collected from a pricked finger or fingerstick. In certain embodiments, the amount of sample is the amount collected from a microneedle, micropipette or a venous draw.

In certain embodiments, the sample holder is configured to hold a fluidic sample. In certain embodiments, the sample holder is configured to compress at least part of the fluidic sample into a thin layer. In certain embodiments, the sample holder comprises structures that are configured to heat and/or cool the sample. In certain embodiments, the heating source provides electromagnetic waves that can be absorbed by certain structures in the sample holder to change the temperature of the sample. In certain embodiments, the signal sensor is configured to detect and/or measure a signal from the sample. In certain embodiments, the signal sensor is configured to detect and/or measure an analyte in the sample. In certain embodiments, the heat sink is configured to absorb heat from the sample holder and/or the heating source. In certain embodiments, the heat sink comprises a chamber that at least partly enclose the sample holder.

(3) Q-Card, Spacers and Uniform Sample Thickness

The devices/apparatus, systems, and methods herein disclosed can include or use Q-cards, spacers, and uniform sample thickness embodiments for sample detection, analysis, and quantification. In some embodiments, the Q-card comprises spacers, which help to render at least part of the sample into a layer of high uniformity. The structure, material, function, variation and dimension of the spacers, as well as the uniformity of the spacers and the sample layer, are herein disclosed, listed, described, and/or summarized in PCT Application (designating U.S.) Nos. PCT/US2016/046437 and PCT/US2016/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The term "open configuration" of the two plates in a QMAX process means a configuration in which the two plates are either partially or completely separated apart and the spacing between the plates is not regulated by the spacers The term "closed configuration" of the two plates in a QMAX process means a configuration in which the plates are facing each other, the spacers and a relevant volume of the sample are between the plates, the relevant spacing between the plates, and thus the thickness of the relevant volume of the sample, is regulated by the plates and the spacers, wherein the relevant volume is at least a portion of an entire volume of the sample.

The term "a sample thickness is regulated by the plate and the spacers" in a QMAX process means that for a give condition of the plates, the sample, the spacer, and the plate compressing method, the thickness of at least a port of the sample at the closed configuration of the plates can be predetermined from the properties of the spacers and the plate.

The term "inner surface" or "sample surface" of a plate in a QMAX card refers to the surface of the plate that touches the sample, while the other surface (that does not touch the sample) of the plate is termed "outer surface".

The term "height" or "thickness" of an object in a QMAX process refers to, unless specifically stated, the dimension of the object that is in the direction normal to a surface of the plate. For example, spacer height is the dimension of the spacer in the direction normal to a surface of the plate, and the spacer height and the spacer thickness means the same thing.

The term "area" of an object in a QMAX process refers to, unless specifically stated, the area of the object that is parallel to a surface of the plate. For example, spacer area is the area of the spacer that is parallel to a surface of the plate.

The term of QMAX card refers the device that perform a QMAX (e.g. CROF) process on a sample, and have or not have a hinge that connect the two plates.

The term "QMAX card with a hinge and "QMAX card" are interchangeable.

The term "angle self-maintain", "angle self-maintaining", or "rotation angle self-maintaining" refers to the property of the hinge, which substantially maintains an angle between the two plates, after an external force that moves the plates from an initial angle into the angle is removed from the plates.

In using QMAX card, the two plates need to be open first for sample deposition. However, in some embodiments, the QMAX card from a package has the two plates are in contact each other (e.g. a close position), and to separate them is challenges, since one or both plates are very thing. To facilitate an opening of the QMAX card, opening notch or notches are created at the edges or corners of the first plate or both places, and, at the close position of the plates, a part of the second plate placed over the opening notch, hence in the notch of the first plate, the second plate can be lifted open without a blocking of the first plate.

In the QMAX assay platform, a QMAX card uses two plates to manipulate the shape of a sample into a thin layer (e.g. by compressing). In certain embodiments, the plate manipulation needs to change the relative position (termed: plate configuration) of the two plates several times by human hands or other external forces. There is a need to design the QMAX card to make the hand operation easy and fast.

In QMAX assays, one of the plate configurations is an open configuration, wherein the two plates are completely or partially separated (the spacing between the plates is not controlled by spacers) and a sample can be deposited. Another configuration is a closed configuration, wherein at least part of the sample deposited in the open configuration is compressed by the two plates into a layer of highly uniform thickness, the uniform thickness of the layer is confined by the inner surfaces of the plates and is regulated by the plates and the spacers. In some embodiments, the average spacing between the two plates is more than 300 µm.

In a QMAX assay operation, an operator needs to first make the two plates to be in an open configuration ready for sample deposition, then deposit a sample on one or both of the plates, and finally close the plates into a close position. In certain embodiments, the two plates of a QMAX card are initially on top of each other and need to be separated to get into an open configuration for sample deposition. When one of the plate is a thin plastic film (175 µm thick PMA), such separation can be difficult to perform by hand. The present invention intends to provide the devices and methods that make the operation of certain assays, such as the QMAX card assay, easy and fast.

In some embodiments, the QMAX device comprises a hinge that connect two or more plates together, so that the plates can open and close in a similar fashion as a book. In some embodiments, the material of the hinge is such that the hinge can self-maintain the angle between the plates after adjustment. In some embodiments, the hinge is configured to maintain the QMAX card in the closed configuration, such that the entire QMAX card can be slide in and slide out a card slot without causing accidental separation of the two plates. In some embodiments, the QMAX device comprises one or more hinges that can control the rotation of more than two plates.

In some embodiments, the hinge is made from a metallic material that is selected from a group consisting of gold, silver, copper, aluminum, iron, tin, platinum, nickel, cobalt, alloys, or any combination of thereof. In some embodiments, the hinge comprises a single layer, which is made from a polymer material, such as but not limited to plastics. The polymer material is selected from the group consisting of acrylate polymers, vinyl polymers, olefin polymers, cellulosic polymers, noncellulosic polymers, polyester polymers, Nylon, cyclic olefin copolymer (COC), poly(methyl methacrylate) (PMMB), polycarbonate (PC), cyclic olefin polymer (COP), liquid crystalline polymer (LCP), polyimide (PB), polyethylene (PE), polyimide (PI), polypropylene (PP), poly(phenylene ether) (PPE), polystyrene (PS), polyoxymethylene (POM), polyether ether ketone (PEEK), polyether sulfone (PES), poly(ethylene phthalate) (PET), polytetrafluoroethylene (PTFE), polyvinyl chloride (PVC), polyvinylidene fluoride (PVDF), polybutylene terephthalate (PBT), fluorinated ethylene propylene (FEP), perfluoroalkoxyalkane (PFB), polydimethylsiloxane (PDMS), rubbers, or any combinations of thereof. In some embodiments, the polymer material is selected from polystyrene, PMMB, PC, COC, COP, other plastic, or any combination of thereof.

In essence, the term "spacers" or "stoppers" refers to, unless stated otherwise, the mechanical objects that set, when being placed between two plates, a limit on the minimum spacing between the two plates that can be reached when compressing the two plates together. Namely, in the compressing, the spacers will stop the relative movement of the two plates to prevent the plate spacing becoming less than a preset (i.e. predetermined) value.

The term "a spacer has a predetermined height" and "spacers have a predetermined inter-spacer distance" means, respectively, that the value of the spacer height and the inter spacer distance is known prior to a QMAX process. It is not predetermined, if the value of the spacer height and the inter-spacer distance is not known prior to a QMAX process. For example, in the case that beads are sprayed on a plate as spacers, where beads are landed at random locations of the plate, the inter-spacer distance is not predetermined. Another example of not predetermined inter spacer distance is that the spacers moves during a QMAX processes.

The term "a spacer is fixed on its respective plate" in a QMAX process means that the spacer is attached to a location of a plate and the attachment to that location is maintained during a QMAX (i.e. the location of the spacer on respective plate does not change) process. An example of "a spacer is fixed with its respective plate" is that a spacer is monolithically made of one piece of material of the plate, and the location of the spacer relative to the plate surface does not change during the QMAX process. An example of "a spacer is not fixed with its respective plate" is that a spacer is glued to a plate by an adhesive, but during a use of the plate, during the QMAX process, the adhesive cannot hold the spacer at its original location on the plate surface and the spacer moves away from its original location on the plate surface.

In some embodiments, human hands can be used to press the plates into a closed configuration; In some embodiments, human hands can be used to press the sample into a thin layer. The manners in which hand pressing is employed are described and/or summarized in PCT Application (designating U.S.) Nos. PCT/US2016/046437 filed on Aug. 10, 2016 and PCT/US2016/051775 filed on Sep. 14, 2016, and in US Provisional Application Nos. 62/431,639 filed on Dec. 9, 2016, 62/456,287 filed on Feb. 8, 2017, 62/456,065 filed on Feb. 7, 2017, 62/456,504 filed on Feb. 8, 2017, and 62/460,062 filed on Feb. 16, 2017, which are all hereby incorporated by reference by their entireties.

In some embodiments, human hand can be used to manipulate or handle the plates of the QMAX device. In certain embodiments, the human hand can be used to apply an imprecise force to compress the plates from an open configuration to a closed configuration. In certain embodiments, the human hand can be used to apply an imprecise force to achieve high level of uniformity in the thickness of the sample (e.g. less than 5%, 10%, 15%, or 20% variability).

(4) Hinges, Opening Notches, Recessed Edge and Sliders

The devices/apparatus, systems, and methods herein disclosed can include or use Q-cards for sample detection, analysis, and quantification. In some embodiments, the Q-card comprises hinges, notches, recesses, and sliders, which help to facilitate the manipulation of the Q card and the measurement of the samples. The structure, material, function, variation and dimension of the hinges, notches, recesses, and sliders are herein disclosed, listed, described, and/or summarized in PCT Application (designating U.S.) Nos. PCT/US2016/046437 and PCT/US2016/051775, which were respectively filed on Aug. 10, 2016 and Sep. 14, 2016, U.S. Provisional Application No. 62/431,639, which was filed on Dec. 9, 2016, U.S. Provisional Application No. 62/456,065, which was filed on Feb. 7, 2017, U.S. Provisional Application Nos. 62/456,287 and 62/456,504, which was filed on Feb. 8, 2017, and U.S. Provisional Application No. 62/539,660, which was filed on Aug. 1, 2017, all of which applications are incorporated herein in their entireties for all purposes.

In some embodiments, the QMAX device comprises opening mechanisms such as but not limited to notches on plate edges or strips attached to the plates, making is easier for a user to manipulate the positioning of the plates, such as but not limited to separating the plates of by hand.

In some embodiments, the QMAX device comprises trenches on one or both of the plates. In certain embodiments, the trenches limit the flow of the sample on the plate.

(5) Q-Card and Adaptor

The devices/apparatus, systems, and methods herein disclosed can include or use Q-cards for sample detection, analysis, and quantification. In some embodiments, the Q-card is used together with an adaptor that is configured to accommodate the Q-card and connect to a mobile device so that the sample in the Q-card can be imaged, analyzed, and/or measured by the mobile device. The structure, material, function, variation, dimension and connection of the Q-card, the adaptor, and the mobile are herein disclosed, listed, described, and/or summarized in PCT Application (designating U.S.) Nos. PCT/US2016/046437 and PCT/US2016/051775, which were respectively filed on Aug. 10, 2016 and Sep. 14, 2016, U.S. Provisional Application No. 62/456,065, which was filed on Feb. 7, 2017, U.S. Provisional Application Nos. 62/456,287 and 62/456,590, which were filed on Feb. 8, 2017, U.S. Provisional Application No. 62/456,504, which was filed on Feb. 8, 2017, U.S. Provisional Application No. 62/459,544, which was filed on Feb. 15, 2017, and U.S. Provisional Application Nos. 62/460,075 and 62/459,920, which were filed on Feb. 16, 2017, all of which applications are incorporated herein in their entireties for all purposes.

In some embodiments, the adaptor comprises a receptacle slot, which is configured to accommodate the QMAX device when the device is in a closed configuration. In certain embodiments, the QMAX device has a sample deposited therein and the adaptor can be connected to a mobile device (e.g. a smartphone) so that the sample can be read by the mobile device. In certain embodiments, the mobile device can detect and/or analyze a signal from the sample. In certain embodiments, the mobile device can capture images of the sample when the sample is in the QMAX device and positioned in the field of view (FOV) of a camera, which in certain embodiments, is part of the mobile device.

In some embodiments, the adaptor comprises optical components, which are configured to enhance, magnify, and/or optimize the production of the signal from the sample. In some embodiments, the optical components include parts that are configured to enhance, magnify, and/or optimize illumination provided to the sample. In certain embodiments, the illumination is provided by a light source that is part of the mobile device. In some embodiments, the optical components include parts that are configured to enhance, magnify, and/or optimize a signal from the sample.

(6) Smartphone Detection System

The devices/apparatus, systems, and methods herein disclosed can include or use Q-cards for sample detection, analysis, and quantification. In some embodiments, the Q-card is used together with an adaptor that can connect the Q-card with a smartphone detection system. In some embodiments, the smartphone comprises a camera and/or an illumination source The smartphone detection system, as well the associated hardware and software are herein disclosed, listed, described, and/or summarized in PCT Application (designating U.S.) Nos. PCT/US2016/046437 and PCT/US2016/051775, which were respectively filed on Aug. 10, 2016 and Sep. 14, 2016, U.S. Provisional Application No. 62/456,065, which was filed on Feb. 7, 2017, U.S. Provisional Application Nos. 62/456,287 and 62/456,590, which were filed on Feb. 8, 2017, U.S. Provisional Application No. 62/456,504, which was filed on Feb. 8, 2017, U.S. Provisional Application No. 62/459,544, which was filed on Feb. 15, 2017, and U.S. Provisional Application Nos. 62/460,075 and 62/459,920, which were filed on Feb. 16, 2017, all of which applications are incorporated herein in their entireties for all purposes.

In some embodiments, the smartphone comprises a camera, which can be used to capture images or the sample when the sample is positioned in the field of view of the camera (e.g. by an adaptor). In certain embodiments, the camera includes one set of lenses (e.g. as in iPhone™ 6). In certain embodiments, the camera includes at least two sets of lenses (e.g. as in iPhone™ 7). In some embodiments, the smartphone comprises a camera, but the camera is not used for image capturing.

In some embodiments, the smartphone comprises a light source such as but not limited to LED (light emitting diode). In certain embodiments, the light source is used to provide illumination to the sample when the sample is positioned in the field of view of the camera (e.g. by an adaptor). In some embodiments, the light from the light source is enhanced, magnified, altered, and/or optimized by optical components of the adaptor.

In some embodiments, the smartphone comprises a processor that is configured to process the information from the sample. The smartphone includes software instructions that, when executed by the processor, can enhance, magnify, and/or optimize the signals (e.g. images) from the sample. The processor can include one or more hardware components, such as a central processing unit (CPU), an application-specific integrated circuit (ASIC), an application-specific instruction-set processor (ASIP), a graphics processing unit (GPU), a physics processing unit (PPU), a digital signal processor (DSP), a field-programmable gate array (FPGA), a programmable logic device (PLD), a controller, a microcontroller unit, a reduced instruction-set computer (RISC), a microprocessor, or the like, or any combination thereof.

In some embodiments, the smartphone comprises a communication unit, which is configured and/or used to transmit data and/or images related to the sample to another device. Merely by way of example, the communication unit can use a cable network, a wireline network, an optical fiber network, a telecommunications network, an intranet, the Internet, a local area network (LAN), a wide area network (WAN), a wireless local area network (WLAN), a metropolitan area network (MAN), a wide area network (WAN), a public telephone switched network (PSTN), a Bluetooth network, a ZigBee network, a near field communication (NFC) network, or the like, or any combination thereof.

In some embodiments, the smartphone is an iPhone™, an Android™ phone, or a Windows™ phone.

(7) Detection Methods

The devices/apparatus, systems, and methods herein disclosed can include or be used in various types of detection methods. The detection methods are herein disclosed, listed, described, and/or summarized in PCT Application (designating U.S.) Nos. PCT/US2016/046437 and PCT/US2016/051775, which were respectively filed on Aug. 10, 2016 and Sep. 14, 2016, U.S. Provisional Application No. 62/456,065, which was filed on Feb. 7, 2017, U.S. Provisional Application Nos. 62/456,287, 62/456,528, 62/456,631, 62/456,522, 62/456,598, 62/456,603, and 62/456,628, which were filed on Feb. 8, 2017, U.S. Provisional Application Nos. 62/459,276, 62/456,904, 62/457,075, and 62/457,009, which were filed on Feb. 9, 2017, and U.S. Provisional Application Nos. 62/459,303, 62/459,337, and 62/459,598, which were filed on Feb. 15, 2017, and U.S. Provisional Application Nos. 62/460,083, 62/460,076, which were filed on Feb. 16, 2017, all of which applications are incorporated herein in their entireties for all purposes.

(8) Labels, Capture Agent and Detection Agent

The devices/apparatus, systems, and methods herein disclosed can employ various types of labels, capture agents, and detection agents that are used for analytes detection. The labels are herein disclosed, listed, described, and/or summarized in PCT Application (designating U.S.) Nos. PCT/US2016/046437 and PCT/US2016/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

In some embodiments, the label is optically detectable, such as but not limited to a fluorescence label. In some embodiments, the labels include, but are not limited to, IRDye800CW, Alexa 790, Dylight 800, fluorescein, fluorescein isothiocyanate, succinimidyl esters of carboxyfluorescein, succinimidyl esters of fluorescein, 5-isomer of fluorescein dichlorotriazine, caged carboxyfluorescein-alanine-carboxamide, Oregon Green 488, Oregon Green 514; Lucifer Yellow, acridine Orange, rhodamine, tetramethylrhodamine, Texas Red, propidium iodide, JC-1 (5,5',6,6'-tetrachloro-1,1',3,3'-tetraethylbenzimidazoylcarbocyanine iodide), tetrabromorhodamine 123, rhodamine 6G, TMRM (tetramethyl rhodamine methyl ester), TMRE (tetramethyl rhodamine ethyl ester), tetramethylrosamine, rhodamine B and 4-dimethylaminotetramethylrosamine, green fluorescent protein, blue-shifted green fluorescent protein, cyan-shifted green fluorescent protein, red-shifted green fluorescent protein, yellow-shifted green fluorescent protein, 4-acetamido-4'-isothiocyanatostilbene-2,2'disulfonic acid; acridine and derivatives, such as acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; 4,4-difluoro-5-(2-thienyl)-4-bora-3a,4a diaza-5-indacene-3-propioni-c acid BODIPY; cascade blue; Brilliant Yellow; coumarin and derivatives: coumarin, 7-amino-4-methylcoumarin (AMC, Coumarin 120), 7-amino-4-trifluoromethylcoumarin (Coumarin 151); cyanine dyes; cyanosine; 4',6-diaminidino-2-phenylindole (DAPI); 5',5"-dibromopyrogallol-sulfonaphthalein (Bromopyrogallol Red); 7-diethylamino-3-(4'-isothiocyanatophenyl)-4-methylcoumarin; diethylenetriaamine pentaacetate; 4,4'-diisothiocyanatodihydro-stilbene-2-,2'-disulfonic acid; 4,4'-diisothiocyanatostilbene-2,2'-disulfonic acid; 5-(dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM), 5-(4,6-dichlorotriazin-2-yl)amino- -fluorescein (DTAF), 2',7'dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; ophthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl hodamine isothiocyanate (TRITC); riboflavin; 5-(2'-aminoethyl) aminonaphthalene-1-sulfonic acid (EDANS), 4-(4'-dimethylaminophenylazo)benzoic acid (DABCYL), rosolic acid; CAL Fluor Orange 560; terbium chelate derivatives; Cy 3; Cy 5; Cy 5.5; Cy 7; IRD 700; IRD 800; La Jolla Blue; phthalo cyanine; and naphthalo cyanine, coumarins and related dyes, xanthene dyes such as rhodols, resorufins, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, fluorescent europium and terbium complexes; combinations thereof, and the like. Suitable fluorescent proteins and chromogenic proteins include, but are not limited to, a green fluorescent protein (GFP), including, but not limited to, a GFP derived from *Aequoria victoria* or a derivative thereof, e.g., a "humanized" derivative such as Enhanced GFP; a GFP from another species such as *Renilla reniformis, Renilla mulleri,* or *Ptilosarcus guernyi*; "humanized" recombinant GFP (hrGFP); any of a variety of fluorescent and colored proteins from *Anthozoan* species; combinations thereof; and the like.

In any embodiment, the QMAX device can contain a plurality of capture agents and/or detection agents that each bind to a biomarker selected from Tables B1, B2, B3 and/or B7 in U.S. Provisional Application No. 62/234,538 and/or PCT Application No. PCT/US2016/054025, wherein the reading step d) includes obtaining a measure of the amount of the plurality of biomarkers in the sample, and wherein the amount of the plurality of biomarkers in the sample is diagnostic of a disease or condition.

In any embodiment, the capture agent and/or detection agents can be an antibody epitope and the biomarker can be an antibody that binds to the antibody epitope. In some embodiments, the antibody epitope includes a biomolecule, or a fragment thereof, selected from Tables B4, B5 or B6 in U.S. Provisional Application No. 62/234,538 and/or PCT Application No. PCT/US2016/054025. In some embodiments, the antibody epitope includes an allergen, or a fragment thereof, selected from Table B5. In some embodiments, the antibody epitope includes an infectious agent-derived biomolecule, or a fragment thereof, selected from Table B6 in U.S. Provisional Application No. 62/234,538 and/or PCT Application No. PCT/US2016/054025.

In any embodiment, the QMAX device can contain a plurality of antibody epitopes selected from Tables B4, B5 and/or B6 in U.S. Provisional Application No. 62/234,538 and/or PCT Application No. PCT/US2016/054025, wherein the reading step d) includes obtaining a measure of the amount of a plurality of epitope-binding antibodies in the sample, and wherein the amount of the plurality of epitope-binding antibodies in the sample is diagnostic of a disease or condition.

(9) Analytes

The devices/apparatus, systems, and methods herein disclosed can be applied to manipulation and detection of various types of analytes (including biomarkers). The analytes are herein disclosed, listed, described, and/or summarized in PCT Application (designating U.S.) Nos. PCT/US2016/046437 and PCT/US2016/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The devices, apparatus, systems, and methods herein disclosed can be used for the detection, purification and/or quantification of various analytes. In some embodiments, the analytes are biomarkers that associated with various diseases. In some embodiments, the analytes and/or biomarkers are indicative of the presence, severity, and/or stage of the diseases. The analytes, biomarkers, and/or diseases that can be detected and/or measured with the devices, apparatus, systems, and/or method of the present invention include the analytes, biomarkers, and/or diseases listed, described and/or summarized in PCT Application (designating U.S.) Nos. PCT/US2016/046437 filed on Aug. 10, 2016, and PCT Application No. PCT/US2016/054025 filed on Sep. 27, 2016, and U.S. Provisional Application Nos. 62/234,538 filed on Sep. 29, 2015, 62/233,885 filed on Sep. 28, 2015, 62/293,188 filed on Feb. 9, 2016, and 62/305,123 filed on Mar. 8, 2016, which are all hereby incorporated by reference by their entireties. For example, the devices, apparatus, systems, and methods herein disclosed can be used in (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., virus, fungus and bacteria from environment, e.g., water, soil, or biological samples, e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., during synthesis or purification of pharmaceuticals.

In some embodiments, the analyte can be a biomarker, an environmental marker, or a foodstuff marker. The sample in some instances is a liquid sample, and can be a diagnostic sample (such as saliva, serum, blood, sputum, urine, sweat, lacrima, semen, or mucus); an environmental sample obtained from a river, ocean, lake, rain, snow, sewage, sewage processing runoff, agricultural runoff, industrial runoff, tap water or drinking water; or a foodstuff sample obtained from tap water, drinking water, prepared food, processed food or raw food.

In any embodiment, the sample can be a diagnostic sample obtained from a subject, the analyte can be a biomarker, and the measured the amount of the analyte in the sample can be diagnostic of a disease or a condition.

In any embodiment, the devices, apparatus, systems, and methods in the present invention can further include diagnosing the subject based on information including the measured amount of the biomarker in the sample. In some cases, the diagnosing step includes sending data containing the measured amount of the biomarker to a remote location and receiving a diagnosis based on information including the measurement from the remote location.

In any embodiment, the biomarker can be selected from Tables B1, 2, 3 or 7 as disclosed in U.S. Provisional Application Nos. 62/234,538, 62/293,188, and/or 62/305,123, and/or PCT Application No. PCT/US2016/054,025, which are all incorporated in their entireties for all purposes. In some instances, the biomarker is a protein selected from Tables B1, 2, or 3. In some instances, the biomarker is a nucleic acid selected from Tables B2, 3 or 7. In some instances, the biomarker is an infectious agent-derived biomarker selected from Table B2. In some instances, the biomarker is a microRNA (miRNA) selected from Table B7.

In any embodiment, the applying step b) can include isolating miRNA from the sample to generate an isolated miRNA sample, and applying the isolated miRNA sample to the disk-coupled dots-on-pillar antenna (QMAX device) array.

In any embodiment, the QMAX device can contain a plurality of capture agents that each bind to a biomarker selected from Tables B1, B2, B3 and/or B7, wherein the reading step d) includes obtaining a measure of the amount of the plurality of biomarkers in the sample, and wherein the amount of the plurality of biomarkers in the sample is diagnostic of a disease or condition.

In any embodiment, the capture agent can be an antibody epitope and the biomarker can be an antibody that binds to the antibody epitope. In some embodiments, the antibody epitope includes a biomolecule, or a fragment thereof, selected from Tables B4, B5 or B6. In some embodiments, the antibody epitope includes an allergen, or a fragment thereof, selected from Table B5. In some embodiments, the antibody epitope includes an infectious agent-derived biomolecule, or a fragment thereof, selected from Table B6.

In any embodiment, the QMAX device can contain a plurality of antibody epitopes selected from Tables B4, B5 and/or B6, wherein the reading step d) includes obtaining a measure of the amount of a plurality of epitope-binding antibodies in the sample, and wherein the amount of the plurality of epitope-binding antibodies in the sample is diagnostic of a disease or condition.

In any embodiment, the sample can be an environmental sample, and wherein the analyte can be an environmental marker. In some embodiments, the environmental marker is selected from Table B8 in U.S. Provisional Application No. 62/234,538 and/or PCT Application No. PCT/US2016/054025.

In any embodiment, the method can include receiving or providing a report that indicates the safety or harmfulness for a subject to be exposed to the environment from which the sample was obtained.

In any embodiment, the method can include sending data containing the measured amount of the environmental marker to a remote location and receiving a report that indicates the safety or harmfulness for a subject to be exposed to the environment from which the sample was obtained.

In any embodiment, the QMAX device array can include a plurality of capture agents that each binds to an environmental marker selected from Table B8, and wherein the reading step d) can include obtaining a measure of the amount of the plurality of environmental markers in the sample.

In any embodiment, the sample can be a foodstuff sample, wherein the analyte can be a foodstuff marker, and wherein the amount of the foodstuff marker in the sample can correlate with safety of the foodstuff for consumption. In some embodiments, the foodstuff marker is selected from Table B9.

In any embodiment, the method can include receiving or providing a report that indicates the safety or harmfulness for a subject to consume the foodstuff from which the sample is obtained.

In any embodiment, the method can include sending data containing the measured amount of the foodstuff marker to a remote location and receiving a report that indicates the safety or harmfulness for a subject to consume the foodstuff from which the sample is obtained.

In any embodiment, the devices, apparatus, systems, and methods herein disclosed can include a plurality of capture agents that each binds to a foodstuff marker selected from Table B9 from in U.S. Provisional Application No. 62/234,538 and PCT Application No. PCT/US2016/054025, wherein the obtaining can include obtaining a measure of the amount of the plurality of foodstuff markers in the sample, and wherein the amount of the plurality of foodstuff marker in the sample can correlate with safety of the foodstuff for consumption.

Also provided herein are kits that find use in practicing the devices, systems and methods in the present invention.

The amount of sample can be about a drop of a sample. The amount of sample can be the amount collected from a pricked finger or fingerstick. The amount of sample can be the amount collected from a microneedle or a venous draw.

A sample can be used without further processing after obtaining it from the source, or can be processed, e.g., to enrich for an analyte of interest, remove large particulate matter, dissolve or resuspend a solid sample, etc.

Any suitable method of applying a sample to the QMAX device can be employed. Suitable methods can include using a pipet, dropper, syringe, etc. In certain embodiments, when the QMAX device is located on a support in a dipstick format, as described below, the sample can be applied to the QMAX device by dipping a sample-receiving area of the dipstick into the sample.

A sample can be collected at one time, or at a plurality of times. Samples collected over time can be aggregated and/or processed (by applying to a QMAX device and obtaining a measurement of the amount of analyte in the sample, as described herein) individually. In some instances, measurements obtained over time can be aggregated and can be useful for longitudinal analysis over time to facilitate screening, diagnosis, treatment, and/or disease prevention.

Washing the QMAX device to remove unbound sample components can be done in any convenient manner, as described above. In certain embodiments, the surface of the QMAX device is washed using binding buffer to remove unbound sample components.

Detectable labeling of the analyte can be done by any convenient method. The analyte can be labeled directly or indirectly. In direct labeling, the analyte in the sample is labeled before the sample is applied to the QMAX device. In indirect labeling, an unlabeled analyte in a sample is labeled after the sample is applied to the QMAX device to capture the unlabeled analyte, as described below.

(10) Applications

The devices/apparatus, systems, and methods herein disclosed can be used for various applications (fields and samples). The applications are herein disclosed, listed, described, and/or summarized in PCT Application (designating U.S.) Nos. PCT/US2016/046437 and PCT/US2016/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

In some embodiments, the devices, apparatus, systems, and methods herein disclosed are used in a variety of different application in various field, wherein determination of the presence or absence, quantification, and/or amplification of one or more analytes in a sample are desired. For example, in certain embodiments the subject devices, apparatus, systems, and methods are used in the detection of proteins, peptides, nucleic acids, synthetic compounds, inorganic compounds, organic compounds, bacteria, virus, cells, tissues, nanoparticles, and other molecules, compounds, mixtures and substances thereof. The various fields in which the subject devices, apparatus, systems, and methods can be used include, but are not limited to: diagnostics, management, and/or prevention of human diseases and conditions, diagnostics, management, and/or prevention of veterinary diseases and conditions, diagnostics, management, and/or prevention of plant diseases and conditions, agricultural uses, veterinary uses, food testing, environments testing and decontamination, drug testing and prevention, and others.

The applications of the present invention include, but are not limited to: (a) the detection, purification, quantification, and/or amplification of chemical compounds or biomolecules that correlates with certain diseases, or certain stages of the diseases, e.g., infectious and parasitic disease, injuries, cardiovascular disease, cancer, mental disorders, neuropsychiatric disorders and organic diseases, e.g., pulmonary diseases, renal diseases, (b) the detection, purification, quantification, and/or amplification of cells and/or microorganism, e.g., virus, fungus and bacteria from the environment, e.g., water, soil, or biological samples, e.g., tissues, bodily fluids, (c) the detection, quantification of chemical compounds or biological samples that pose hazard to food safety, human health, or national security, e.g. toxic waste, anthrax, (d) the detection and quantification of vital parameters in medical or physiological monitor, e.g., glucose, blood oxygen level, total blood count, (e) the detection and quantification of specific DNA or RNA from biological samples, e.g., cells, viruses, bodily fluids, (f) the sequencing and comparing of genetic sequences in DNA in the chromosomes and mitochondria for genome analysis or (g) the detection and quantification of reaction products, e.g., during synthesis or purification of pharmaceuticals.

In some embodiments, the subject devices, apparatus, systems, and methods are used in the detection of nucleic acids, proteins, or other molecules or compounds in a sample. In certain embodiments, the devices, apparatus, systems, and methods are used in the rapid, clinical detection and/or quantification of one or more, two or more, or three or more disease biomarkers in a biological sample, e.g., as being employed in the diagnosis, prevention, and/or management of a disease condition in a subject. In certain embodiments, the devices, apparatus, systems, and methods are used in the detection and/or quantification of one or more, two or more, or three or more environmental markers in an environmental sample, e.g. sample obtained from a river, ocean, lake, rain, snow, sewage, sewage processing runoff, agricultural runoff, industrial runoff, tap water or drinking water. In certain embodiments, the devices, apparatus, systems, and methods are used in the detection and/or quantification of one or more, two or more, or three or more foodstuff marks from a food sample obtained from tap water, drinking water, prepared food, processed food or raw food.

In some embodiments, the subject device is part of a microfluidic device. In some embodiments, the subject devices, apparatus, systems, and methods are used to detect a fluorescence or luminescence signal. In some embodiments, the subject devices, apparatus, systems, and methods include, or are used together with, a communication device, such as but not limited to: mobile phones, tablet computers and laptop computers. In some embodiments, the subject devices, apparatus, systems, and methods include, or are used together with, an identifier, such as but not limited to an optical barcode, a radio frequency ID tag, or combinations thereof.

In some embodiments, the sample is a diagnostic sample obtained from a subject, the analyte is a biomarker, and the measured amount of the analyte in the sample is diagnostic of a disease or a condition. In some embodiments, the subject devices, systems and methods further include receiving or providing to the subject a report that indicates the measured amount of the biomarker and a range of measured values for the biomarker in an individual free of or at low risk of having the disease or condition, wherein the measured amount of the biomarker relative to the range of measured values is diagnostic of a disease or condition.

In some embodiments, the sample is an environmental sample, and wherein the analyte is an environmental marker. In some embodiments, the subject devices, systems and methods includes receiving or providing a report that indicates the safety or harmfulness for a subject to be exposed to the environment from which the sample was obtained. In some embodiments, the subject devices, systems and methods include sending data containing the measured amount of the environmental marker to a remote location and receiving a report that indicates the safety or harmfulness for a subject to be exposed to the environment from which the sample was obtained.

In some embodiments, the sample is a foodstuff sample, wherein the analyte is a foodstuff marker, and wherein the amount of the foodstuff marker in the sample correlate with safety of the foodstuff for consumption. In some embodiments, the subject devices, systems and methods include receiving or providing a report that indicates the safety or harmfulness for a subject to consume the foodstuff from which the sample is obtained. In some embodiments, the subject devices, systems and methods include sending data containing the measured amount of the foodstuff marker to a remote location and receiving a report that indicates the safety or harmfulness for a subject to consume the foodstuff from which the sample is obtained.

(11) Dimensions

The devices, apparatus, systems, and methods herein disclosed can include or use a QMAX device, which can comprise plates and spacers. In some embodiments, the dimension of the individual components of the QMAX device and its adaptor are listed, described and/or summarized in PCT Application (designating U.S.) No. PCT/US2016/046437 filed on Aug. 10, 2016, and U.S. Provisional Application Nos. 62,431,639 filed on Dec. 9, 2016 and 62/456,287 filed on Feb. 8, 2017, which are all hereby incorporated by reference by their entireties.

In some embodiments, the dimensions are listed in the Tables below:

Plates:

| Parameters | Embodiments | Preferred Embodiments |
| --- | --- | --- |
| Shape | round, ellipse, rectangle, triangle, polygonal, ring-shaped, or any superposition of these shapes; the two (or more) plates of the QMAX card can have the same size and/or shape, or different size and/or shape; | at least one of the two (or more) plates of the QMAX card has round corners for user safety concerns, wherein the round corners have a diameter of 100 μm or less, 200 μm or less, 500 μm or less, 1 mm or less, 2 mm or less, 5 mm or less, 10 mm or less, 50 mm or less, or in a range between any two of the values. |
| Thickness | the average thickness for at least one of the plates is 2 nm or less, 10 nm or less, 100 nm or less, 200 nm or less, 500 nm or less, 1000 nm or less, 2 μm (micron) or less, 5 μm or less, 10 μm or less, 20 μm or less, 50 μm or less, 100 μm or less, 150 μm or less, 200 μm or less, 300 μm or less, 500 μm or less, 800 μm or less, 1 mm (millimeter) or less, 2 mm or less, 3 mm or less, 5 mm or less, 10 mm or less, 20 mm or less, 50 mm or less, 100 mm or less, 500 mm or less, or in a range between any two of these values | For at least one of the plates is in the range of 0.5 to 1.5 mm; around 1 mm; in the range of 0.15 to 0.2 mm; or around 0.175 mm |
| Lateral Area | For at least one of the plate is 1 mm2 (square millimeter) or less, 10 mm2 or less, 25 mm2 or less, 50 mm2 or less, 75 mm2 or less, 1 cm2 (square centimeter) or less, 2 cm2 or less, 3 cm2 or less, 4 cm2 or less, 5 cm2 or less, 10 cm2 or less, 100 cm2 or less, 500 cm2 or less, 1000 cm2 or less, 5000 cm2 or less, 10,000 cm2 or less, 10,000 cm2 or less, or in a range between any two of these values | For at least one plate of the QMAX card is in the range of 500 to 1000 mm$^2$; or around 750 mm$^2$. |
| Lateral Linear Dimension (width, length, or diameter, etc.) | For at least one of the plates of the QMAX card is 1 mm or less, 5 mm or less, 10 mm or less, 15 mm or less, 20 mm or less, 25 mm or less, 30 mm or less, 35 mm or less, 40 mm or less, 45 mm or less, 50 mm or less, 100 mm or less, 200 mm or less, 500 mm or less, 1000 mm or less, 5000 mm or less, or in a range between any two of these values | For at least one plate of the QMAX card is in the range of 20 to 30 mm; or around 24 mm |
| Recess width | 1 μm or less, 10 μm or less, 20 μm or less, 30 μm or less, 40 μm or less, 50 μm or less, 100 μm or less, 200 μm or less, 300 μm or less, 400 μm or less, 500 μm or less, 7500 μm or less, 1 mm or less, 5 mm or less, 10 mm or less, 100 mm or less, or 1000 mm or less, or in a range between any two of these values. | In the range of 1 mm to 10 mm; Or About 5 mm |

Hinge:

| Parameters | Embodiments | Preferred Embodiments |
| --- | --- | --- |
| Number | 1, 2, 3, 4, 5, or more | 1 or 2 |
| Length of Hinge Joint | 1 mm or less, 2 mm or less, 3 mm or less, 4 mm or less, 5 mm or less, 10 mm or less, 15 mm or less, 20 mm or less, 25 mm or less, 30 mm or less, 40 mm or less, 50 mm or less, 100 mm or less, 200 mm or less, or 500 mm or less, or in a range between any two of these values | In the range of 5 mm to 30 mm. |
| Ratio (hinge joint length vs. aligning plate edge length | 1.5 or less, 1 or less, 0.9 or less, 0.8 or less, 0.7 or less, 0.6 or less, 0.5 or less, 0.4 or less, 0.3 or less, 0.2 or less, 0.1 or less, 0.05 or less or in a range between any two of these values. | In the range of 0.2 to 1; or about 1 |
| Area | 1 mm$^2$ or less, 5 mm$^2$ or less, 10 mm$^2$ or less, 20 mm$^2$ or less, 30 mm$^2$ or less, 40 mm$^2$ or less, 50 mm$^2$ or less, 100 mm$^2$ or less, 200 mm$^2$ or less, 500 mm$^2$ or less, or in a range between any of the two values | In the range of 20 to 200 mm$^2$; or about 120 mm$^2$ |
| Ratio (hinge area vs. plate area) | 1 or less, 0.9 or less, 0.8 or less, 0.7 or less, 0.6 or less, 0.5 or less, 0.4 or less, 0.3 or less, 0.2 or less, 0.1 or less, 0.05 or less, 0.01 or less or in a range between any two of these values | In the range of 0.05 to 0.2, around 0.15 |

-continued

| Parameters | Embodiments | Preferred Embodiments |
|---|---|---|
| Max. Open Degree | 15 or less, 30 or less, 45 or less, 60 or less, 75 or less, 90 or less, 105 or less, 120 or less, 135 or less, 150 or less, 165 or less, 180 or less, 195 or less, 210 or less, 225 or less, 240 or less, 255 or less, 270 or less, 285 or less, 300 or less, 315 or less, 330 or less, 345 or less or 360 or less degrees, or in a range between any two of these values | In the range of 90 to 180 degrees |
| No. of Layers | 1, 2, 3, 4, 5, or more | 1 or 2 |
| Layer thickness | 0.1 µm or less, 1 µm or less, 2 µm or less, 3 µm or less, 5 µm or less, 10 µm or less, 20 µm or less, 30 µm or less, 50 µm or less, 100 µm or less, 200 µm or less, 300 µm or less, 500 µm or less, 1 mm or less, 2 mm or less, and a range between any two of these values | In the range of 20 µm to 1 mm; or Around 50 µm |
| Angle-maintaining | Limiting the angle adjustment with no more than ±90, ±45, ±30, ±25, ±20, ±15, ±10, ±8, ±6, ±5, ±4, ±3, ±2, or ±1, or in a range between any two of these values | No more than ±2 |

Notch:

| Parameters | Embodiments | Preferred Embodiments |
|---|---|---|
| Number | 1, 2, 3, 4, 5, or more | 1 or 2 |
| Shape | round, ellipse, rectangle, triangle, polygon, ring-shaped, or any superposition or portion of these shapes. | Part of a circle |
| Positioning | Any location along any edge except the hinge edge, or any corner joint by non-hinge edges | |
| Lateral Linear Dimension (Length along the edge, radius, etc.) | 1 mm or less, 2.5 mm or less, 5 mm or less, 10 mm or less, 15 mm or less, 20 mm or less, 25 mm or less, 30 mm or less, 40 mm or less, 50 mm or less, or in a range between any two of these values | In the range of 5 mm to 15 mm; or about 10 mm |
| Area | 1 $mm^2$ (square millimeter) or less, 10 $mm^2$ or less, 25 $mm^2$ or less, 50 $mm^2$ or less, 75 $mm^2$ or less or in a range between any two of these values. | In the range of 10 to 150 $mm^2$; or about 50 $mm^2$ |

Trench:

| Parameters | Embodiments | Preferred Embodiments |
|---|---|---|
| Number | 1, 2, 3, 4, 5, or more | 1 or 2 |
| Shape | Closed (round, ellipse, rectangle, triangle, polygon, ring-shaped, or any superposition or portion of these shapes) or open-ended (straight line, curved line, arc, branched tree, or any other shape with open endings); | |
| Length | 0.001 mm or less, 0.005 mm or less, 0.01 mm or less, 0.05 mm or less, 0.1 mm or less, 0.5 mm or less, 1 mm or less, 2 mm or less, 5 mm or less, 10 mm or less, 20 mm or less, 50 mm or less, 100 mm or less, or in a range between any two of these values | |
| Cross-sectional Area | 0.001 $mm^2$ or less, 0.005 $mm^2$ or less, 0.01 $mm^2$ or less, 0.05 $mm^2$ or less, 0.1 $mm^2$ or less, 0.5 $mm^2$ or less, 1 $mm^2$ or less, 2 $mm^2$ or less, 5 $mm^2$ or less, 10 $mm^2$ or less, 20 $mm^2$ or less, or in a range between any two of these values. | |
| Volume | 0.1 µL or more, 0.5 µL or more, 1 µL or more, 2 µL or more, 5 µL or more, 10 µL or more, 30 µL or more, 50 µL or more, 100 µL or more, 500 µL or more, 1 mL or more, or in a range between any two of these values | In the range of 1 µL to 20 µL; or About 5 µL |

Receptacle Slot

| Parameters | Embodiments | Preferred Embodiments |
|---|---|---|
| Shape of receiving area | round, ellipse, rectangle, triangle, polygon, ring-shaped, or any superposition of these shapes; | |
| Difference between sliding track gap size and card thickness | 100 nm, 500 nm, 1 µm, 2 µm, 5 µm, 10 µm, 50 µm, 100 µm, 300 µm, 500 µm, 1 mm, 2 mm, 5 mm, 1 cm, or in a range between any two of the values. | In the range of 50 to 300 µm; or about 75 µm |
| Difference between receiving area and card area | 1 mm² (square millimeter) or less, 10 mm2 or less, 25 mm² or less, 50 mm² or less, 75 mm² or less, 1 cm² (square centimeter) or less, 2 cm² or less, 3 cm² or less, 4 cm² or less, 5 cm² or less, 10 cm² or less, 100 cm² or less, or in a range between any of the two values. | |

(12) Cloud

The devices/apparatus, systems, and methods herein disclosed can employ cloud technology for data transfer, storage, and/or analysis. The related cloud technologies are herein disclosed, listed, described, and/or summarized in PCT Application (designating U.S.) Nos. PCT/US2016/046437 and PCT/US2016/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

In some embodiments, the cloud storage and computing technologies can involve a cloud database. Merely by way of example, the cloud platform can include a private cloud, a public cloud, a hybrid cloud, a community cloud, a distributed cloud, an inter-cloud, a multi-cloud, or the like, or any combination thereof. In some embodiments, the mobile device (e.g. smartphone) can be connected to the cloud through any type of network, including a local area network (LAN) or a wide area network (WAN).

In some embodiments, the data (e.g. images of the sample) related to the sample is sent to the cloud without processing by the mobile device and further analysis can be conducted remotely. In some embodiments, the data related to the sample is processed by the mobile device and the results are sent to the cloud. In some embodiments, both the raw data and the results are transmitted to the cloud.

What is claimed is:

1. A device for analyzing a tissue sample, comprising:
a first plate; a second plate; a plurality of spacers; and a staining liquid, wherein:
the first and second plates are movable relative to each other into different configurations, including an open configuration and a closed configuration;
(ii) one or both plates are flexible;
(iii) each of the plates has, on its respective inner surface, a sample contact area for contacting the staining liquid and/or a tissue sample containing or suspected of containing a target analyte;
(iv) one or both of the plates comprise the plurality of spacers on a respective plate;
(v) the plurality of spacers have a predetermined substantially uniform height and a predetermined inter-spacer distance;
(vi) at least one of the plurality of spacers is inside the sample contact area; and
(vii) the staining liquid is deposited on (a) one or both of the plates in the open configuration or (b) the tissue sample;
wherein the open configuration is the configuration, in which: the two plates are partially or entirely separated apart, the spacing between the plates is not regulated by the plurality of spacers, and the tissue sample is deposited on one or both of the plates; and
wherein the closed configuration is the configuration that is configured after the open configuration; and in the closed configuration: at least part of the tissue sample and a layer of at least part of the staining liquid are between the two plates, wherein the thickness of the layer of at least part of the staining liquid is regulated by the plates, the tissue sample, and the plurality of spacers, and has an average distance between the sample surface and the surface of the plates that is equal to or less than 250 µm.

2. The device of claim 1, further comprising a stain agent coated on one or both of the sample contact areas of the plates, wherein the staining liquid comprises a transfer solution, and wherein the stain agent is configured, upon contacting the transfer solution, to be dissolved in the transfer solution to form a liquid that stains the tissue sample.

3. A method for analyzing a tissue sample, comprising the steps of:
(a) obtaining a tissue sample containing or suspected of containing a target analyte;
(b) obtaining the device of claim 1;
(c) depositing, when the plates are in the open configuration, (i) the tissue sample on one or both of the plates and (ii) the staining liquid on the tissue sample or on one or both of the plates;
(d) after (c), bringing the two plates together and pressing the plates into the closed configuration; and
(e) analyzing, without washing the tissue sample, the target analyte in the tissue sample when the plates are in the closed configuration.

4. A method for analyzing a tissue sample, comprising:
(a) obtaining a tissue sample containing or suspected of containing a target analyte;
(b) obtaining the device of claim 2;
(c) depositing, when the plates are in the open configuration, (i) the tissue sample on one or both of the plates and (ii) the transfer solution on the tissue sample or on one or both of the plates;

(d) after (c), bringing the two plates together and pressing the plates into the closed configuration; and (e) analyzing, without washing the tissue sample, the target analyte in the tissue sample when the plates are in the closed configuration.

5. The method of claim 3, wherein the step (e) uses one or more imagers that image the tissue sample generating one or more images.

6. A system for analyzing a tissue sample, comprising:
(a) the device of claim 1 or 2; and
(b) a detector, wherein the detector detects signals of the target analyte in the tissue sample.

7. A smartphone system for tissue analysis assay, comprising:
(a) the device of claim 1 or 2; and
(b) a mobile communication device that comprises:
   i. one or a plurality of cameras for detecting and/or imaging the tissue sample,
   ii. electronics, signal processors, hardware and software for receiving and/or processing the detected signal and/or the image of the tissue sample and for remote communication; and
(c) an adaptor that is configured to accommodate the device that is in the closed configuration and be engageable to the mobile communication device, wherein when engaged with the mobile communication device, the adaptor is configured to facilitate the detection and/or imaging of the target analyte in the tissue sample at the closed configuration.

8. The method of claim 3, wherein one or both of the plates is configured such that the tissue sample can be dried thereon at the open configuration, and wherein the tissue sample comprises bodily fluid selected from the group consisting of amniotic fluid, aqueous humour, vitreous humour, blood, breast milk, cerebrospinal fluid (CSF), cerumen (earwax), chyle, chime, endolymph, perilymph, feces, breath, gastric acid, gastric juice, lymph, mucus, pericardial fluid, peritoneal fluid, pleural fluid, pus, rheum, saliva, exhaled breath condensates, sebum, semen, sputum, sweat, synovial fluid, tears, vomit, urine, and any combination thereof.

9. The method of claim 3, wherein the tissue sample blood is whole blood, fractionated blood, plasma or serum.

10. The method of claim 3, wherein the tissue sample is mucus comprising nasal drainage or phlegm.

11. The device of claim 1, wherein the staining liquid has a viscosity in the range of 0.1 to 3.5 mPa S.

12. The method of claim 3, wherein the tissue sample is dried on one or both plates at the open configuration, and wherein the tissue sample comprises blood smear.

13. The device of claim 1, wherein the tissue sample contact area of one or both of the plates is configured to be adhesive to the tissue sample, and wherein the tissue sample is a tissue section having a thickness in the range of 1-200 µm.

14. The device of claim 1, wherein the tissue sample is paraffin-embedded.

15. The device of claim 1, wherein the tissue sample is fixed.

16. The device of claim 1, wherein the staining liquid comprises a fixative capable of fixing the tissue sample.

17. The device of claim 1, wherein the staining liquid comprises a blocking agent.

18. The device of claim 1, wherein the staining liquid comprises a deparaffinizing agent capable of removing paraffin in the sample.

19. The device of claim 1, wherein the staining liquid comprises a permeabilizing agent capable of permeabilizing cells in the tissue sample that contain the target analyte.

20. The device of claim 1, wherein the staining liquid comprises an antigen retrieval agent capable of facilitating retrieval of antigen.

21. The device of claim 1, wherein the staining liquid comprises a detection agent that specifically labels the target analyte in the tissue sample.

22. The device of claim 1, wherein the sample contact area of one or both plates comprises a storage site that contains a blocking agent.

23. The device of claim 1, wherein the sample contact area of one or both plates comprises a storage site that contains a deparaffinizing agent capable of removing paraffin in the tissue sample.

24. The device of claim 1, wherein the sample contact area of one or both plates comprises a storage site that contains a permeabilizing agent capable of permeabilizing cells in the tissue sample that contain the target analyte.

25. The device of claim 1, wherein the sample contact area of one or both plates comprises a storage site that contains an antigen retrieval agent capable of facilitating retrieval of antigen.

26. The device of claim 1, wherein the sample contact area of one or both plates comprises a storage site that contains a detection agent that specifically labels the target analyte in the tissue sample.

27. The device of claim 1, wherein the staining liquid comprises a detection agent, wherein the detection agent comprises a compound selected from the group consisting of: Acid fuchsin, Alcian blue 8 GX, Alizarin red S, Aniline blue WS, Auramine O, Azocarmine B, Azocarmine G, Azure A, Azure B, Azure C, Basic fuchsine, Bismarck brown Y, Brilliant cresyl blue, Brilliant green, Carmine, Chlorazol black E, Congo red, C.I. Cresyl violet, Crystal violet, Darrow red, Eosin B, Eosin Y, Erythrosin, Ethyl eosin, Ethyl green, Fast green F C F, Fluorescein Isothiocyanate, Giemsa Stain, Hematoxylin, Hematoxylin & Eosin, Indigo carmine, Janus green B, Jenner stain 1899, Light green SF, Malachite green, Martius yellow, Methyl orange, Methyl violet 2B, Methylene blue, Methylene blue, Methylene violet, Neutral red, Nigrosin, Nile blue A, Nuclear fast red, Oil Red , Orange G, Orange II, Orcein, Pararosaniline, Phloxin B, Protargol S, Pyronine B, Pyronine , Resazurin, Rose Bengal, Safranine O, Sudan black B, Sudan III, Sudan IV, Tetrachrome stain, Thionine, Toluidine blue, Weigert, Wright stain, and any combination thereof.

28. The device of claim 1, wherein one or both of the plates further comprise, on the respective sample contact area, a cell viability dye selected from the group consisting of: Propidium Iodide, 7-AAD, Trypan blue, Calcein Violet AM, Calcein AM, Fixable Viability Dyes, nucleic acid dyes, Resazurin and Formazan (MTT/XTT) and other mitochondrial dyes, and any combination thereof.

29. The device of claim 1, wherein the staining liquid comprises a detection agent, wherein the detection agent comprises an antibody that specifically binds to an antigen on the target analyte in the tissue sample.

30. The device of claim 1, wherein the staining liquid comprises a detection agent, wherein the detection agent comprises an oligonucleotide probe that specifically binds to DNA and/or RNA in the tissue sample.

31. The device of claim 1, wherein the staining liquid comprises a detection agent that is labeled with a reporter molecule, wherein the reporter molecule provides a detectable signal to be read and analyzed.

32. The method of claim 3, wherein the analyzing detects a detectable signal that is selected from the group consisting of:
  i. luminescence selected from photoluminescence, electroluminescence, and electrochemiluminescence,
  ii. light absorption, reflection, transmission, diffraction, scattering, or diffusion,
  iii. surface Raman scattering,
  iv. electrical impedance selected from resistance, capacitance, and inductance,
  v. magnetic relaxivity and
  vi. a combination thereof.

33. The device of claim 1, wherein the sample contact area of one or both of the plates comprises a binding site that contains a capture agent, wherein the capture agent binds to the target analyte on the surface of cells in the tissue sample and immobilizes the cells.

34. The method of claim 3, wherein the depositing step (c) comprises depositing, when the plates are in the open configuration, the tissue sample on one or both of the plates, drying the tissue sample on one or both of the plates, and depositing the staining liquid on top of the dried tissue sample, and wherein the tissue sample comprises a blood smear.

35. The method of claim 3, wherein the depositing step (c) comprises depositing and attaching, when the plates are in the open configuration, the tissue sample to one or both of the plates and depositing the staining liquid on top of the tissue sample attached to one or both of the plates, wherein the sample contact area of one or both of the plates is adhesive to the tissue sample, and wherein the tissue sample is a tissue section having a thickness in the range of 1-200 μm.

36. The method of claim 3, wherein the staining liquid comprises a detection agent that specifically labels the target analyte in the tissue sample, and wherein the method further comprises, before the analyzing step (e), incubating the tissue sample at the closed configuration for a period of time that is longer than the time it takes for the detection agent to diffuse across the layer of at least part of the transfer solution and the tissue sample.

37. The method of claim 3, wherein the method further comprises, before the analyzing step (e), incubating the tissue sample at the closed configuration at a predetermined temperature in the range of 30-75° C.

38. The method of claim 3, wherein the staining liquid comprises includes a transfer solution.

39. The smartphone system of claim 7, wherein the mobile communication device is configured to communicate test results to a medical professional, a medical facility or an insurance company.

40. The smartphone system of claim 7, wherein the mobile communication device is further configured to communicate information on the subject with the medical professional, medical facility or insurance company.

41. The smartphone system of claim 7, wherein the mobile communication device is configured to receive a prescription, diagnosis or a recommendation from a medical professional.

42. The smartphone system of claim 7, wherein the mobile communication device communicates with the remote location via a wireless or cellular network.

43. The smartphone system of claim 7, wherein the mobile communication device is a mobile phone.

44. The method of claim 3, wherein the pressing is performed by a human hand.

45. The device of claim 1, wherein at least a portion of the inner surface of one plate or both plates is hydrophilic.

46. The device of claim 1, wherein the inter spacer distance is periodic.

47. The device of claim 1, further comprising a hinge that connects the first plate and the second plate, and the plates can rotate around the hinge.

48. The device of claim 1, wherein the flexible plate has a thickness in the range of 20 μm to 200 μm and a Young's modulus in the range 0.1 to 5 GPa, and wherein the fourth power of the inter-spacer-distance (ISD) divided by the thickness (h) and the Young's modulus (E) of the flexible plate (ISD$^4$/(hE)) is $5 \times 10^6$ μm$^3$/GPa or less.

49. The device of claim 1, wherein the flexible plate has a thickness in the range of 20 μm to 200 μm and a Young's modulus in the range 0.1 to 5 GPa, and the fourth power of the inter-spacer-distance (ISD) divided by the thickness (h) and the Young's modulus (E) of the flexible plate (ISD$^4$/(hE)) is $5 \times 10^6$ μm$^3$GPa or less.

50. The device of claim 1 wherein the inter spacer distance (SD) is equal or less than about 120 μm (micrometer).

51. The device of claim 1 wherein the inter spacer distance (SD) is equal or less than about 100 μm (micrometer).

52. The device of claim 1, wherein the thickness of the flexible plate times the Young's modulus of the flexible plate is in the range of 60 to 750 GPa-μm, and wherein the fourth power of the inter-spacer-distance (ISD) divided by the thickness (h) and the Young's modulus (E) of the flexible plate (ISD$^4$/(hE)) is $5 \times 10^6$ μm$^3$/GPa or less.

53. The device of claim 1, wherein the thickness of the flexible plate times the Young's modulus of the flexible plate is in the range of 60 to 750 GPa-μm and the fourth power of the inter-spacer-distance (ISD) divided by the thickness (h) and the Young's modulus (E) of the flexible plate (ISD$^4$/(hE)) is $5 \times 10^5$ μm$^3$/GPa or less.

54. The device of claim 1, wherein each of the plurality of spacers has a height of 10 μm, wherein the thickness of the flexible plate times the Young's modulus of the flexible plate is in the range of 60 to 750 GPa-μm, and wherein the fourth power of the inter-spacer-distance (ISD) divided by the thickness (h) and the Young's modulus (E) of the flexible plate (ISD$^4$/(hE)) is $5 \times 10^6$ μm$^3$/Gpa or less.

55. The device of claim 1, wherein the target analyte is a protein, peptide, nucleic acid, synthetic compound, or an inorganic compound.

56. The method of claim 3, wherein the tissue sample is a biological sample selected from the group consisting of amniotic fluid, aqueous humour, vitreous humour, blood, breast milk, cerebrospinal fluid (CSF), cerumen (earwax), chyle, chime, endolymph, perilymph, feces, breath, gastric acid, gastric juice, lymph, mucus, pericardial fluid, peritoneal fluid, pleural fluid, pus, rheum, saliva, exhaled breath condensates, sebum, semen, sputum, sweat, synovial fluid, tears, vomit, and urine.

57. The method of claim 3, wherein the tissue sample has a thickness of 2 μm to 6 μm, wherein the thickness of the flexible plate times the Young's modulus of the flexible plate is in the range of 60 to 750 GPa-μm, and wherein the fourth power of the inter-spacer-distance (ISD) divided by the thickness (h) and the Young's modulus (E) of the flexible plate (ISD$^4$/(hE)) is $5 \times 10^6$ μm$^3$/GPa or less.

58. The method of claim 3, wherein each of the plurality of spacers have a pillar shape, and the pillar has substantially uniform cross-section.

59. The method of claim 3, wherein the tissue sample is for the detection, purification and quantification of chemical compounds or biomolecules that correlates with the stage of certain diseases.

60. The method of claim 3, wherein the tissue sample is related to infectious disease, parasitic disease, injuries, cardiovascular disease, cancer, mental disorders, neuropsychiatric disorders, pulmonary diseases, renal diseases, or other organic diseases.

61. The method of claim 3, wherein the tissue sample is related to the detection, purification and quantification of microorganism.

62. The method of claim 3, wherein the tissue sample is related to a virus, fungus, or and bacterium from environment.

63. The method of claim 3, wherein the tissue sample is related to the detection, quantification of chemical compounds or biological samples that pose hazard to food safety or national security.

64. The method of claim 3, wherein the tissue sample is related to quantification of vital parameters in medical or physiological monitor.

65. The method of claim 3, wherein the tissue sample is related to glucose, blood, oxygen level, or total blood count.

66. The method of claim 3, wherein the tissue sample is related to the detection and quantification of specific DNA or RNA from bio-samples.

67. The method of claim 3, wherein the tissue sample is related to the sequencing and comparing of genetic sequences in DNA in the chromosomes or mitochondria for genome analysis.

68. The method of claim 3, wherein the tissue sample is samples are related to detect reaction products.

69. The method of claim 3, wherein the tissue sample comprises cells, bodily fluid, or stool.

70. The method of claim 3, wherein the target analyte is a protein, peptides, nucleic acids, synthetic compounds, or inorganic compounds.

71. The method of claim 3, wherein the tissue sample is a sample in the field of human, veterinary, agriculture, foods, environments, or drug testing.

72. The method of claim 3, wherein the tissue sample is a biological sample selected from the group consisting of blood, serum, plasma, a nasal swab, a nasopharyngeal wash, saliva, urine, gastric fluid, spinal fluid, tears, stool, mucus, sweat, earwax, oil, a glandular secretion, cerebral spinal fluid, tissue, semen, vaginal fluid, interstitial fluids derived from tumorous tissue, ocular fluids, spinal fluid, a throat swab, breath, hair, finger nails, skin, biopsy, placental fluid, amniotic fluid, cord blood, lymphatic fluids, cavity fluids, sputum, pus, microbiota, meconium, breast milk, exhaled condensate nasopharyngeal wash, nasal swab, throat swab, stool samples, hair, finger nail, ear wax, breath, connective tissue, muscle tissue, nervous tissue, epithelial tissue, cartilage, cancerous sample, and bone.

73. The device of claim 1, wherein the staining liquid comprises: a fixative capable of fixing the tissue sample; a blocking agent; a deparaffinizing agent capable of removing paraffin in the tissue sample; a permeabilizing agent capable of permeabilizing cells in the tissue sample that contain the target analyte; an antigen retrieval agent capable of facilitating retrieval of antigen; a detection agent that specifically labels the target analyte in the tissue sample; a compound; a detection agent comprising an antibody that specifically binds to an antigen on the target analyte in the tissue sample; a detection agent comprising an oligonucleotide probe that specifically binds to DNA and/or RNA in the tissue sample; a detection agent that is labeled with a reporter molecule that provides a detectable signal to be read and analyzed; or any combination thereof.

74. The device of claim 2, wherein the stain agent comprises: a detection agent that specifically labels the target analyte in the tissue sample; a compound; a detection agent comprising an antibody that specifically binds to an antigen on the target analyte in the tissue sample; a detection agent comprising an oligonucleotide probe that specifically binds to DNA and/or RNA in the tissue sample; a detection agent that is labeled with a reporter molecule that provides a detectable signal to be read and analyzed; or any combination thereof.

75. The device of claim 1, wherein the sample contact area of one or both plates comprises a storage site that contains a blocking agent; a deparaffinizing agent capable of removing paraffin in the tissue sample; a permeabilizing agent capable of permeabilizing cells in the tissue sample that contain the target analyte; an antigen retrieval agent capable of facilitating retrieval of antigen; a detection agent that specifically labels the target analyte in the tissue sample; or any combination thereof.

76. The method of claim 3, wherein the staining liquid comprises oligonucleotide and/or RNA probes for in situ hybridization stain.

77. The method of claim 3, wherein the analyzing comprises a use of light.

78. The method of claim 3, wherein the staining liquid comprises a detection agent, wherein the detection agent comprises nucleic acid probes for in situ hybridization staining.

79. The device of claim 2, wherein the stain agent comprises a detection agent comprising an antibody that specifically binds to an antigen on the target analyte in the tissue sample.

80. The device of claim 2, wherein the stain agent comprises a detection agent comprising an antibody that specifically binds to an antigen on the target analyte in the tissue sample; a detection agent comprising an oligonucleotide probe that specifically binds to DNA and/or RNA in the tissue sample; an H&E stain agent; a stain agent that modifies the color of a specimen; or any combination thereof.

81. The device of claim 2, wherein the stain agent comprises a stain agent that modifies the color of a specimen.

82. The device of claim 2, wherein the stain agent comprises an H&E stain agent.

83. The method of claim 3, wherein an external force is used to bring the two plates together, and wherein the sample thickness is reduced in the closed configuration compared with the open configuration.

84. The device of claim 1, wherein each of the plurality of spacers has a height of 10 μm.

85. The device of claim 1, wherein each of the plurality of spacers has a height selected from 2 μm to 6 μm.

86. The device of claim 1, wherein the staining liquid comprises an immunohistochemical (IHC) stain agent.

87. The device of claim 1, wherein the staining liquid comprises a nucleic acid stain agent.

88. The device of claim 1, wherein the staining liquid comprises an H&E stain agent.

89. The device of claim 1, wherein the staining liquid comprises a stain agent that modifies the color of a specimen.

90. The device of claim 1, wherein the staining liquid comprises an immunohistochemical (IHC) stain agent; a nucleic acid stain agent; an H&E stain agent; a stain agent that modifies the color of a specimen; or any combination thereof.

91. The device of claim 2, wherein the staining agent comprises an immunohistochemical (IHC) stain agent; a nucleic acid stain agent; an H&E stain agent; a stain agent that modifies the color of a specimen; or any combination thereof.

92. The method of claim 3, wherein the analyzing comprises a machine learning.

93. The device of claim 1, wherein the plurality of spacers function as a location marker, a scale marker, an imaging marker, or any combination of thereof.

94. The device of claim 1, wherein one or both plates comprise a location marker, a scale marker, an imaging marker, or any combination of thereof.

95. The method of claim 3, wherein the analyzing is for checking cell viability.

96. The method of claim 3 or 4, wherein the sample is a biopsy sample.

97. The method of claim 3 or 4, wherein the sample is mucus, sputum, nasal swab, or throat swab.

98. The method of claim 3 or 4, wherein the target analyte is nucleic acid, and wherein the staining solution comprises a nucleic acid detection agent connected to a reporter that gives a fluorescent signal.

99. The device of claim 1, wherein the staining liquid comprises a detection agent that has a reporter comprising fluorescent molecules.

100. The device of claim 2, wherein the staining liquid comprises a detection agent that has a reporter comprising fluorescent molecules.

* * * * *